(12) United States Patent
Yamashita et al.

(10) Patent No.: US 7,735,485 B2
(45) Date of Patent: *Jun. 15, 2010

(54) DRY POWDER INHALATION SYSTEM FOR TRANSPULMONARY ADMINISTRATION

(75) Inventors: Chikamasa Yamashita, Naruto (JP); Akitsuna Akagi, Naruto (JP); Yuichiro Fukunaga, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 1291 days.

This patent is subject to a terminal disclaimer.

(21) Appl. No.: 10/538,837

(22) PCT Filed: Dec. 12, 2003

(86) PCT No.: PCT/JP03/15931

§ 371 (c)(1),
(2), (4) Date: Jun. 13, 2005

(87) PCT Pub. No.: WO2004/054555

PCT Pub. Date: Jul. 1, 2004

(65) Prior Publication Data

US 2006/0073105 A1  Apr. 6, 2006
US 2007/0065371 A2  Mar. 22, 2007

(30) Foreign Application Priority Data

Dec. 13, 2002  (JP) ............... 2002-363158

(51) Int. Cl.
- A61M 15/00 (2006.01)
- A61M 13/00 (2006.01)
- A61K 9/14 (2006.01)
- A61K 9/19 (2006.01)
- A61K 9/00 (2006.01)

(52) U.S. Cl. ............ 128/202.17; 424/489; 424/46; 514/2

(58) Field of Classification Search ............ 424/46, 424/489; 514/2
See application file for complete search history.

(56) References Cited

U.S. PATENT DOCUMENTS

| | | | |
|---|---|---|---|
| 1,950,926 A * | 3/1934 | Lobl ............... | 128/203.22 |
| 3,874,381 A | 4/1975 | Baum | |
| 4,064,878 A | 12/1977 | Lundquist | |
| 4,940,662 A | 7/1990 | Yamazaki et al. | |
| 4,992,419 A | 2/1991 | Woog et al. | |
| 5,044,091 A | 9/1991 | Ueda et al. | |
| 5,326,753 A | 7/1994 | Ohtsuki et al. | |
| 5,349,947 A | 9/1994 | Newhouse et al. | |
| 5,354,934 A | 10/1994 | Pitt et al. | |
| 5,503,144 A | 4/1996 | Bacon | |
| 5,533,502 A * | 7/1996 | Piper ............... | 128/203.21 |
| 5,654,007 A | 8/1997 | Johnson et al. | |
| 5,752,505 A | 5/1998 | Ohki et al. | |
| 5,785,049 A | 7/1998 | Smith et al. | |
| 5,826,633 A | 10/1998 | Parks et al. | |
| 5,875,776 A * | 3/1999 | Vaghefi ............ | 128/203.15 |
| 5,889,202 A | 3/1999 | Alapati et al. | |
| 5,954,047 A | 9/1999 | Armer et al. | |
| 5,964,416 A | 10/1999 | Jaeger et al. | |
| 5,996,577 A | 12/1999 | Ohki et al. | |
| 6,153,224 A | 11/2000 | Staniforth | |
| 6,186,141 B1 | 2/2001 | Pike et al. | |
| 6,231,851 B1 | 5/2001 | Plantz et al. | |
| 6,284,282 B1 * | 9/2001 | Maa et al. ............. | 424/499 |
| 6,394,085 B1 * | 5/2002 | Hardy et al. .......... | 128/203.15 |
| 6,402,055 B1 | 6/2002 | Jaeger et al. | |
| 6,461,591 B1 * | 10/2002 | Keller et al. .......... | 424/45 |
| 6,497,373 B2 | 12/2002 | Jaeger et al. | |
| 6,503,537 B2 * | 1/2003 | Yang ................. | 424/491 |

(Continued)

FOREIGN PATENT DOCUMENTS

EP   0133 767 A2   3/1985

(Continued)

OTHER PUBLICATIONS

G. Slama et al., "A new non-invasive method for treating insulin-reaction: intranasal lyophilized glucagons," *Diabetologia*, 33:671-674 (1990).

(Continued)

*Primary Examiner*—Johann R Richter
*Assistant Examiner*—James H Alstrum Acevedo
(74) *Attorney, Agent, or Firm*—Finnegan, Henderson, Farabow, Garrett, & Dunner, L.L.P.

(57) ABSTRACT

A dry powder inhalation system suitable for transpulmonary administration. The dry powder inhalation system is characterized by using a combination of:
(1) a vessel housing a freeze-dried composition prepared by freeze-drying a composition liquid containing ingredients in a non-dissolved form, and has:
   (i) a non-powder cake-like form,
   (ii) a disintegration index of 0.05 or more, and
   (iii) a property of becoming fine particles having a mean particle diameter (mass median aerodynamic diameter) of 10 microns or less or a fine particle fraction of 10% or more upon receipt of an air impact having an air speed of at least 1 m/sec and an air flow rate of at least 17 ml/sec; and
(2) a device comprising a member capable of applying the air impact to the freeze-dried composition in said vessel, and a member for discharging the powder-form freeze-dried composition that has been made into fine particles.

4 Claims, 13 Drawing Sheets

U.S. PATENT DOCUMENTS

| | | | |
|---|---|---|---|
| 6,726,124 | B2 | 4/2004 | Jaeger et al. |
| 2003/0101995 | A1 | 6/2003 | Yamashita et al. |
| 2003/0138402 | A1 | 7/2003 | Yamashita et al. |

FOREIGN PATENT DOCUMENTS

| | | | |
|---|---|---|---|
| EP | 0168 008 A2 | | 1/1986 |
| EP | 0360340 A1 | | 3/1990 |
| EP | 0407276 A | | 1/1991 |
| EP | 0437 622 A1 | | 7/1991 |
| EP | 0578 823 A1 | | 1/1994 |
| EP | 0709 085 A1 | | 5/1996 |
| EP | 1080720 A1 | | 3/2001 |
| HU | 204993 B | | 3/1992 |
| HU | 205857 B | | 7/1992 |
| HU | 216770 B | | 8/1999 |
| HU | 221232 B | | 8/2002 |
| JP | 60-52847 | | 4/1985 |
| JP | 3-131271 | | 6/1991 |
| JP | 06-321805 | | 11/1994 |
| JP | 8-103499 | | 4/1996 |
| JP | 11-171760 | | 6/1999 |
| JP | 2001-151673 | | 6/2001 |
| WO | WO 84/02274 | | 6/1984 |
| WO | WO 91/16038 | | 10/1991 |
| WO | WO 94/14492 | * | 7/1994 |
| WO | WO 94/28876 A1 | | 12/1994 |
| WO | WO 95/31479 | | 11/1995 |
| WO | WO 96/32149 | | 10/1996 |
| WO | WO 96/40068 | | 12/1996 |
| WO | WO 97/23239 | | 7/1997 |
| WO | WO 99/17754 | | 4/1999 |
| WO | WO 00/15263 | | 3/2000 |
| WO | WO 00/24444 | | 5/2000 |

OTHER PUBLICATIONS

P. Lucas et al., "Protein Deposition from Dry Powder Inhalers: Fine Particle Multiplets as Performance Modifiers," Pharmaceutical Research, vol. 15, No. 4, pp. 562-569 (New York, Plenum Publishing Corp., 1998).

U. Conte et al., "Spray Dried Microsphere Preparation: Influence of the Technological Parameters," Drug Development and Industrial Pharmacy, vol. 20, No. 3, pp. 235-258 (New York, Marcel Dekker, Inc., 1994).

K. Inazu & K. Shima, "Freeze-Drying and Quality Evaluation of Protein Drugs," Developments in Biological Standardization, vol. 74, pp. 307-322 (Basel, Switzerland, Karger AG, 1991).

"Aerosol Powder Device," A partial translation of Nippon Rinsho, vol. 56, No. 3 (Mar. 1998) p. 212 (764) left col. L6—p. 215 (767) left col. L25.

Pending Claims for U.S. Appl. No. 10/170,339.

Supplementary European Search Report, Appln. No./Patent No. 03778863.5-2114 / 1579855 PCT/JP0315931, Oct. 15, 2009.

* cited by examiner

DRY POWDER INHALATION SYSTEM FOR TRANSPULMONARY ADMINISTRATION

TECHNICAL FIELD

The present invention relates to a novel dry powder inhalation system suitable for transpulmonary administration. More specifically, the present invention relates to a dry powder inhalatjjon system for transpulmonary administration according to which a freeze-dried composition provided housed in a vessel can be prepared into a form suitable for transpulmonary administration by being made into fine particles at the time of use, and administered by inhalation as is.

Furthermore, the present invention encompasses the following inventions related to the dry powder inhalation system for transpulmonary administration. Specific examples of these inventions include a freeze-dried composition which can be made into fine particle powder suitable for transpulmonary administration (dry powdered preparation for transpulmonary administration) at the time of use, a method for producing the dry powdered preparation for transpulmonary administration, a method for transpulmonary administration by inhalation using the freeze-dried composition and use of a freeze-dried composition for preparing a dry powdered preparation for transpulmonary administration at the time of use.

Hereinafter, in this specification, the term "fine particles" includes substances having a fine structure regardless of a form such as a powder (particle powder) form, a needle-like form, a plate-like form and a fibrous form.

BACKGROUND ART

In general, with regard to transpulmonary administration, it is known that the active ingredient contained in a medicine can be delivered into the lungs efficiently by making the mean particle diameter of the active ingredient be 10 microns or less, preferably 5 microns or less. The current situation with conventional inhalations for transpulmonary administration is thus that, to make the medicine have a particle diameter suitable for transpulmonary administration in advance, fine particles are prepared by a spray drying method, a jet milling method or the like, and possibly further processing is carried out, and then the fine particles are provided filled into a dry powder inhaler.

Specifically, previously employed preparations include three types of dry powder inhalation, namely (1) a preparation comprising a powder-form composition comprising only medicinal fine particles filled into a suitable vessel, (2) a preparation comprising a powder-form composition in which medicinal fine particles have been granulated gently to form a relatively large particle diameter filled into a suitable vessel, and (3) a preparation comprising a powder-form composition comprising mixed particles in which medicinal fine particles and vehicle particles (lactose etc.) having a particle diameter larger than the medicinal fine particles are mixed together uniformly filled into a suitable vessel (refer to, for example, Japanese Unexamined Patent Publication No. 1999-171760). Moreover, it is disclosed that if these powdered inhalations are administered into the respiratory tract, then the behavior shown is that with (1) the medicinal fine particles in the composition reach the lower respiratory tract, for example the trachea and the bronchi, and are deposited here, with (2) the granulated medicine separates into fine particles in flight in the respiratory tract, and the medicinal fine particles produced reach the lower respiratory tract, for example the trachea and the bronchi, and are deposited here, and with (3) the vehicle is deposited in the oral cavity, on the pharynx or on the larynx, and the medicinal fine particles only reach the lower respiratory tract, for example the trachea and the bronchi, and are deposited here.

In this way, with a conventional powdered inhalation for transpulmonary administration, the ingredient to be inhaled is made into desirable fine particles in advance, and then these fine particles, or else these fine particles further processed by some methods, are filled into a dry powder inhaler, and transpulmonary administration is carried out using this.

To make a low-molecular-weight drug into fine particles, a spray drying method (for example, disclosed in Japanese Unexamined Patent Publication No. 1999-171760), a jet milling method (for example, disclosed in Japanese Unexamined Patent Publication No. 2001-151673) or the like is usually used. The jet milling method comprises applying an air impact having an air flow rate of at least 1000 L/min and an air speed not less than the sonic speed to a low-molecular-weight drug to make the drug into fine particles. No method is known which makes the drug into fine particles by a low air impact.

For a high-molecular-weight drug such as a peptide or protein, on the other hand, for example a method in which a spray solution of a medicinal stock liquid containing additives is subjected to spray drying, thus making the stock liquid into fine particles having a mean particle diameter of 5 microns or less in one step, and then these fine particles are filled into a dry powder inhaler (spray drying method: WO 95/31479), and a method in which a peptide or protein is freeze-dried along with additives, and then the freeze-dried composition is made into fine particles by jet milling or the like, and these fine particles are filled into a dry powder inhaler (freeze drying-jet milling method: WO 91/16038) are known.

However, conventional powdered inhalations for transpulmonary administration prepared by the above-mentioned spray drying method or freeze drying-jet milling method are not necessarily ideal preparations for high-molecular-weight drugs such as peptides and proteins in particular. For example, as shown by the disclosure in WO 95/31479 that about 25% deactivation of Interferon occurs during the spray drying process, it is anticipated that if the spray drying method is used, then proteins and the like will be deactivated in the manufacturing process and the activity of the drug will thus decrease. No method is known which makes a high-molecular-weight drug into fine particles by a low air impact, the same as a low-molecular-weight drug.

Moreover, with both the spray drying method and the freeze drying-jet milling method, an operation is required in which the fine powder prepared is collected from the spray drying apparatus or jet milling apparatus and is subdivided and filled into vessels. It is thus inevitable that, accompanying this operation, problems will arise such as the yield of the preparation decreasing due to collection or filling loss and the cost rising correspondingly, and the preparation being contaminated with impurities. Moreover, in general it is difficult to subdivide and fill the powder in small amounts with good accuracy. If the spray drying method or the freeze drying-jet milling method, for which such subdividing and filling of small amounts in powder form is essential, is used, then it is thus necessary to establish a method of filling with small amounts and good accurancy of powder. In actual fact, details of a system, apparatus and method for filing with a fine powder are disclosed in U.S. Pat. No. 5,826,633.

DISCLOSURE OF THE PRESENT INVENTION

It is an object of the present invention to solve the various problems of the above-mentioned conventional powdered inhalations for transpulmonary administration. Specifically, it is an object of the present invention to provide a novel preparation system and administration system that enables a freeze-dried composition that has been housed in vessels to be made into fine particles down to a particle diameter suitable for transpulmonary administration in the vessel, and then be used for transpulmonary administration by inhalation as is.

The present inventors carried out assiduous studies to attain the above object, and as a result discovered that if a pharmacologically active substance as active ingredients is filled as a liquid into vessels and then freeze-dried, then the non-powder-form freeze-dried composition thus prepared can unexpectedly be made into fine particles by a relatively low air impact while still housed in the vessel. Based on this knowledge, the present inventors carried out further studies, and as a result discovered that by using a freeze-dried composition, which has been housed in a non-powder form in a vessel, combined with a device comprising member for introducing air at a prescribed speed and flow rate into the vessel so as to be capable of applying a prescribed air impact to the composition, and member for discharging from the vessel the powdered composition that has been made into fine particles, then the freeze-dried preparation can be prepared into a fine particle powder form suitable for transpulmonary administration easily by a user at the time of use (specifically, at the time of inhalation), and thus, transpulmonary administration can be carried out by administering the fine particle powder as is by inhalation. Moreover, the present inventors discovered that a composition liquid containing pharmacologically active substances to be filled as a liquid into vessels can be prepared as a freeze-dried composition capable of being made into fine particles suitable for transpulmonary administration through a predetermined air impact, and further discovered that this is not limited to the case where the ingredients in particular to be the pharmacologically active substance as an active ingredient are clearly dissolved or mixed in a solvent, and moreover, the ingredients may be not dissolved or only partially dissolved (which state is called as "the non-dissolved form") in the solvent.

It was verified that, according to this transpulmonary administration system, all of the previously mentioned problems of conventional powdered inhalations for transpulmonary administration can be solved.

That is, the above-mentioned transpulmonary administration system of the present invention can be used for transpulmonary administration without the problem of contamination, since it is not necessary to subdivide and fill the powder form freeze-dried composition which was made into fine particles in another device, into vessels.

Moreover, according to the above-mentioned administration system, active ingredients such as proteins or peptides are not exposed to high temperature in the manufacturing process as is the case with the spray drying method and the like, and hence there is no problem of the pharmacological activity dropping due to exposure to high temperature. This member that the administration system of the present invention is an extremely useful system in particular with pharmacologically active substances such as peptides and proteins that are expensive drugs, since the manufacturing cost can be reduced. More specifically, the administration system of the present invention is economically useful. Moreover, according to the dry powder inhalation system of the present invention, an extremely high fine particle fraction (the amount of the drug reaching the lungs: fine particle fraction, respirable fraction) is obtained, and hence the drug can be delivered into the lungs efficiently.

The dry powder inhalation system of the present invention is characterized by using a freeze-dried composition in a non-powder cake-like form prepared by subjecting active ingredients-containing composition liquid in the non-dissolved form to freeze-dry as a preparation for transpulmonary administration. The dry powder inhalation system of the present invention in which the freeze-dried composition in a cake-like form thus prepared is applied to a dry powder inhaler is capable of achieving a significantly higher fine particle fraction compared to the case where a preparation made into fine particle powder having a size suitable for transpulmonary administration using a method employed for powder inhalants heretofore known, such as a jet milling method or a spray drying method, is applied to a dry powder inhaler of the present invention. For such reasons, the dry powder inhalation system of the present invention can be ranked as a high-performance transpulmonary administration system.

The present invention was developed based on this knowledge, and includes the following items.

Item 1. A freeze-dried composition for transpulmonary administration prepared by freeze-drying a composition liquid containing ingredients in a non-dissolved form which has the following properties (i) to (iii):

(i) a non-powder cake-like form, (ii) a disintegration index of 0.05 or more, and (iii) becoming fine particles having a mean particle diameter (mass median aerodynamic diameter) of 10 microns or less or a fine particle fraction of 10% or more upon receipt of an air impact having an air speed of at least 1 m/sec and an air flow rate of at least 17 ml/sec.

Item 2. The freeze-dried composition according to Item 1, wherein a high-molecular-weight drug is contained as an active ingredient.

Item 3. A method of manufacturing a dry powdered preparation for transpulmonary administration, comprising:

introducing air into a vessel to apply to a freeze-dried composition an air impact having an air speed of at least 1 m/sec and an air flow rate of at least 17 ml/sec using a device capable of applying said air impact to the freeze-dried composition in the vessel, thereby making said freeze-dried composition into fine particles having a mean particle diameter (mass median aerodynamic diameter) of 10 microns or less or a fine particle fraction of 10% or more;

the freeze-dried composition prepared by freeze-drying a composition liquid containing ingredients in a non-dissolved form and having the following properties:

(i) a non-powder cake-like form, (ii) a disintegration index of 0.05 or more, and (iii) becoming fine particles having a mean particle diameter of 10 microns or less or a fine particle fraction of 10% or more upon receipt of the air impact.

Item 4. The method of manufacturing a dry powdered preparation for transpulmonary administration according to Item 3, wherein the freeze-dried composition contains a high-molecular-weight drug as an active ingredient.

Item 5. The method of manufacturing a dry powdered preparation for transpulmonary administration according to Item 3 comprising pulverizing a freeze-dried composition into fine particles using a dry powder inhaler described under item (A) or (B) as a device:

(A) a dry powder inhaler for transpulmonary administration, being a device used for making a freeze-dried composition that has been housed in non-powder form in a vessel into fine particles, and administering the resulting fine particles to a user by inhalation, comprising a needle part having an air jet flow path, a needle part having a discharge flow path, air pressure-feeding member for feeding air into the air jet flow path of said needle part, and an inhalation port that communicates with the discharge flow path of said needle part, and characterized by being constituted such that a stopper that seals up said vessel is pierced by said needle parts, thus communicating the air jet flow path and the discharge flow path with the inside of said vessel, and air is jetted into said vessel through said air jet flow path using said air pressure-feeding member, thus pulverizing said freeze-dried composition into fine particles by the impact of the jetted air, and discharging the fine particles obtained from the inhalation port via said discharge flow path, or (B) a dry powder inhaler for transpulmonary administration, being a device used for making a freeze-dried composition that has been housed in non-powder form in a vessel into fine particles, and administering the resulting fine particles to a user by inhalation, comprising a needle part having a suction flow path, a needle part having an air introduction flow path, and an inhalation port that communicates with said suction flow path, and characterized by being constituted such that, in a state in which a stopper sealing up said vessel has been pierced by said needle parts, through the inhalation pressure of the user, air in said vessel is inhaled from said inhalation port, and at the same time outside air flows into said vessel, at a negative pressure, through said air introduction flow path, and as a result said freeze-dried composition is pulverized into fine particles by the impact of the air flowing in, and the fine particles obtained are discharged from the inhalation port through said suction flow path.

Item 6. A dry powder inhalation system for transpulmonary administration, using a combination of:

(1) a vessel housing a freeze-dried composition prepared by freeze-drying a composition liquid containing ingredients in a non-dissolved form, and has:
(i) a non-powder cake-like form,
(ii) a disintegration index of 0.05 or more, and
(iii) a property of becoming fine particles having a mean particle diameter (mass median aerodynamic diameter) of 10 microns or less or a fine particle fraction of 10% or more upon receiving an air impact having an air speed of at least 1 m/sec and an air flow rate of at least 17 ml/sec; and
(2) a device comprising a member capable of applying said air impact to the freeze-dried composition in said vessel, and a member for discharging the powder-form freeze-dried composition that has been made into fine particles.

Item 7. The dry powder inhalation system for transpulmonary administration according to Item 6, wherein the vessel and the device are used in combination at the time of inhalation.

Item 8. The dry powder inhalation system for transpulmonary administration according to Item 6, wherein the freeze-dried composition contains a high-molecular-weight drug as an active ingredient.

Item 9. The dry powder inhalation system for transpulmonary administration according to Item 6, wherein the device is:

A) a dry powder inhaler for transpulmonary administration, being a device used for making a freeze-dried composition that has been housed in non-powder form in a vessel into fine particles, and administering the resulting fine particles to a user by inhalation, comprising a needle part having an air jet flow path, a needle part having a discharge flow path, air pressure-feeding member for feeding air into the air jet flow path of said needle part, and an inhalation port that communicates with the discharge flow path of said needle part, and characterized by being constituted such that a stopper that seals up said vessel is pierced by said needle parts, thus communicating the air jet flow path and the discharge flow path with the inside of said vessel, and air is jetted into said vessel through said air jet flow path using said air pressure-feeding member, thus pulverizing said freeze-dried composition into fine particles by the impact of the jetted air, and discharging the fine particles obtained from the inhalation port via said discharge flow path, or B) a dry powder inhaler for transpulmonary administration, being a device used for making a freeze-dried composition that has been housed in non-powder form in a vessel into fine particles, and administering the resulting fine particles to a user by inhalation, comprising a needle part having a suction flow path, a needle part having an air introduction flow path, and an inhalation port that communicates with said suction flow path, and characterized by being constituted such that, in a state in which a stopper sealing up said vessel has been pierced by said needle parts, through the inhalation pressure of the user, air in said vessel is inhaled from said inhalation port, and at the same time outside air flows into said vessel, at a negative pressure, through said air introduction flow path, and as a result said freeze-dried composition is pulverized into fine particles by the impact of the air flowing in, and the fine particles obtained are discharged from the inhalation port through said suction flow path.

Item 10. A transpulmonary administration method comprising:

making a freeze-dried composition into fine particles having a mean particle diameter of 10 microns or less or a fine particle fraction of 10% or more by applying an air impact having an air speed of at least 1 m/sec and an air flow rate of at least 17 ml/sec to the freeze-dried composition at the time of use, and administering the resulting fine particle powder to a user by inhalation;

the freeze-dried composition being prepared by freeze-drying a composition liquid containing ingredients in a non-dissolved form and having the following properties:
(i) a non-powder cake-like form,
(ii) a disintegration index of 0.05 or more, and
(iii) becoming fine particles having a mean particle diameter of 10 microns or less or a fine particle fraction of 10% or more upon receipt of the air impact.

Item 11. The transpulmonary administration method according to Item 10, wherein the freeze-dried composition is housed in a vessel, and the fine particle powder are prepared using a device comprising a member capable of applying the air impact to the freeze-dried composition in the vessel and a member for discharging the resulting fine particle powder-form freeze-dried composition out of the vessel.

Item 12. The transpulmonary administration method according to Item 10, wherein the freeze-dried composition contains a high-molecular-weight drug as an active ingredient.

Item 13. The transpulmonary administration method according to Item 11, using a dry powder inhaler described under item (A) or (B) as the device:

(A) a dry powder inhaler for transpulmonary administration, being a device used for making a freeze-dried composition that has been housed in non-powder form in a vessel into fine particles, and administering the resulting fine particles to a user by inhalation, comprising a needle part having an air jet flow path, a needle part having a discharge flow path, air pressure-feeding member for feeding air into the air jet flow path of said needle part, and an inhalation port that communicates with the discharge flow path of said needle part, and characterized by being constituted such that a stopper that seals up said vessel is pierced by said needle parts, thus communicating the air jet flow path and the discharge flow path with the inside of said vessel, and air is jetted into said vessel through said air jet flow path using said air pressure-feeding member, thus pulverizing said freeze-dried composition into fine particles by the impact of the jetted air, and discharging the fine particles obtained from the inhalation port via said discharge flow path, or (B) a dry powder inhaler for transpulmonary administration, being a device used for making a freeze-dried composition that has been housed in non-powder form in a vessel into fine particles, and administering the resulting fine particles to a user by inhalation, comprising a needle part having a suction flow path, a needle part having an air introduction flow path, and an inhalation port that communicates with said suction flow path, and characterized by being constituted such that, in a state in which a stopper sealing up said vessel has been pierced by said needle parts, through the inhalation pressure of the user, air in said vessel is inhaled from said inhalation port, and at the same time outside air flows into said vessel, at a negative pressure, through said air introduction flow path, and as a result said freeze-dried composition is pulverized into fine particles by the impact of the air flowing in, and the fine particles obtained are discharged from the inhalation port through said suction flow path.

Item 14. Use of a freeze-dried composition for transpulmonary administration by inhalation, the freeze-dried composition prepared by freeze-drying a composition liquid containing ingredients in a non-dissolved form and having the following properties:
(i) a non-powder cake-like form,
(ii) a disintegration index of 0.05 or more, and
(iii) becoming fine particles having a mean particle diameter of 10 microns or less or a fine particle fraction of 10% or more upon receipt of an air impact having an air speed of at least 1 m/sec and an air flow rate of at least 17 ml/sec, and being used by forming into fine particles having said mean particle diameter or said fine particle fraction.

Item 15. The use of a freeze-dried composition for transpulmonary administration according to Item 14, wherein the freeze-dried composition is housed in a vessel, and the fine particles are prepared using a device comprising a member capable of applying the air impact to the freeze-dried composition in the vessel and a member for discharging the resulting fine particle powder-form freeze-dried composition out of the vessel.

Item 16. The use of a freeze-dried composition for transpulmonary administration according to Item 14, wherein the freeze-dried composition contains a high-molecular-weight drug as an active ingredient.

Item 17. Use of a freeze-dried composition for manufacture of a dry powdered preparation for transpulmonary administration by inhalation, the freeze-dried composition having the following properties:
(i) being prepared by freeze drying a composition liquid containing ingredients in the non-dissolved form,
(ii) a non-powder cake-like form,
(iii) a disintegration index of 0.05 or more, and
(iv) becoming fine particles having a mean particle diameter of 10 microns or less or a fine particle fraction of 10% or more upon receipt of an air impact having an air speed of at least 1 m/sec and an air flow rate of at least 17 ml/sec,
and being used by forming into fine particles having said mean particle diameter or said fine particle fraction at the time of use.

Item 18. The use of a freeze-dried composition for manufacture of a dry powdered preparation for transpulmonary administration by inhalation according to Item 17, wherein the freeze-dried composition contains a high-molecular-weight drug as an active ingredient.

Item 19. The use of a freeze-dried composition for manufacture of a dry powdered preparation for transpulmonary administration according to Item 17, wherein the freeze-dried composition is housed in a vessel, and the fine particles are prepared by using a device comprising a member for applying a prescribed air impact to the freeze-dried composition housed in the vessel and a member for discharging the resulting fine particle powder form freeze-dried composition out of the vessel.

Item 20. Use of a composition liquid containing ingredients in the non-dissolved form for manufacture of a freeze-dried composition having the following properties, which is used for manufacture of dry powdered preparation for transpulmonary administration:
(i) a non-powder cake-like form,
(ii) a disintegration index of 0.05 or more, and
(iii) becoming fine particles having a mean particle diameter of 10 microns or less or a fine particle fraction of 10% or more upon receipt of an air impact having an air speed of at least 1 m/sec and an air flow rate of at least 17 ml/sec, and being used by forming into fine particles having said mean particle diameter or said fine particle fraction at the time of use.

Item 21. The use of a composition liquid containing ingredients in the non-dissolved form according to Item 20, wherein the freeze-dried composition contains a high-molecular-weight drug as an active ingredient Item 22. The use of a composition liquid containing ingredients in the non-dissolved form according to Item 20, wherein the freeze-dried composition is housed in a vessel, and the fine particles are prepared by using a device comprising a member for applying a prescribed air impact to the freeze-dried composition housed in the vessel and a member for discharging the resulting fine particle powder form freeze-dried composition out of the vessel.

Figure 1:
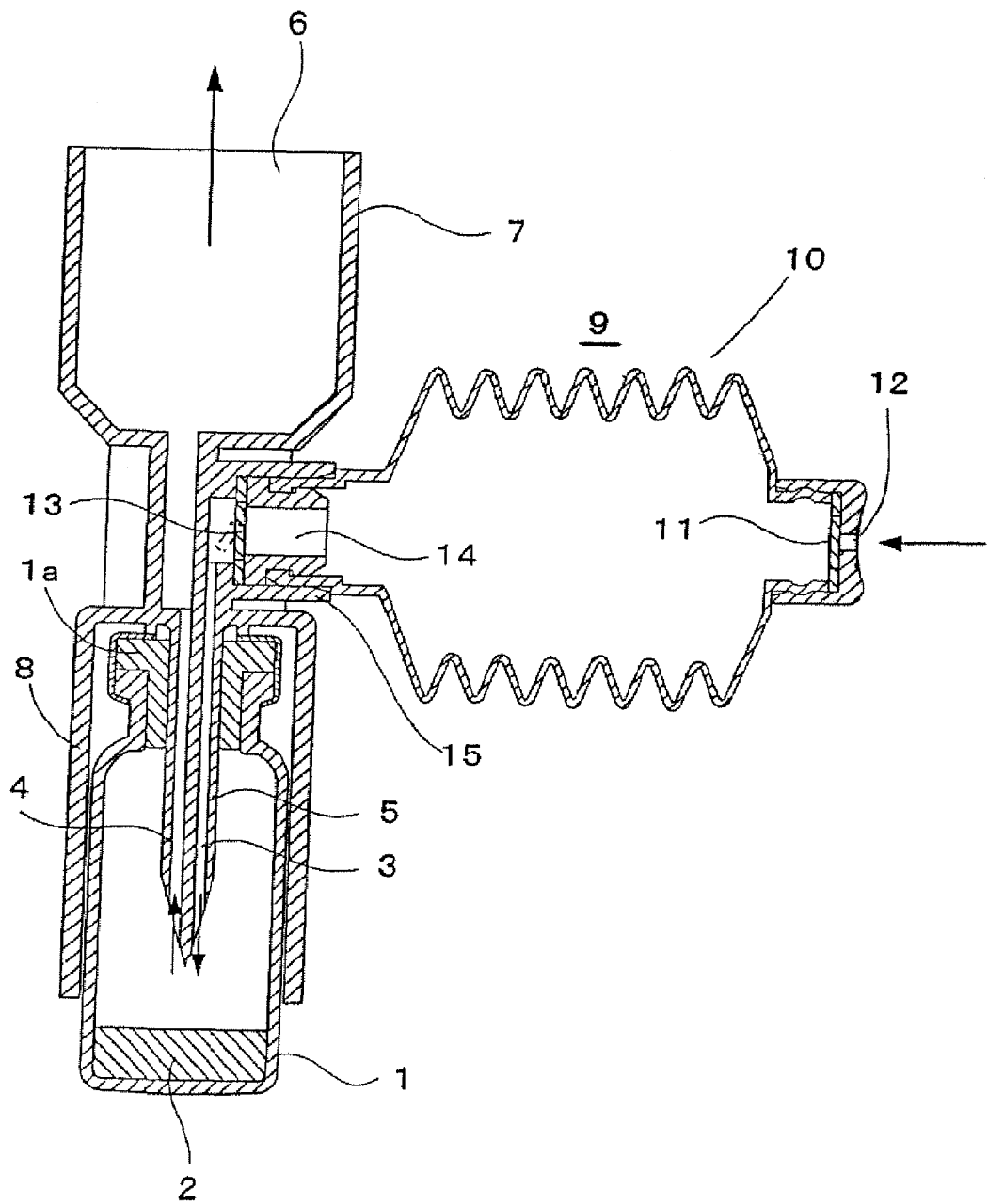
FIG. 1 is a cross section showing a dry powder inhaler (jet type 1) of the present invention disclosed as Embodiment 1. Note that, in the drawing, the arrows indicate the flow of external air (likewise in FIGS. 2 and 3 below).

Moreover, the meanings of the various reference numerals are as follows: 1. vessel, 1a. stopper, 2. freeze-dried composition, 3. air jet flow path, 4. discharge flow path, 5. needle part, 6. inhalation port, 7. air intake member, 8. tubular safety cover, 9. air pressure-feeding member, 10. bellows body, 11. intake valve, 12. intake port, 13. discharge valve, 14. discharge port, 15. connecting port (likewise in FIGS. 2 to 11 below).

Figure 2:
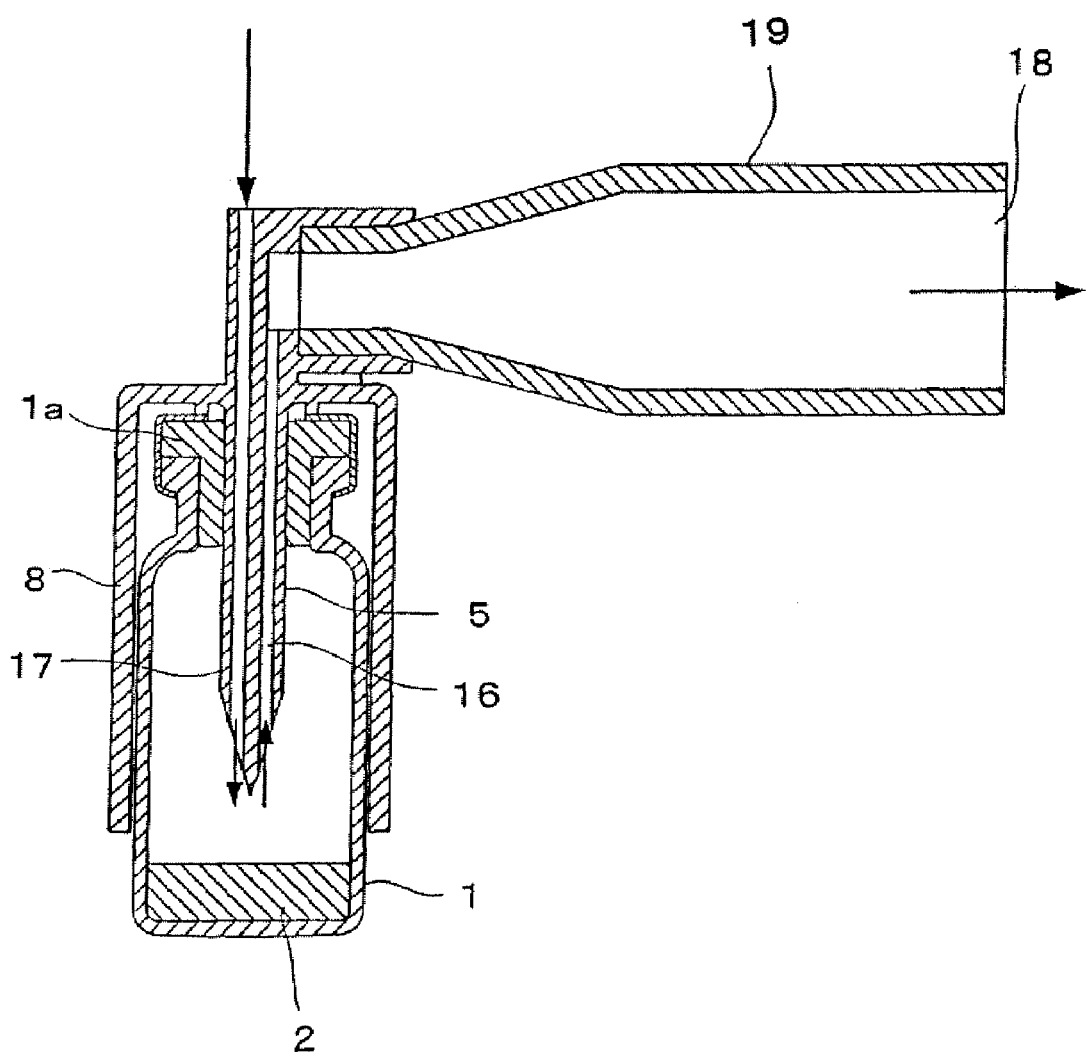

FIG. 2 is a cross section showing a dry powder inhaler (self-inhaling type 1) of the present invention disclosed as Embodiment 2. Moreover, the meanings of the various reference numerals are as follows: 16. suction flow path, 17. air introduction flow path, 18. inhalation port, 19. air intake member (likewise in FIG. 3 below).

Figure 3:
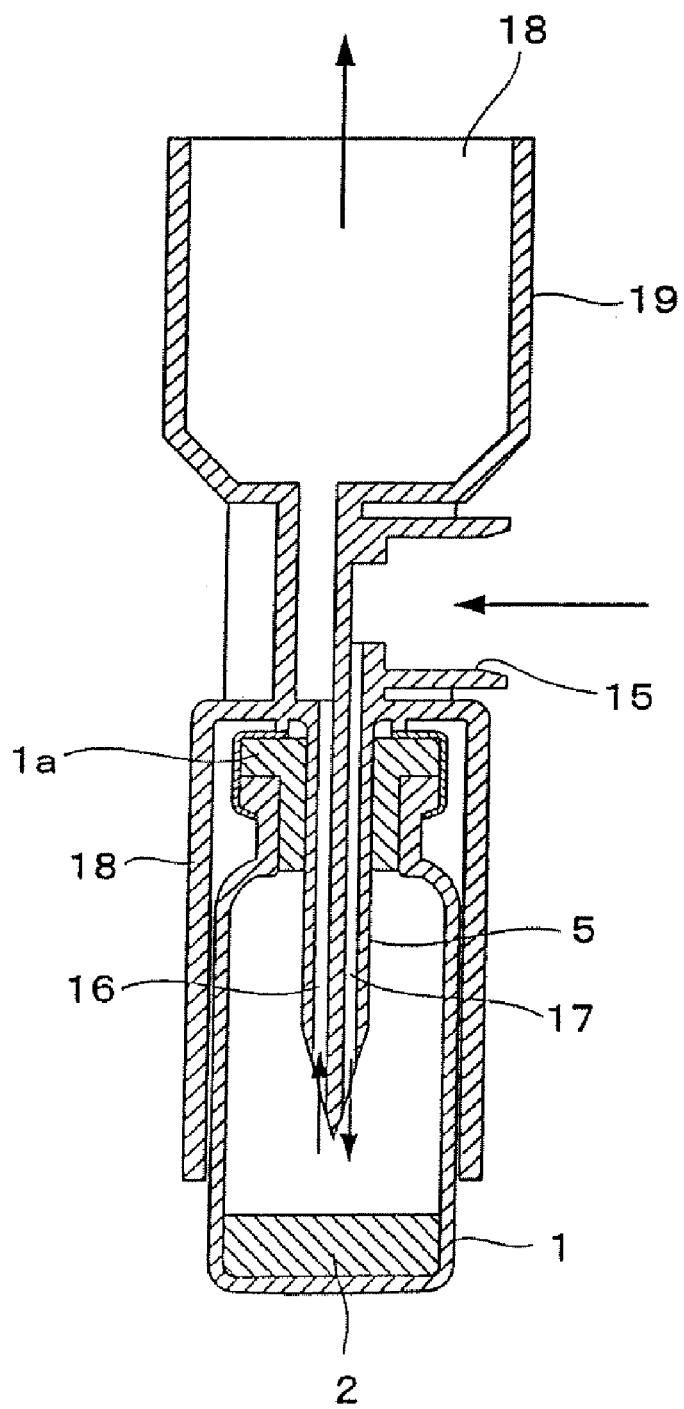

FIG. 3 is a cross section showing a dry powder inhaler (self-inhaling type 2) of the present invention disclosed as Embodiment 3.

Figure 4:
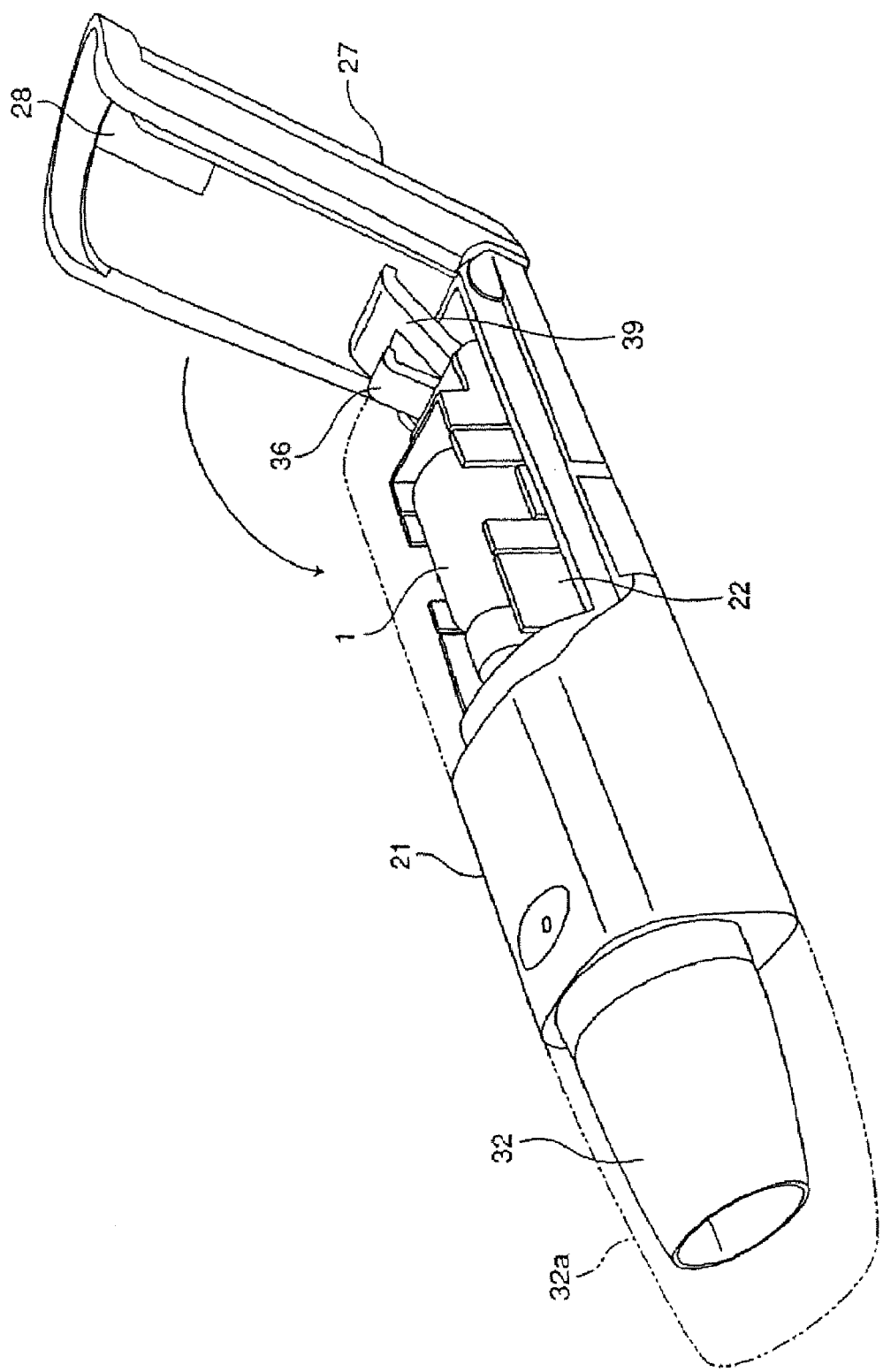

FIG. 4 is a perspective view showing a dry powder inhaler (self inhaling type 3) of the present invention disclosed as Embodiment 4. Moreover, the meanings of the reference numerals areas follows: 21. housing, 22. holder part, 27. lid, 28. window, 32. mouthpiece, 32a. mouthpiece cap, 39. connector (likewise in FIGS. 5 to 13 below).

Figure 5:
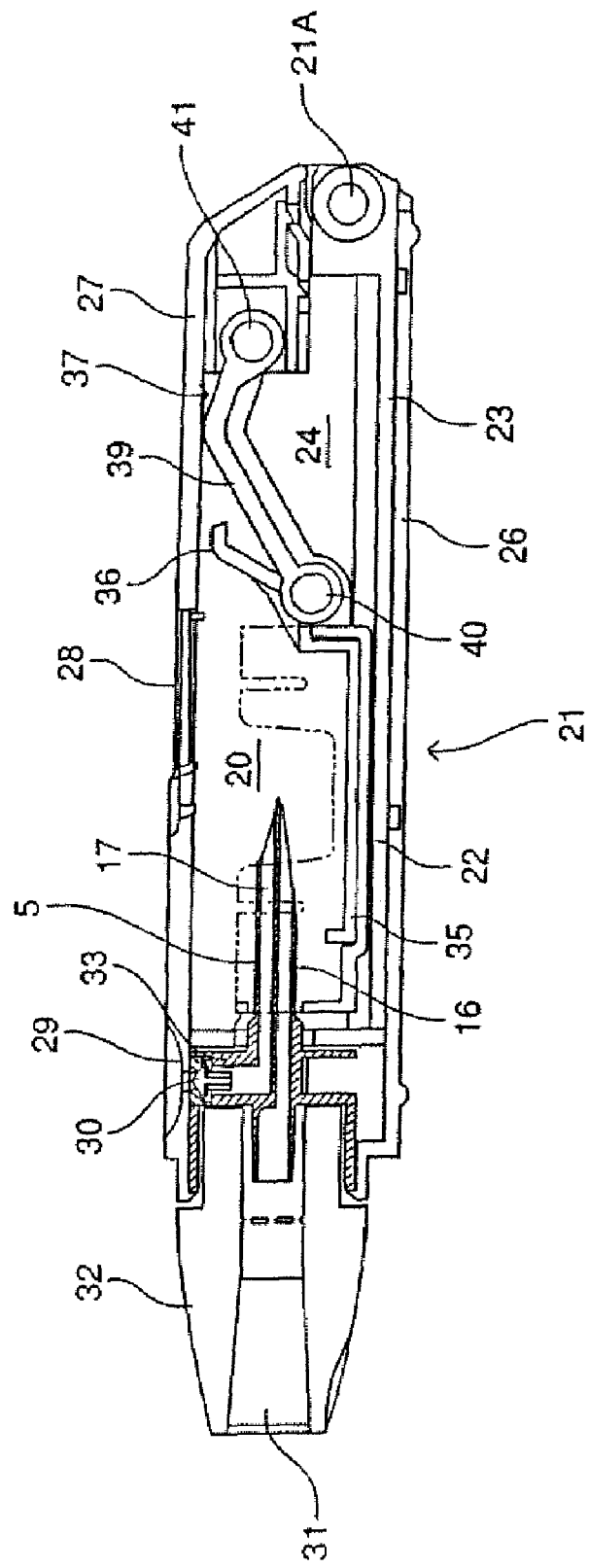

FIG. 5 is across section of the above-mentioned dry powder inhaler (self-inhaling type 3). Moreover, the meanings of the reference numerals are as follows: 20. housing chamber, 21A. hinge, 23. guide part, 24. holder operating part, 26. housing main body, 29. introduction port, 30. check valve, 31. suction port, 33. partition part, 35. remover, 36. lever, 37. mechanism part, 39. connector, 40. hinge, 41. hinge (likewise in FIGS. 6 to 13 below).

Figure 6:
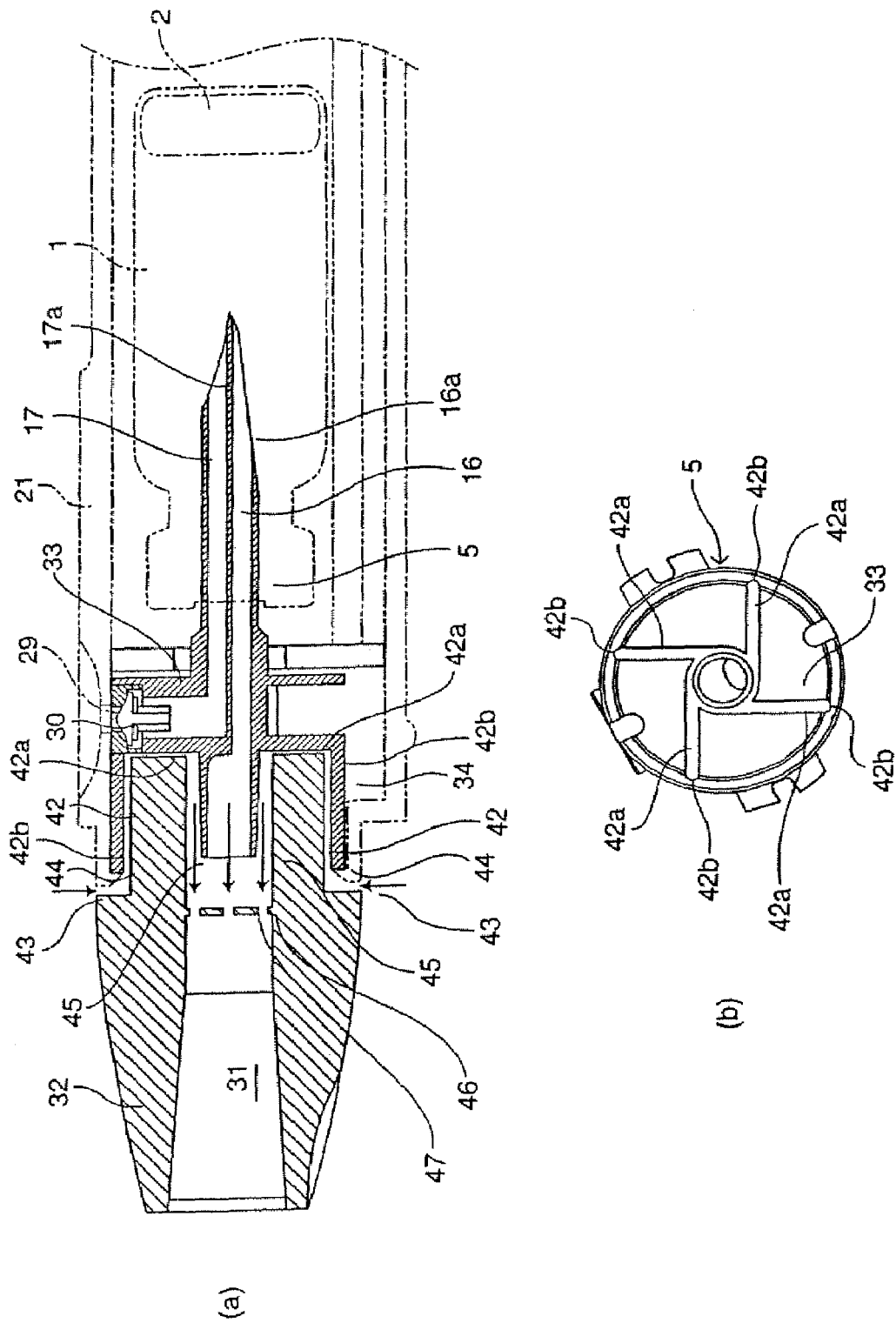
Figure 7:
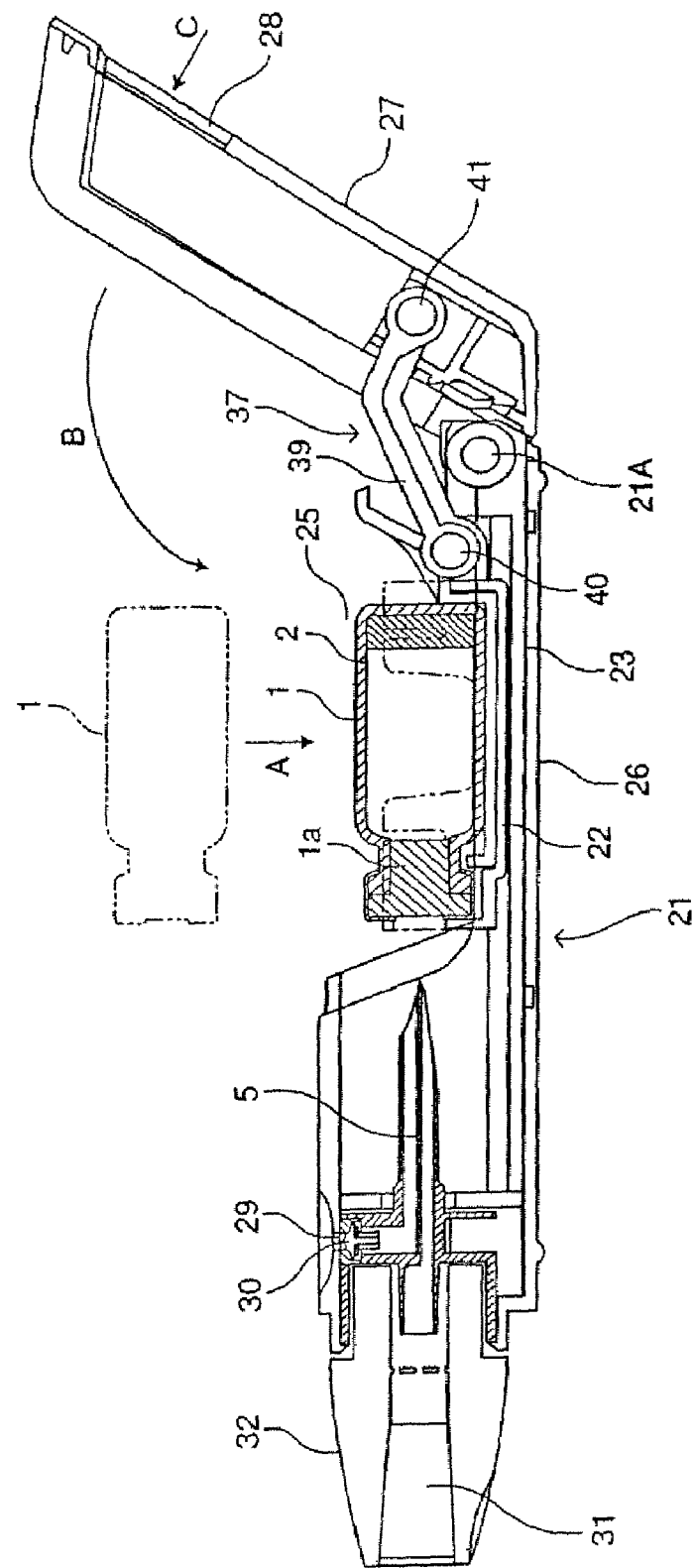
Figure 8:
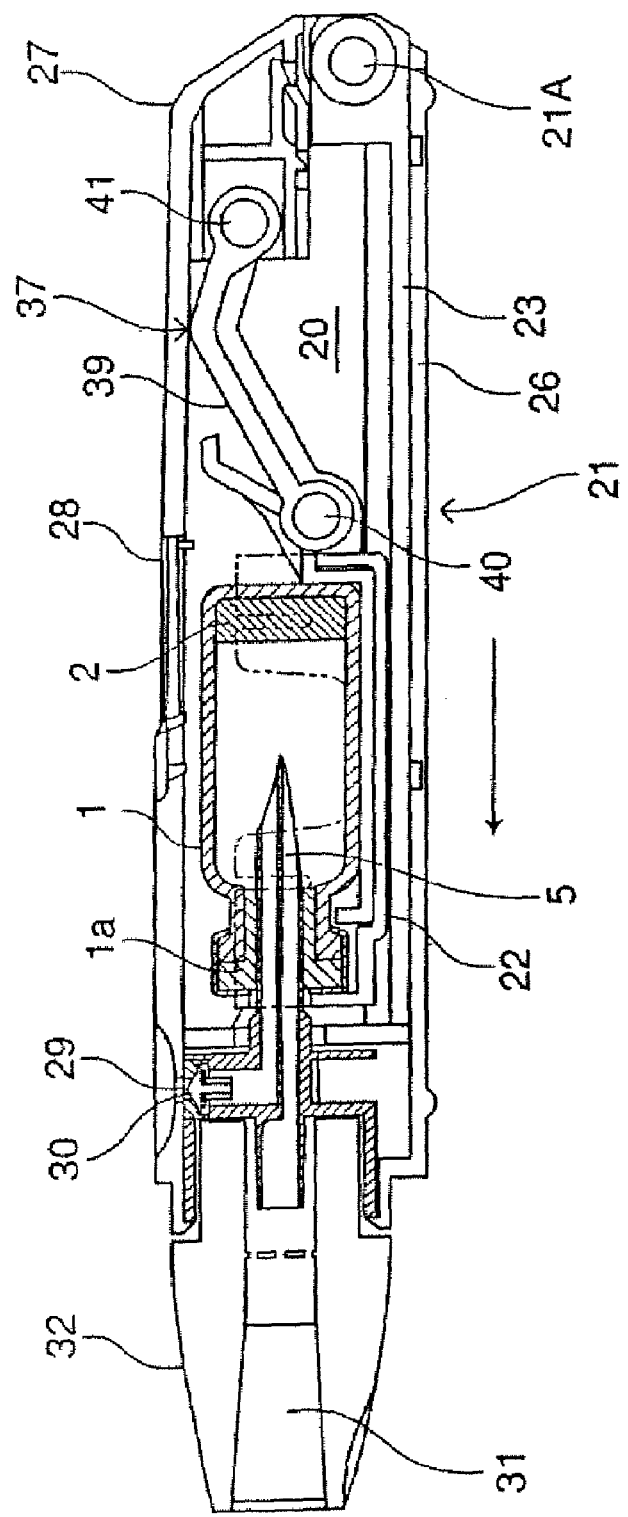
Figure 9:
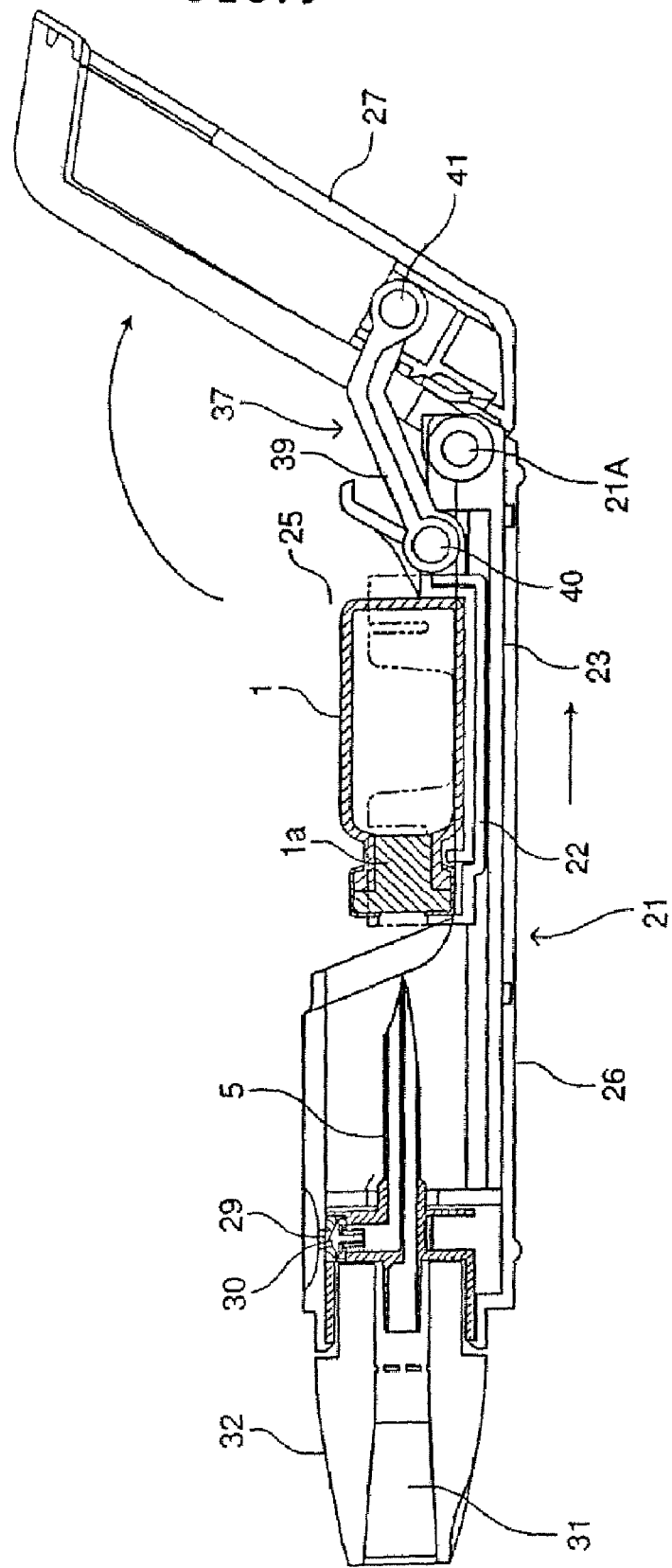
Figure 10:
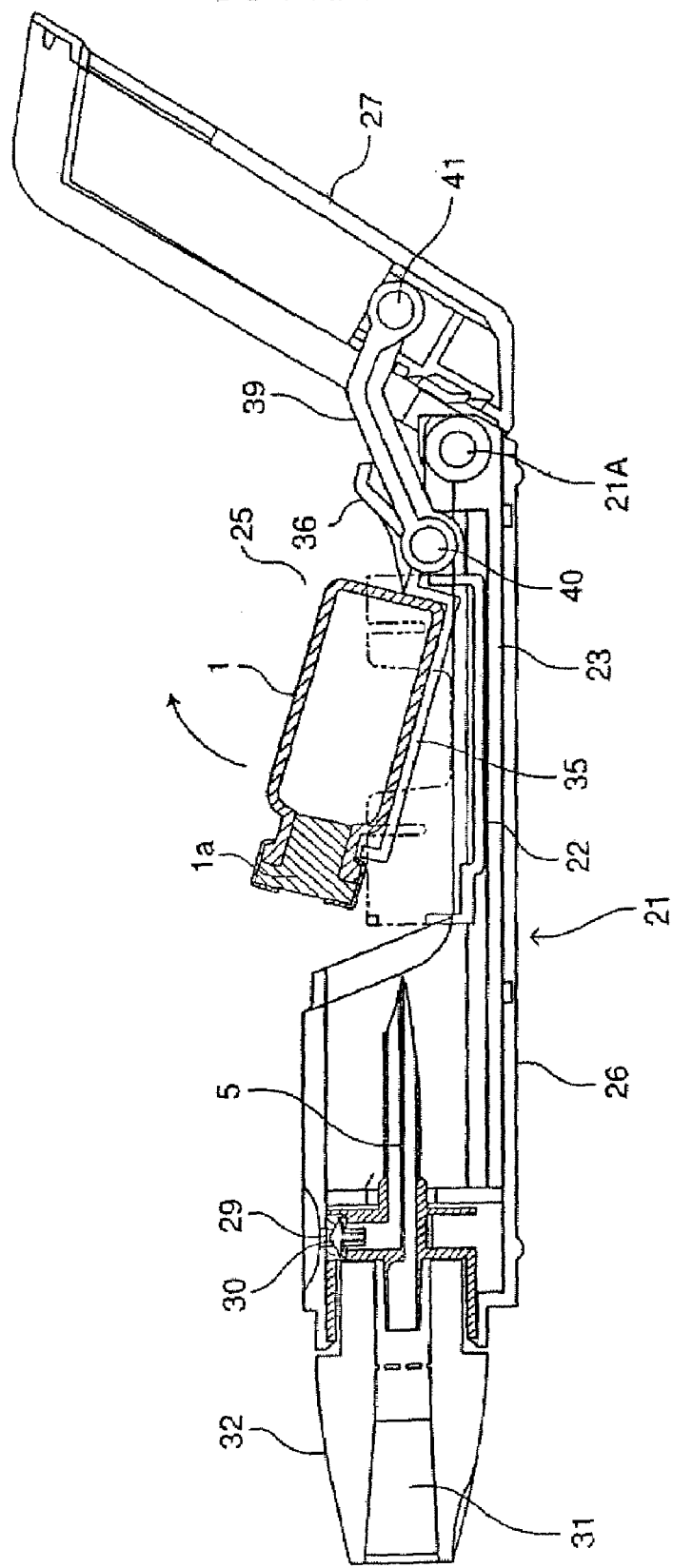

FIG. 6(a) is a cross section of part of the above-mentioned dry powder inhaler (self-inhaling type 3). FIG. 6 (b) is a side view of the needle part of this dry powder inhaler. Moreover, the meanings of the reference numerals are as follows: 16a. tip opening of suction flow path 16, 17a. tip opening of air introduction flow path 17, 34. peripheral wall part, 42. second introduction path, 42a. introduction groove in partition part 33, 42b. introduction groove in peripheral wall part 34, 43. gap, 44. one end of second introduction path 42, 45. other end of second introduction path 42, 46. vent hole, 47. wall (likewise in FIGS. 7 to 13 below).

FIGS. 7 to 10 are sectional view for explaining the operation of the above-mentioned dry powder inhaler (self-inhaling type 3). Reference numeral 25 indicates a removal/insertion port.

Figure 11:
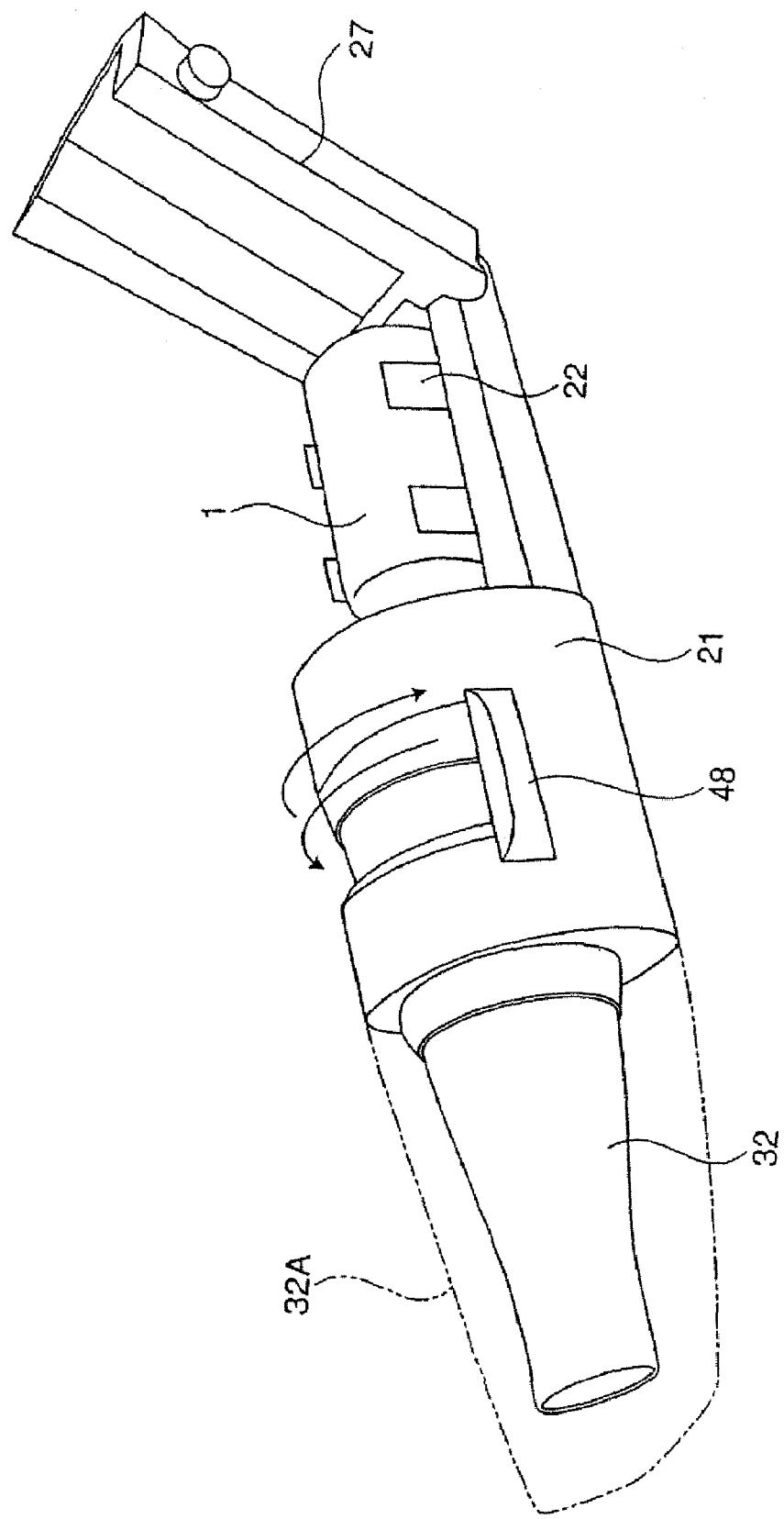

FIG. 11 is a perspective view of a dry powder inhaler (self-inhaling type 4), which is another embodiment of the present invention. Reference numeral 48 indicates an operator.

Figure 12:
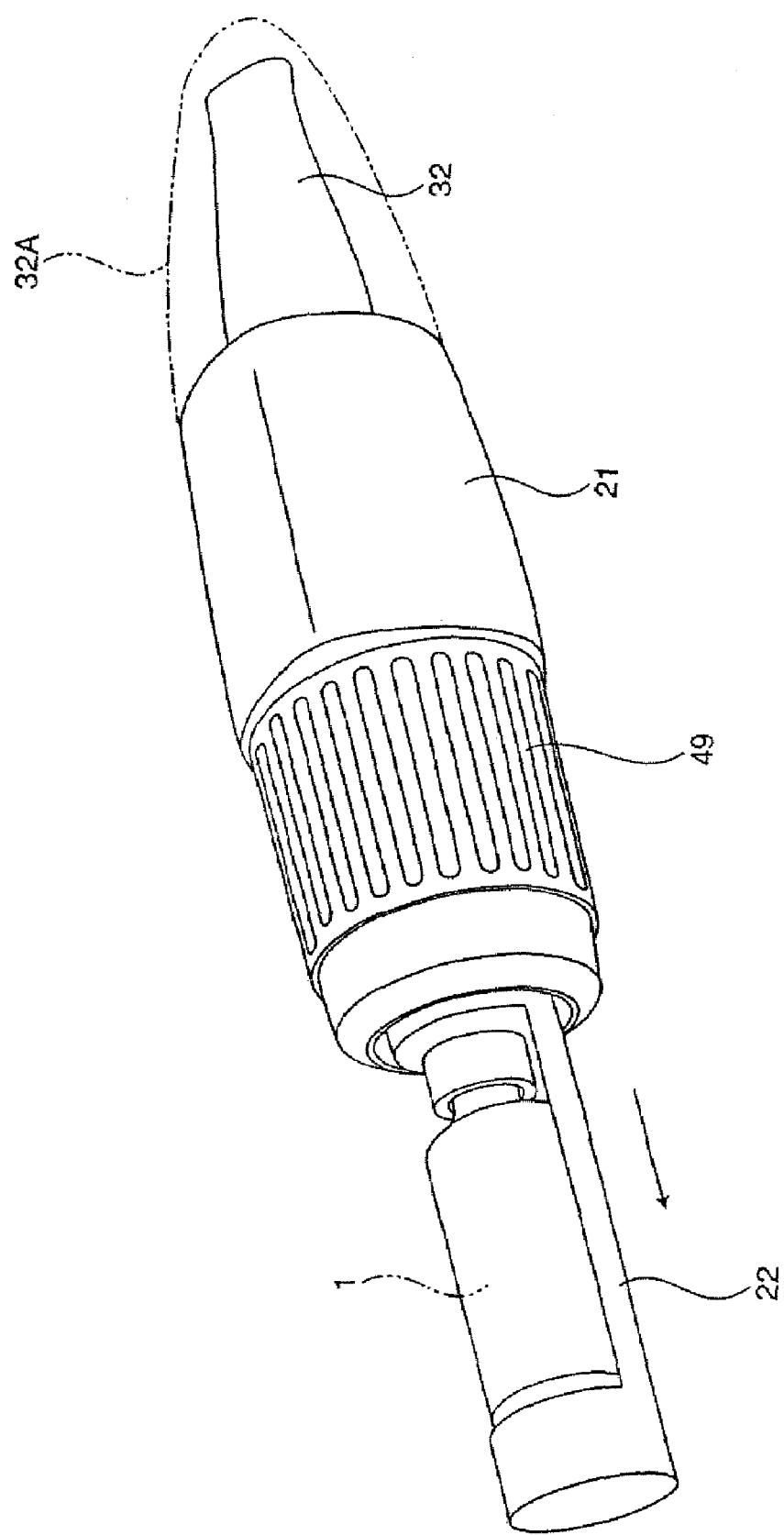

FIG. 12 is a perspective view of a dry powder inhaler (self-inhaling type 5) of another embodiment of the present invention. Reference numeral 49 indicates an operator.

Figure 13:
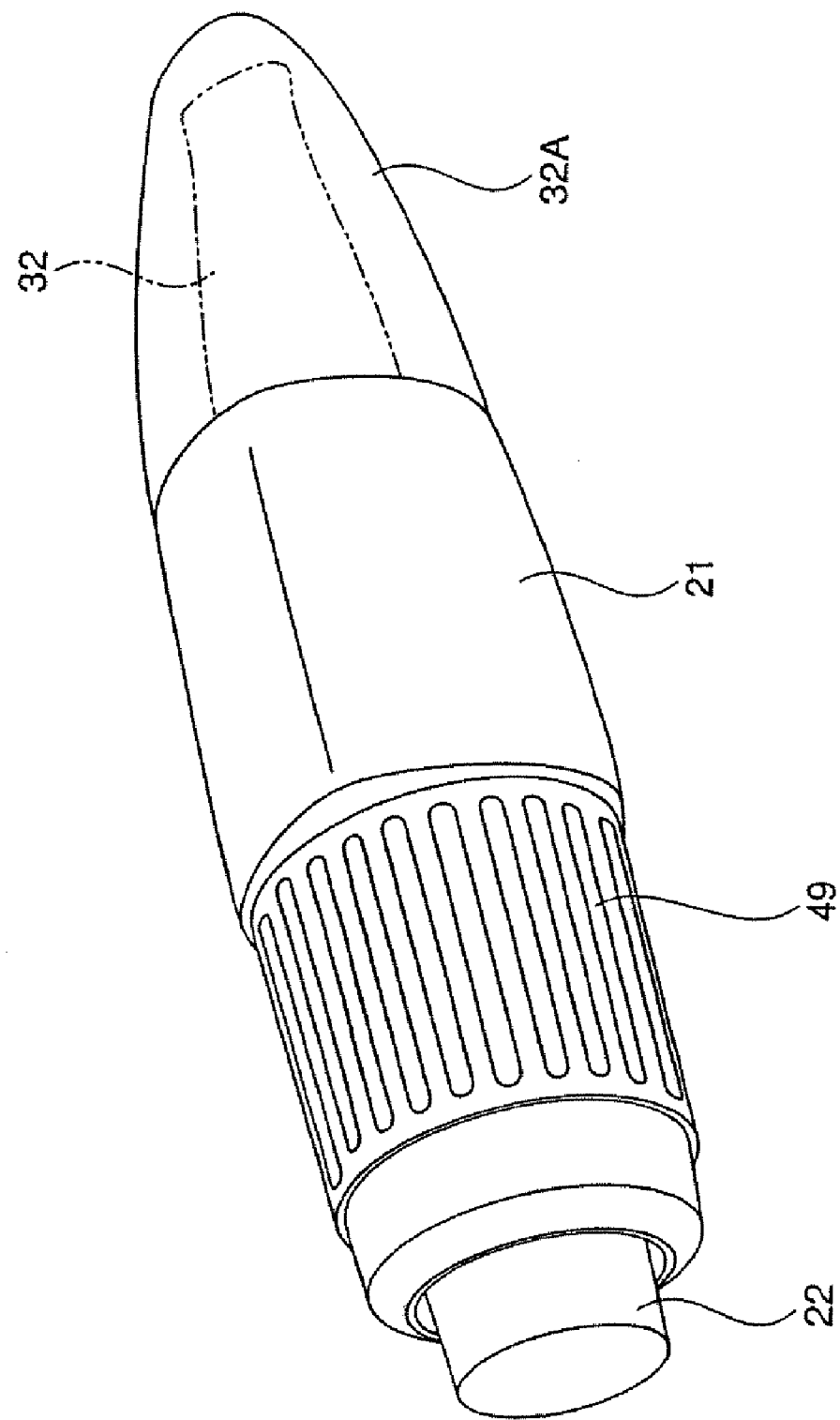

FIG. 13 is a perspective view of a dry powder inhaler (self-inhaling type 5) of another embodiment of the present invention. Reference numeral 49 indicates an operator.

BEST MODE FOR CARRYING OUT THE INVENTION (1) Freeze-Dried Composition

The freeze-dried composition of the present invention is a composition that is prepared in a non-powder dry form by filling composition liquid containing ingredients in the non-dissolved form into a vessel and then freeze-drying the same as is. The freeze-dried composition is prepared by freeze-drying composition liquid in the non-dissolved form containing preferably a single or a plurality of effective doses of active ingredients, and in particular, preferably a single dose of effective dose of active ingredients.

The freeze-dried composition of the present invention is prepared by selecting a composition (types and amounts of active ingredient and carrier used together with the active ingredient) of the composition liquid such that the disintegration index of the freeze-dried composition prepared is 0.05 or more, and thus the freeze-dried composition can be made into fine particles down to a particle diameter suitable for transpulmonary administration in an instant by receiving an impact of external air (air impact, jet pressure) introduced into (flowing into) the vessel.

Note that the disintegration index in the present invention is a value characteristic of the freeze-dried composition that can be obtained by measuring following the undermentioned method.

<Disintegration Index>

0.2 to 0.5 ml of a mixture containing target components that will constitute the freeze-dried composition is filled into a vessel having a trunk diameter of 18 mm or 23 mm, and freeze-drying is carried out. Next, 1.0 ml of n-hexane is instilled gently down the wall of the vessel onto the non-powder-form freeze-dried composition obtained. Agitation is carried out for about 10 seconds at 3000 rpm, and then the mixture is put into a UV cell of optical path length 1 mm and optical path width 10 mm, and the turbidity is measured immediately at a measurement wavelength of 500 nm using a spectrophotometer. The turbidity obtained is divided by the total amount (weight) of the components constituting the freeze-dried composition, and the value obtained is defined as the disintegration index.

Here, an example of the lower limit of the disintegration index of the freeze-dried composition of the present invention can be given as the above-mentioned 0.05, preferably 0.08, more preferably 0.09, yet more preferably 0.1, still more preferably 0.11, still further preferably 0.12, and in particular 0.13 is preferable.

Moreover, there is no particular limitation on the upper limit of the disintegration index of the freeze-dried composition of the present invention, but an example can be given as 1.5, preferably 1, more preferably 0.9, yet more preferably 0.8, and still more preferably 0.7. In particular, 0.6 is preferable, and 0.5 is more preferable. The freeze-dried composition of the present invention preferably has a disintegration index in a range constituted from a lower limit and an upper limit selected as appropriate from the above, with the proviso that the disintegration index is at least 0.05. Specific examples of the range of the disintegration index are 0.05 to 1.5, 0.08 to 1.5, 0.09 to 1.0, 0.1 to 0.9, 0.10 to 0.8, 0.1 to 0.7, 0.1 to 0.6 and 0.1 to 0.5.

Moreover, it is preferable to prepare the freeze-dried composition of the present invention in a non-powder cake-like form by freeze-drying. In the present Invention, 'non-powder-form freeze-dried composition' member a dry solid obtained by freeze-drying a composition liquid containing active ingredients, and is generally called a 'freeze-dried cake'. However, even if cracks appear in the cake, the cake breaks into a plurality of large lumps, or part of the cake breaks into a powder during the freeze-drying process or during subsequent handling, this cake is still included as a non-powder-form freeze-dried composition that is the subject of the present invention, more specifically, as a freeze-dried composition having a non-powder cake like form, provided the effects of the present invention are not impaired.

As described above, the freeze-dried composition of the present invention is prepared by freeze-drying a composition liquid containing ingredients in the non-dissolved form and has a disintegration index of 0.05 or more and a non-powder cake-like form and becomes fine particles having a mean particle diameter of 10 microns or less or a fine particle fraction of 10% or more upon receipt of an air impact having an air speed of at least 1 m/sec and an air flow rate of at least 17 ml/sec, on the basis of properties peculiar to the freeze-dried composition represented by the disintegration index.

A preferable freeze-dried composition is such that, upon receiving the above air impact, the mean particle diameter becomes 10 microns or less and preferably 5 microns or less or a fine particle fraction of 10% or more, preferably 20% or more, more preferably 25% or more, still more preferably 30% or more, and especially more preferably 35% or more.

As described above, the air impact applied to a freeze-dried composition Is not limited, as long as it is generated by air having an air speed of at least 1 m/sec and an air flow rate of at least 17 ml/sec. Specific examples of an air impact include an impact generated by an air having a speed of 1 m/sec or more, preferably 2 m/sec or more, more preferably 5 m/sec or more and a still more preferably 10 m/sec or more, Here, there is no limitation on the upper limit of the air speed, but it is generally 300 m/sec, preferably 250 m/sec, more preferably 200 m/sec and yet more preferably 150 m/sec. The air speed is not limited as long as it is arbitrary selected from the range extending from a lower limit to an upper limit; however, the ranges of 1 to 300 m/sec, 1 to 250 m/sec, 2 to 250 m/sec, 5 to 250 m/sec, 5 to 200 m/sec, 10 to 200 m/sec or 10 to 150 m/sec can be given as examples.

Examples of the air impact include those generated by air having an air flow rate of generally 17 ml/sec or more, preferably 20 ml/sec or more and more preferably 25 ml/sec or more. There is no limitation on the upper limit of the air flow rate; however, the air flow rate is generally 900 L/min, preferably 15 L/sec, more preferably 5 L/sec and yet more preferably 4 L/sec. Especially, 3 L/sec is very preferable. More specifically, the air flow rate is not limited as long as it is selected from the range extending from a lower limit to an upper limit; however, examples of such a range include 17 ml/sec to 15 L/sec, 20 ml/sec to 10 L/sec, 20 ml/sec to 5 L/sec, 20 ml/sec to 4 L/sec, 20 ml/sec to 3 L/sec and 25 ml/sec to 3 L/sec.

In principle, there is no particular limitation on the active ingredients used in the present invention, provided it is a substance having some pharmacological activities (pharmacologically active substance: hereinafter, simply referred to as a drug) that can be used as ingredients for a powdered inhalation for transpulmonary administration; nevertheless, low-molecular-weight drugs and high-molecular-weight drugs can be given as specific examples. Such high-molecular weight drugs include physiologically active substances such as proteins (including peptides or polypeptides), for example, enzymes, hormones, antibodies, etc., nucleic acids (including genes and cDNA), RNA, and the like.

Moreover, regarding the disease targeted by the drug, both whole body treatment and local treatment can be envisaged, depending on the case.

Examples of low-molecular-weight drugs include, for example, hydrocortisone, prednisolone, triamcinolone, dexamethasone, betamethasone, beclometasone, fluticasone, mometasone, budesonide, salbutamol, salmeterol, procaterol, buprenorphine hydrochloride, apomorphine, taxol, and antibiotics such as tobramycin.

Examples of high-molecular-weight drugs (physiologically active substances such as proteins and nucleic acids) include, for example, interferons (α, β, γ), interleukins (for example, interleukin-1, 2, 3, 4, 5, 6, 7, 8, 9, 10, 11, 12, 13, 14, 15, 16, 17, 18, etc.), anti-interleukin-1α antibody, interleukin-1 receptor, interleukin receptor antagonist, interleukin-4 receptor, anti-interleukin-2 antibody, anti-interleukin-6 receptor antibody, interleukin-4 antagonist, interleukin-6 antagonist, anti-interleukin-8 antibody, chemokine receptor antagonist, anti-interleukin-7 receptor, anti-interleukin-7 antibody, anti-interleukin-5 antibody, interleukin-5 receptor, anti-interleukin-9 antibody, interleukin-9 receptor, anti-interleukin-10 antibody, interleukin-10 receptor, anti-interleukin-14 antibody, interleukin-14 receptor, anti-interleukin-15 antibody, interleukin-15 receptor, interleukin-18 receptor, anti-interleukin-18 antibody, erithropoietin (EPO), erithropoletin derivatives, granulocyte colony stimulating factor (G-CSF), granulocyte macrophage colony stimulating factor (GM-CSF), macrophage colony stimulating factor (M-CSF), calcitonin, insulin, insulin derivatives (LisPro, NovoRapid, HOE901, NN-304, etc.), insulintropin, insulin-like growth factor, glucagon, somatostatin and analogs thereof, vasopressin and analogs thereof, amylin, human growth hormone, lutenizing hormone releasing hormone, follicle stimulating hormone, growth hormone releasing factor, parathyroid hormone, endothelial cell growth factor, platelet derived growth factor, keratinocyte growth factor, epidermal growth factor, fibroblast growth factor, brain-derived neurotrophic factor, ciliary neurotrophic factor, tumor necrosis factor (TNF), TNF receptor, TNF inhibitor, transforming growth factor (TGF), hepatocyte growth factor (HGF), nerve growth factor (NGF), blood stem cell growth factor, platelet growth simulator, naturiuretic peptide, blood coagulation factor, blood hepatocyte growth factor (S-CSF), FLT3 ligand, anti-platelet aggregation inhibiting monoclonal antibody, tissue plasminogen activator and derivatives thereof, superoxide dismutase, antisense drugs, immunosuppression agents (for example, cyclosporin, tacrolimus hydrate, etc.), cancer repressor gene p53, cystic fibrosis transmembrane conductance regulator (CFTR) gene, RNA interferance (RNAi), Bridged Nucleic Acid (BNA), α-1 antitrypsin, thrombopoietin (TPO), metastatin, deoxyribonuclease (Dnase), prolactin, oxytocin, thyrotopin releasing hormone (TRH), bactericidal permeability increasing (BPI) protein, and vaccine preparations, for example influenza vaccines, AIDS vaccines, rotavirus vaccines, malaria vaccines and tuberculosis vaccines such as Mtb72f.

One of these active ingredients can be used alone, or two or more can be used in combination. Note that the various peptides above encompass natural polypeptides, gene recombinant polypeptides, chemically synthesized polypeptides and so on.

These active ingredients can be used in free form or in salt form, alternatively, they can be used in a form such that they are bound by various types of hosts. Such hosts are not particularly limited insofar as active ingredients (for example, high-molecular-weight drugs such as proteins and nucleic acids, etc., low-molecular weight drugs) can be bound by various forms of adhesion/presence (adsorption, absorption, clathration, ionic interactions, etc.). Specific examples of hosts include lipid-membrane structures, microcapsules, cyclodextrins, dendrimers, microsperes, nanocapsules, nanosperes, etc. Lipid-membrane structures include liposomes such as single membrane liposomes, multilayer lipospmes, etc.; emulsions such as the O/W-type or W/O/W-type etc., spherical micelles, corded micelles, layer structural substance, etc.

In general, dendrimers are molecules with a three-dimensional form such that molecule chains regularly branch outwardly from a core regularly based on a predetermined rule. Dendrimers generally have a spherical structure with voids for encapsulting drugs therein, and thus can serve as nanocapsules. The following methods are known for encapsulting drugs in dendrimers: (1) utilizing interactions between the dendrimer interior and drugs (hydrophobic interactions, electrostatic interactions, etc.) or (2) forming a dense shell structure at the dendrimer surface to physically entrap drugs (Kenji Kawano: Drug Delivery System, 17-6, 462-470(2002)). SuperFect employed in Examples is composed of activated dendrimer molecules of a predetermined form (Tang. M. X, Redemann, C. T. and Szoka, Jr. F. C: In vitro gene delivery by degraded polyamidoamine dendrimers. Bioconjugate Chem. 7, 703(1996)). These molecules have a structure branching from the center, and have positively charged amines at the branch terminals so as to interact with the (negatively charged) phosphoric acid groups of nucleic acids. SuperFect is endowed with the property of compacting DNA or RNA so that DNA or RNA can be readily introduced into cells.

Preferably, hosts include liposomes, dendrimers, retrovirus vectors, adenovirus vectors, adeno-associated virus vectors, lentivirus, herpes simplex virus vector, HVJ (Sendai Virus)-liposome (for example, HVJ Envelope VECTOR KIT) etc.

Hosts such as lipid-membrane structures or dendrimers, etc. have been widely used for introducing foreign genes into cells. Liposomes for gene transfer and dendrimers for gene transfer can also be used in the present invention in the same manner, and are available commercially.

Particle diameter (geometric mean particle diameter: Dynamic light scattering or Laser diffraction/scattering) of the hosts is not particularly limited insofar as it is 10 μm or less, and 5 μm or less is preferred. In general, liposomes or emulsions, have for example, a particle diameter (geometric mean particle diameter: Dynamic light scattering or Laser diffraction/scattering) of 50 nm to a few micrometers, and spherical micelles have a particle diameter of 5 to 50 nm.

For measuring the geometric mean particle diameter, in general, dynamic light scattering is used for distribution of particles with the size range of several tens of nanometers and laser diffraction/scattering is used for ten or more microns. For distribution of particles with the size in the range of hundreds of nanometers to several microns, either method may be used.

The manner of binding active ingredients (for example, nucleic acids such as genes, etc.) into the hosts is not particularly limited. For example, when a lipid membrane structure is used, active ingredients are adhered to/present in the membrane, the membrane surface, the membrane interior, the lipid layer inside or the lipid layer surface of the membrane structure.

Examples of methods for obtaining the bound forms include the method of adding aqueous solvent to a dried mixture of the host such as a lipid membrane structure, etc., and the active ingredients (genes, etc.), and then emulsifying them with an emulsifier such as a homogenizer or the like; the method of dissolving a host such as a membrane structure with an organic solvent, and evaporating the solvent to obtain a dried substance, and further adding aqueous solvent including genes to the dried substance obtained and emulsifying the mixture; the method of adding aqueous solvent including active ingredients (genes, etc.) to hosts such as membrane structure substances dispersed in the aqueous solvent; and a method for adding aqueous solvent including active ingredients (genes, etc.) to a dried substance obtained by dispersing hosts such as a membrane structural substance into aqueous solvent and then drying them (Japanese Unexamined Published Patent No. 2001-02592).

The size (particle diameter) can be controlled by a method for carrying out extrusion (extrusion-filtration) under high pressure with a membrane filter having the uniform pore diameter, or by a method using an Extruder (Japanese Unexamined Patent Publication No. 1994-238142).

The freeze-dried composition of the present invention is prepared by freeze-drying a composition liquid containing ingredients (including the above-mentioned active ingredients) in the non-dissolved form. In this specification, 'the non-dissolved form' indicates a state where ingredients are neither clearly dissolved nor mixed in a solvent constituting a composition liquid. Such 'non-dissolved form' includes a state where solids in the solvent can be detected by various methods. More specifically, as an example, the case can be mentioned where solids having the geometric mean particle diameter (Dynamic light scattering or Laser diffraction/scattering) of 0.01 μm or more, preferably 0.05 μm or more, more preferably 0.1 μm or more, still more preferably 0.2 μm or more, still further preferably 0.5 μm or more can be detected. According to the object of the present invention, the geometric mean particle diameter (Dynamic light scattering or Laser diffraction/scattering) of these solids are determined so that the upper limit thereof is 20 μm or less, preferably 15 μm or less, more preferably 10 μm or less. More specifically, the 'non-dissolved form' of the present invention includes a state where solids having the geometric mean particle diameter (Dynamic light scattering or Laser diffraction/scattering) having 0.01 to 20 μm, 0.05 to 15 μm, 0.1 to 15 μm, 0.2 to 15 μm, 0.5 to 15 μm, 0.05 to 10 μm, 0.1 to 10 μm, or 0.2 to 10 μm are present in the solvent and can be detected by various methods. The 'non-dissolved form' includes the following examples: a state where ingredients are not completely dissolved into the solvent, and are supersaturated; and a state where ingredients are not dissolved in the solvent, and more specifically, active ingredients which are not dissolved or are hard to dissolve into the solvent are suspended or mudded in the solvent. The non-dissolved form can be typically evaluated by measuring the turbidity of the sample, but can also be evaluated by methods for measuring the particle size distribution of the non-dissolved substances in the solvent with an apparatus for particle size distribution measurement.

In the specification, ingredients in the non-dissolved form specifies not only the case where the active ingredients or the carrier, which will be described later, themselves are not dissolved in the solvent, but also the case where the active ingredients are dissolved in the solvent and bound by a host such as the above-mentioned liposomes, microcapsules, cyclodextrins, dendrimers, etc., while the host such as liposome, etc., is not dissolved in the solvent. The type of ingredients is not particularly limited insofar as the ingredients are in the dissolved form, and may be active ingredients, hosts which are mixed in the composition liquid with active ingredients or another ingredient (which will be described later).

The solvent constituting the composition liquid with the ingredients are not particularly limited, and can include isotonic solutions such as water, physical saline, etc., culture medium, buffer solutions, etc. Organic solvents may be contained in the solvent provided that the end product (freeze-dried composition for transpulmonary administration) adversely affects human body. Such organic solvents include methanol, ethanol, isopropanol, acetone, ethylene glycol, and the like.

The freeze-dried composition of the present invention may comprise the active ingredient alone or the active ingredient and the host, as long as the end products satisfy the above-mentioned disintegration index, or a suitable carrier may be admixed. In the case of using a carrier in addition to the active ingredient, there are no particular limitations on the type and amount of carrier used, so long as the final freeze-dried composition containing the carrier with active ingredients which is prepared by freeze-drying the composition liquid in the non-dissolved form satisfies the following properties (i) to (iii);

(i) has a non-powder cake-like form, (ii) has a disintegration index of 0.05 or more, and (iii) becomes fine particles having a mean particle diameter of 10 microns or less or a fine particle fraction of 10% or more upon receipt of an air impact having an air speed of at least 1 m/sec and an air flow rate of at least 17 ml/sec and the effects of the present invention (making into a fine particle) are attained. Those carriers commonly used for freeze-drying may be used arbitrarily and at desired amounts.

Specific examples of the carrier include hydrophobic amino acids such as valine, leucine, isoleucine and phenylalanine, and salts and amides thereof; hydrophilic amino acids such as glycine, proline, alanine, arginine and glutamic acid, and salts and amides thereof; derivatives of amino acids; and dipeptides, tripeptides or the like having two or more of the same one or different ones of the above-mentioned amino acids, and salts and amides thereof. One of these can be used alone, or two or more can be used in combination. Here, examples of salts of the amino acid or peptide include salts with an alkali metal such as sodium or potassium or an alkaline earth metal such as calcium, and addition salts with an inorganic acid such as phosphoric acid or hydrochloric acid or an organic acid such as sulfonic acid, while examples of amides include L-leucine amide hydrochloride. Moreover, an amino acid other than an α-amino acid can be used in as a carrier. Examples of such an amino acid include β-alanine, γ-aminobutyric acid, homoserine and taurine.

Other examples of carriers include monosaccharides such as glucose; disaccharides such as saccharose, maltose, lactose and trehalose; sugar alcohols such as mannitol; oligosaccharides such as cyclodextrin; polysaccharides such as dextran 40 and pullulan; polyhydric alcohols such as polyethylene glycol; and fatty acid sodium salts such as sodium caprate. One of these carriers may be used alone, or two or more may be used in combination.

Of the above carriers, specific examples of carriers that are preferable for delivering the active ingredient efficiently into the lungs include hydrophobic amino acids such as isoleucine, valine, leucine and phenylalanine, and salts and amides thereof; hydrophobic dipeptides such as leucyl-valine, leucyl-phenylalanine and phenylalanyl-isoleucine; and hydrophobic tripeptides such as leucyl-leucyl-leucine and leucyl-leucyl-valine. Again, one of these may be used alone, or two or more may be used in combination.

In the case of interferon γ, it is preferable to use basic amino acids, and salts and amides thereof, basic dipeptides and basic tripeptides in combination of hydrophobic amino acids, and salts and amides thereof, hydrophobic dipeptides, and hydrophobic tripeptides in view of making into fine particles and preparation stability. The basic amino acids include arginine, lysine, histidine and salts thereof. The combination of phenylalanine and arginine hydrochloride or the combination of phenylalanine, leucine and arginine hydrochloride is preferable.

There are no particular limitations on the proportion of the active ingredients (drug(s)) mixed into the freeze-dried composition; nevertheless, examples of the content are 20 mg or less, preferably 10 mg or less, more preferably 5 mg or less, yet more preferably 2 mg or less, particularly preferably 1 mg or less.

Moreover, there are no particular limitations on the mixing proportion of the carrier(s), provided the final freeze-dried composition satisfies the above-mentioned properties (i) to (iii); nevertheless, as a guideline, per 100 wt % of the freeze-dried composition, the range is generally from 0.1 to less than 100 wt %, preferably from 1 to less than 100 wt %, more preferably from 10 to less than 100 wt %, particularly preferably from 20 to less than 100 wt %.

Note that, in addition to the above-mentioned components, the freeze-dried composition that is the subject of the present invention may have mixed therein various additives, for example for stabilizing the active ingredient(s) in solution before drying, for stabilizing the active ingredient(s) after drying, or for preventing the active ingredient(s) from sticking to the vessel, provided that the above-mentioned properties (i) to (iii) is satisfied and the effects of the present invention are not impaired. For example, the freeze-dried composition may contain human serum albumin, inorganic salts, surfactants, buffering agents and so on. A wide range of surfactants can be used, regardless of whether they are anionic surfactants, cationic surfactants or nonionic surfactants, provided that they are surfactants that are generally used in medicines. Preferable examples are nonionic surfactants such as polyoxyethylene sorbitan fatty acid esters (for example Tween type surfactants) and sorbitan trioleate.

The method of freeze-drying a composition liquid which contains such active ingredients and other ingredients is not particularly limited, and a freeze-drying method commonly used in preparing a usual freeze-dried preparation (freeze-dried composition), such as an injection which is dissolved at the time of usage can be employed. There is no limitation, and a quick freeze-drying method, if required, may be carried out by appropriately varying freeze-drying conditions.

The freeze-dried composition of the present invention can be pulverized into fine particles suitable for transpulmonary administration by applying an air impact of a predetermined value. Thus, the freeze-dried composition of the present invention can be served as a so-called pre-preparation for a powder preparation for transpulmonary administration, which is suitable for providing a powder preparation for transpulmonary administration (a freeze-dried composition for providing a powder preparation for transpulmonary administration).

The freeze-dried composition for use in the present invention encompasses the specific embodiments defined in the following items:

101. A freeze-dried composition for transpulmonary administration having the following properties (i) to (iii):

(i) has a non-powder cake-like form, (ii) has a disintegration index of 0.05 or more, and (ii) becomes fine particles having a mean particle diameter of 10 microns or less or a fine particle fraction of 10% or more upon receipt of an air impact having an air speed of at least 1 m/sec and an air flow rate of at least 17 ml/sec.

102. The freeze-dried composition according to item 101, wherein the disintegration index is 0.05 to 1.5.

103. The freeze-dried composition according to item 101 becoming fine particles having a mean particle diameter of 10 microns or less or a fine particle fraction of 10% or more upon receipt of an air impact having an air speed of at least 2 m/sec and an air flow rate of at least 17 ml/sec.

104. The freeze-dried composition according to item 101 becoming fine particles having a mean particle diameter of 10 microns or less or a fine particle fraction of 10% or more upon receiving an air impact having an air speed in a range of 1 to 300 m/sec and an air flow rate of at least 17 ml/sec.

105. The freeze-dried composition according to item 101, becoming fine particles having a mean particle diameter of 10 microns or less or a fine particle fraction of 10% or more upon receipt of an air impact having an air speed of at least 1 m/sec and an air flow rate of at least 20 ml/sec.

106. The freeze-dried composition according to item 101, becoming fine particles having a mean particle diameter of 10 microns or less or a fine particle fraction of 10% or more upon receiving an air impact having an air speed of at least 1 m/sec and an air flow rate in a range of 17 ml/sec to 15 L/sec.

107. The freeze-dried composition according to item 101, becoming fine particles having a mean particle diameter of 5 microns or less or a fine particle fraction of 20% or more upon receiving an air impact.

108. The freeze-dried composition according to item 101, containing a low-molecular-weight drug as an active ingredient.

109. The freeze-dried composition according to item 101, containing a high-molecular-weight drug such as a protein, a peptide or the like as an active ingredient.

110. The freeze-dried composition according to item 109, containing a nucleic acid as an active ingredient with held in a holder.

111. The freeze-dried composition according to item 108, containing a low-molecular-weight drug as the active ingredient, and at least one selected from the group consisting of amino acids, dipeptides, tripeptides, and saccharides as a carrier.

112. The freeze-dried composition according to item 109, containing a high-molecular-weight drug such as a protein, a peptide or the like as the active ingredient, and at least one selected from the group consisting of amino acids, dipeptides, tripeptides, and saccharides as a carrier.

113. The freeze-dried composition according to item 111, containing a low-molecular-weight drug as the active ingredient, and at least one selected from the group consisting of hydrophobic amino acids, hydrophobic dipeptides, and hydrophobic tripeptides as the carrier.

114. The freeze-dried composition according to item 112, characterized by containing a high-molecular-weight drug such as a protein, a peptide or the like as the active ingredient, and at least one selected from the group consisting of hydrophobic amino acids, hydrophobic dipeptides, and hydrophobic tripeptides as the carrier.

115. The freeze-dried composition according to item 101, being a water-soluble composition.

116. The freeze-dried composition according to item 101, containing a single dose of an active ingredient.

117. The freeze-dried composition according to item 101, being a freeze-dried composition for transpulmonary administration prepared by freeze-drying a composition liquid containing ingredients in the non-dissolved form and has the following properties (i) to (iii):
  (i) has a non-powder cake-like form,
  (ii) has a disintegration index in a range of 0.05 to 1.5, and
  (iii) becomes fine particles having a mean particle diameter of 10 microns or less or a fine particle fraction of 10% or more upon receiving an air impact having an air speed in a range of 1 to 300 m/sec and an air flow rate in a range of 17 ml/sec to 15 L/sec.

118. The freeze-dried composition according to item 117, wherein the air speed is 1 to 250 m/sec.

119. The freeze-dried composition according to item 117, wherein the air flow rate is 20 ml/sec to 10 L/sec.

(2) Method of Manufacturing a Dry Powdered Preparation

Moreover, the present invention relates to a method of manufacturing a dry powdered preparation comprising fine particles with a particle diameter suitable for transpulmonary administration (dry powdered preparation for transpulmonary administration) by inhalation, by making a freeze-dried composition that has been housed in a non-powder form in a vessel into fine particles. The manufacturing method can be implemented in the vessel housing the non-powder form freeze-dried composition by applying a predetermined air impact.

Specifically, the method of manufacturing the dry powder preparation of the present invention can be carried out by applying an air impact having an air speed of at least 1 m/sec and an air flow rate of at least 17 ml/sec to the non-powder form freeze-dried composition of the present invention having a disintegration index of at lest 0.05 which is prepared by freeze-drying the composition liquid containing ingredients in the non-dissolved form as described in detail in the above section (1). Thereby, the non-powder form freeze-dried composition can be made into a dry powdered preparation having a mean particle diameter of 10 microns or less, preferably 5 microns or less or a fine particle fraction of 10% or more, preferably 20% or more, more preferably 25% or more, still more preferably 30% or more, and in particular 35% or more.

As used herein, the mean particle diameter of fine particles indicates a mean particle diameter usually adopted in the industry relating to inhalants. Specifically, the mean particle diameter is not a geometric mean particle diameter, but an aerodynamic mean particle diameter (mass median aerodynamic diameter, MMAD) unless otherwise specified. The aerodynamic mean particle diameter can be measured by a conventional method. For example, the mass median aerodynamic diameter can be measured using a dry particle size distribution meter fitted with an Aerobreather, which is an artificial lung model (manufactured by Amherst Process Instrument, Inc., USA), a twin impinger (G. W. Hallworth and D. G. Westmoreland: J. Pharm. Pharmacol., 39, 966-972 (1987), U.S. Pat. No. 6,153,224), a multi-stage liquid impinger, a Marple-Miller impactor, an Andersen cascade impactor or the like. Moreover, B. Olsson et al. have reported that delivery of the particles into the lungs increases at the proportion of particles having a mass median aerodynamic diameter of 5 μm or less increases (B. Olsson et al.: Respiratory Drug Delivery V. 273-281(1996)). The fine particle fraction, fine particle dose or the like as measured by a twin impinger, a multi-stage liquid impinger, a Marple-Miller impactor, an Andersen cascade impactor or the like acts as a method of estimating the amount that can be delivered into the lungs.

The manufacturing method of the present invention can be implemented by filling into a vessel the composition liquid containing ingredients in the non-dissolved form, generating the non-powder form freeze-dried composition by freeze-drying the composition liquid in the non-dissolved form, and applying the air impact defined in the above to the generated freeze-dried composition by introducing air into the vessel housing the generated composition. In this case, freeze-drying process and a process for making a powder into a preparation can be carried out using the same vessel, which can avoid a loss or contamination resulting from subdividing.

The method of applying the air impact to the freeze-dried composition is not limited; however, a dry powder inhaler which will be described in the section (3) below is preferably used.

The method of manufacturing the dry powdered preparation for transpulmonary administration of the present invention is also characterized in that a patient administering the dry powdered preparation can prepare by him/herself the powdered preparation for transpulmonary administration at the time of use (inhalation) by making the freeze-dried composition housed in a vessel into fine particles having a particle diameter suitable for transpulmonary administration.

The method of manufacturing a dry powdered preparation of the present invention encompasses the specific embodiments defined in the following items:

201. A method of manufacturing a dry powdered preparation for transpulmonary administration, comprising:

introducing air into a vessel to apply to a freeze-dried composition an air impact having an air speed of at least 1 m/sec and an air flow rate of at least 17 ml/sec using a device capable of applying said air impact to the freeze-dried composition in the vessel, thereby making said freeze-dried composition into fine particles having a mean particle diameter of 10 microns or less or a fine particle fraction of 10% or more;

the freeze-dried composition prepared by freeze-drying the composition liquid containing Ingredients in the non-dissolved form and having the following properties:

(i) has a non-powder cake-like form, (ii) has a disintegration index of 0.05 or more, and (iii) becomes fine particles having a mean particle diameter of 10 microns or less or a fine particle fraction of 10% or more upon receipt of the air impact.

202. The method of manufacturing a dry powdered preparation for transpulmonary administration according to item 201, wherein the freeze-dried composition housed in the vessel containing a single dose of an active ingredient.

203. The method of manufacturing a dry powdered preparation for transpulmonary administration according to item 201, wherein the fine particles prepared have a mean particle diameter of 5 microns or less or a fine particle fraction of 20% or more.

204. The method of manufacturing a dry powdered preparation for transpulmonary administration according to item 201, wherein the disintegration index of the freeze-dried composition is in a range of 0.05 to 1.5.

205. The method of manufacturing a dry powdered preparation for transpulmonary administration according to item 201, wherein the freeze-dried composition contains a low-molecular-weight drug as the active ingredient.

206. The method of manufacturing a dry powdered preparation for transpulmonary administration according to item 201, wherein the freeze-dried composition contains a high-molecular-weight drug such as a protein, a nucleic acid or the like as the active ingredient.

207. The method of manufacturing a dry powdered preparation for transpulmonary administration according to item 201, wherein the freeze-dried composition contains a nucleic acid with held in the holder.

208 The method of manufacturing a dry powdered preparation for transpulmonary administration according to item 205, wherein the freeze-dried composition contains a low-molecular-weight drug as the active ingredient, and at least one selected from the group consisting of amino acids, dipeptides, tripeptides, and saccharides as a carrier.

209. The method of manufacturing a dry powdered preparation for transpulmonary administration according to item 206, wherein the freeze-dried composition contains a high-molecular-weight drug such as proteins, a nucleic acid or the like as the active ingredient, and at least one selected from the group consisting of amino acids, dipeptides, tripeptides, and saccharides as a carrier.

210. The method of manufacturing a dry powdered preparation for transpulmonary administration according to item 208, wherein the freeze-dried composition contains a low-molecular-weight drug as the active ingredient, and at least one selected from the group consisting of hydrophobic amino acids, hydrophobic dipeptides, and hydrophobic tripeptides as the carrier.

211. The method of manufacturing a dry powdered preparation for transpulmonary administration according to item 209, wherein the freeze-dried composition contains a high-molecular-weight drug such as proteins, a nucleic acid or the like as the active ingredient, and at least one selected from the group consisting of hydrophobic amino acids, hydrophobic dipeptides, and hydrophobic tripeptides as the carrier.

212. The method of manufacturing a dry powdered preparation for transpulmonary administration according to item 201, wherein the freeze-dried composition is a water-soluble composition.

213. The method of manufacturing a dry powdered preparation for transpulmonary administration according to item 201, being a method of making the freeze-dried composition into fine particles in a vessel having a volume of 0.2 to 50 ml.

214. The method of manufacturing a dry powdered preparation for transpulmonary administration according to item 201, carried out by using a device having a member capable of applying an air impact having an air speed of at least 2 m/sec and an air flow rate of at least 17 ml/sec to the freeze-dried composition in the vessel, and introducing air having the air impact into the vessel housing the freeze-dried composition.

215. The method of manufacturing a dry powdered preparation for transpulmonary administration according to item 201, carried out by using a device having a member capable of applying an air impact having an air speed in a range of 1 to 300 m/sec and an air flow rate of at least 17 ml/sec to the freeze-dried composition in the vessel, and introducing air having the air impact into the vessel housing the freeze-dried composition.

216. The method of manufacturing a dry powdered preparation for transpulmonary administration according to item 201, carried out by using a device having a member capable of applying an air impact having an air speed of at least 1 m/sec and an air flow rate of at least 20 ml/sec to the freeze-dried composition in the vessel, and introducing air having the air impact into the vessel housing the freeze-dried composition.

217. The method of manufacturing a dry powdered preparation for transpulmonary administration according to item 201, carried out by using a device having a member capable of applying an air impact having an air speed of at least 1 m/sec and an air flow rate in a range of 17 ml/sec to 15 L/sec to the freeze-dried composition in the vessel, and introducing air having the air impact into the vessel housing the freeze-dried composition.

218. The method of manufacturing a dry powdered preparation for transpulmonary administration according to item 201, characterized by making the freeze-dried composition into fine particles using the dry powder Inhaler of item 301 or 302 shown in the section of (3) Dry powder inhaler as the device.

219. The method of manufacturing a powdered preparation for transpulmonary administration according to Item 218, characterized by making the freeze-dried composition into fine particles using the dry powder inhaler according to item 309 shown in the section of (3) Dry powder inhaler as the device.

220. The method of manufacturing a powdered preparation for transpulmonary administration according to item 218, being a method of manufacturing a dry powdered preparation in which the freeze-dried composition is made into fine particles using the dry powder inhaler according to item 301 shown in the section of (3) Dry powder inhaler, wherein the amount of air jetted into said vessel each time using the dry powder inhaler is 5 to 100 ml.

221. The method of manufacturing a powdered preparation for transpulmonary administration according to item 417, being a method of manufacturing a dry powdered preparation in which the freeze-dried composition is made into fine particles using the dry powder inhaler of item 302 shown in the section of (3) Dry powder inhaler, wherein the flow rate of air inhalation from the inhalation port using the dry powder inhaler is 5 to 300 L/min.

222. The method of manufacturing a dry powdered preparation for transpulmonary administration according to item 201, comprising:

introducing air into a vessel to apply to a freeze-dried composition an air impact having an air speed in a range of 1 to 300 m/sec and an air flow rate in a range of 17 ml/sec to 15 L/sec using a device capable of applying said air impact to the freeze-dried composition in the vessel, thereby making said freeze-dried composition into fine particles having a mean particle diameter of 10 microns or less or a fine particle fraction of 10% or more;

the freeze-dried composition prepared by freeze-drying the composition liquid containing ingredients in the non-dissolved form and having the following properties:
  (i) has a non-powder cake-like form,
  (ii) has a disintegration index in a range of 0.05 to 1.5, and
  (iii) becomes fine particles having a mean particle diameter of 10 microns or less or a fine particle fraction of 10% or more upon receipt of the air impact.

223. The method of manufacturing a dry powdered preparation for transpulmonary administration according to item 222, wherein the freeze-dried composition housed in the vessel contains a single dose of an active ingredient.

224. The method of manufacturing a dry powdered preparation for transpulmonary administration according to item 222, wherein the air speed is 1 to 250 m/sec.

225. The method of manufacturing a dry powdered preparation for transpulmonary administration according to item 222, wherein the air flow rate is 20 ml/sec to 10 L/sec.

(3) Dry Powder Inhaler

The dry powder inhaler used suitably for manufacturing a dry powdered preparation for transpulmonary administration of the present invention is a device used for breaking down a freeze-dried preparation (freeze-dried composition) that has been housed in a non-powder form in a vessel Into fine particles in the vessel, and further allowing a user to inhale the dry powdered preparation.

By comprising ① a member capable of applying an air impact to the non-powder form freeze-dried composition in a degree such that the freeze-dried composition can be pulverized into fine particles, and ② a member capable of administering to a user by inhalation the powder-form freeze-dried composition that has been made into fine particles, the device can carry out both breaking down of the freeze-dried composition into fine particles and administration of the powdered composition to a user by inhalation. Note that the member ① can also appreciated as a member for introducing air having the above-mentioned air impact into the vessel housing the freeze-dried composition. Moreover, the member ② can also appreciated as a member for discharging out of the vessel the powdered preparation that has been made into fine particles in the vessel. In a dry powder inhalation system of the present invention, as long as the device comprises these members, either a conventional publicly-known device or a device which will be developed in the future can also be used.

Specifically, the member ① can be realized by introducing air capable of applying an air impact as above into the vessel housing the freeze-dried composition. Note that the member ① can be altered into a member capable of applying an air impact having an air speed of at least 1 m/sec and an air flow rate of at least 17 ml/sec to the freeze-dried composition in the vessel. By using the member ② or via this member, the dry powdered preparation, which has been prepared into a form suitable for transpulmonary administration, can be administered by inhalation to the user such as patient. Note that, for example a chamber or a flow path such that the composition is made into fine particles or scattered may be further provided in the member ②.

The device in question encompasses jet type dry powder inhalers as in (a) below and self-inhaling type dry powder inhalers as in (b) below.

(a) Jet type dry powder inhaler: Active powder inhaler (a-1) A dry powder inhaler used in the making into fine particles and inhalation of a freeze-dried composition that has been housed in a non-powder form in a vessel, comprising a needle part having an air jet flow path, a needle part having a discharge flow path, air pressure-feeding member for feeding air into the air jet flow path of the needle part, and an inhalation port that communicates with the discharge flow path, and being constituted such that a stopper that seals up the vessel is pierced by the needle parts, thus communicating the air jet flow path and the discharge flow path with the inside of the vessel, and air is jetted into the vessel from the air jet flow path using the air pressure-feeding member, thus breaking down the freeze-dried composition into fine particles by the impact of the jetted air, and discharging the fine particles obtained out from the inhalation port via the discharge flow path.

(a-2) The dry powder inhaler described in (a-1) above, being constituted such that the air pressure-feeding member is manually operated and comprises a bellows body having an intake port equipped with an intake valve and a discharge port equipped with a discharge valve, and by contracting the bellows body and thus opening the discharge valve in a state in which the intake valve is closed, air in the bellows body is pressure-fed into the vessel through the air jet flow path of the needle part which communicates with the discharge port, and by expanding the bellows body through an elastic restoring force in a state in which the discharge valve is closed and the intake valve is open, air is introduced into the bellows body.

(a-3) The dry powder inhaler described in (a-1) or (a-2) above, in which the air jet flow path and the discharge flow path are formed in a single needle part.

(b) Self-inhaling type dry powder inhaler: Passive powder inhaler (b-1) A dry powder inhaler used for inhaling fine particles obtained by breaking down a freeze-dried composition that has been housed in a non-powder form in a vessel, comprising a needle part having a suction flow path, a needle part having an air introduction flow path, and an inhalation port that communicates with the suction flow path, and being constituted such that, in a state in which a stopper that seals up the vessel has been pierced by the needle parts, through the inhalation pressure of a user, air in the vessel is inhaled from the inhalation port, and at the same time outside air flows into the vessel, which is now at a negative pressure, through the air introduction flow path, and as a result the freeze-dried composition is broken down into fine particles by the impact of the air flowing in, and the fine particles obtained are discharged from the inhalation port through the suction flow path.

(b-2) The dry powder inhaler described in (b-1) above, being constituted such that most part of the freeze-dried composition is made into fine particles and discharged from the inhalation port through one inhalation of the user.

(b-3) The dry powder inhaler described in (b-1) or (b-2) above, in which the suction flow path and the air introduction flow path are formed in a single needle part.

The member for introducing air into the vessel (member ① mentioned above) may be a member for introducing air from the outside at normal pressure. It is not necessary to use compressed air from a jet mill or the like. There are no limitations on the member for introducing air from the outside. For example, in the case where the jet type dry powder inhaler (active powder inhaler) described above is used, a member for artificially introducing external air into the vessel by jetting can be employed. In the case where the self-inhaling type dry powder inhaler is used, a member for naturally introducing outside air into the vessel by suction through negative pressure formed in the vessel when the user inhales can be employed. Moreover, in the former case, i.e. in the jet type dry powder inhaler, the method of introducing external air into the vessel by jetting artificially may be manual or may be a method that is carried out automatically using a machine.

The dry powder inhaler of the present invention, regardless of the type of the inhaler, whether it is an active powder inhaler or a passive powder inhaler, is capable of breaking down the freeze-dried composition that has been stored in non-powder form in the vessel into fine particles using an impact (jet pressure) of external air introduced into (flowing into) the vessel by the air introduction member.

For example, a vessel, used for freeze-drying can be used here, with no limitations on the material, shape etc. As the material, a plastic mainly including a polyolefin such as polyethylene, polypropylene or polystyrene, glass, aluminum and the like can be given as examples. Moreover, as the shape, a circular cylinder, a cup shape, and a polygonal prism (polygonal pyramid) such as a triangular prism (triangular pyramid), a square prism (square pyramid), a hexagonal prism (hexagonal pyramid) or an octagonal prism (octagonal pyramid) can be given as examples.

To obtain the effects efficiently, the volume of the vessel housing the freeze-dried composition is in a range of 0.2 to 50 ml, preferably 0.2 to 25 ml and more preferably 1 to 15 ml. Moreover, it is desirable to be used the trunk inside diameter of the vessel be 2 to 100 mm, preferably 2 to 75 mm, more preferably 2 to 50 mm.

Moreover, the amount of the freeze-dried composition housed in the vessel is preferably an amount containing a unit dose (single dose) or a plurality of doses, specifically 2 to 3 doses, of the active ingredient. More preferably, it is an amount containing a unit dose (single dose) of the active ingredient. Moreover, the specific amount of the freeze-dried composition will vary according to the type and content of the active ingredient contained in the freeze-dried composition, and is selected as appropriate from amounts that can be inhaled, with there being no particular limitation; nevertheless, the amount is generally 30 mg or less, preferably 20 mg or less, more preferable 10 mg or less, particularly preferably 5 mg or less.

Moreover, the air impact generated by the outside air introduced into the vessel is stipulated through the air flow rate at which air flows into the vessel through at least one or a plurality of inhalations of a person or the air speed thus generated. There is no particular limitation on introducing external air with an air flow rate or air speed greater than this, except of course that the durability of the vessel is a limitation. Generally the air flow rate for one inhalation of a person is 5 to 300 L/min, more specifically 10 to 200 L/min. Moreover, in the case of an dry powder inhaler, a device can be used such that the amount of air jetted each time is 5 to 100 ml, preferably 10 to 50 ml. Preferably, adjustment can be carried out such that an air impact generated through an air speed of at least 1 m/sec is applied to the surface of the freeze-dried composition filled in the vessel. A more preferable air impact is an impact generated by an air speed of at least 2 m/sec, a yet more preferable one is an impact generated by an air speed of at least 5 m/sec, and a still more preferable one is an impact generated by an air speed of at least 10 m/sec. Here, there is no particular limitation on the upper limit of the air impact, but an impact generated by an air speed of 300 m/sec can be given as an example. The upper limit is preferably an impact generated through an air speed 250 m/sec, more preferably an impact generated through an air speed 200 m/sec, yet more preferably an impact generated through an air speed 150 m/sec.

There is no particular limitation on the air impact as long as it is generated by air having an air speed arbitrarily selected from the range extending from a lower limit to an upper limit. Specific examples are impacts generated through an air speed in a range of 1 to 300 m/sec, 1 to 250 m/sec, 2 to 250 m/sec, 5 to 250 m/sec, 5 to 200 m/sec, 10 to 200 m/sec or 10 to 150 m/sec.

Here, the speed of the air applied to the freeze-dried composition can be measured as follows. That is, with the jet type dry powder inhaler shown later as Embodiment 1, a mechanism is adopted in which air stored in a bellows body 10 is forcibly introduced onto the freeze-dried composition (cakelike freeze-dried composition: hereinafter also referred to as 'freeze-dried cake') that has been filled into the vessel from an air jet flow path 3, thus applying an air impact, and discharging the resulting fine particles from a discharge flow path 4. In this case, the flow rate of the air flowing through the air jet flow path 3 can be calculated by dividing the amount of air stored in the bellows body 10 by the time over which the air is fed into the vessel. Next, by dividing this air flow rate by the cross-sectional area of a path to introduce air into the vessel such as the air jet flow path 3, the air speed at which the impact is applied to the freeze-dried composition (freeze-dried cake) can be calculated.

$$\text{Air speed(cm/sec)} = \text{air flow rate (ml=cm}^3\text{/sec)} \div \text{cross-sectional area of air introduction flow path (cm}^2\text{)}$$

Specifically, in the case for example of a jet type dry powder inhaler designed such that the bore of the air jet flow path 3 is 1.2 mm, the bore of the discharge flow path is 1.8 mm, and the amount of air stored in the bellows body 10 is about 20 ml, in the case that the amount of air of about 20 ml stored in the bellows body 10 is forcibly introduced onto the freeze-dried composition in the vessel from the air jet flow path 3 in about 0.5 seconds, the air flow rate becomes about 40 ml/sec. Dividing this value by the cross-sectional area of the air introduction flow path (the air jet flow path) (0.06×0.06×3.14=0.0113 cm$^2$), gives 3,540 cm/sec. The air speed is thus about 35 m/sec.

Moreover, with the self-inhaling type dry powder inhalers shown later as Embodiments 2, 3 and 4, a mechanism is adopted in which air flowing in from an air introduction flow path 17 applies an impact to the freeze-dried cake, and then the resulting fine particles are discharged from a suction flow path 16; the bores of the air introduction flow path 17 and the suction flow path 16 thus stipulate the flow rate of the air flowing through the paths. The air speed applied to the freeze-dried composition in the vessel can thus be calculated by measuring the flow rate of the air flowing through the air introduction flow path 17 and dividing this by the cross-sectional area of the air introduction flow path 17.

Air speed (cm/sec)=air flow rate (ml=cm$^3$/sec)+cross-sectional area of air introduction flow path 17 (cm$^2$)

Specifically, the flow rate of the air flowing through the air introduction flow path 17 can be measured by installing the dry powder inhaler including the vessel in the slot part of apparatus A (a twin impinger: manufactured by Copley, UK) as mentioned in the European Pharmacopoeia (Third Edition Supplement 2001, p 113-115), and using a flow meter (KOFLOC DPM-3).

For example, with a self-inhaling type dry powder inhaler designed such that the bore of the air introduction flow path 17 is 1.99 mm and the bore of the suction flow path is 1.99 mm, in the case that the air flow rate flowing through the air introduction flow path 17 measured using the flow meter (KOFLOC DPM-3) was 17.7 L/min, i.e. 295 ml/sec, the air speed can be obtained by dividing this value by the cross-sectional area of the air introduction flow path 17 (0.0995×0.0995×3.14=0.0311 cm$^2$) (9,486 cm/sec, i.e. 95 m/sec).

Moreover, at least 17 ml/sec can be given as an example of the flow rate of the air applied to the freeze-dried composition filled in the vessel. The air flow rate is preferably at least 20 ml/sec, more preferably at least 25 ml/sec. Here there is no particular limitation on the upper limit of the air flow rate, but an example of 900 L/min can be given. This upper limit is preferably 15 L/sec, more preferably 10 L/sec, yet more preferably 5 L/sec, still more preferably 4 L/sec, particularly preferably 3 L/sec. Specifically, the flow rate should be in a range constituted from a lower limit and an upper limit selected as appropriate from the above, with there being no particular limitation; nevertheless, 17 ml/sec to 15 L/sec, 20 ml/sec to 10 L/sec, 20 ml/sec to 5 L/sec, 20 ml/sec to 4 L/sec, 20 ml/sec to 3 L/sec, and 25 ml/sec to 3 L/sec, can be given as examples of the range.

Moreover, as a member for raising the impact pressure of the air introduced from the outside, the dry powder inhaler used in the present invention can have a mamber for discharging air from a discharge port, as explained in detail below, preferably with a small bore, of a flow path close to the freeze-dried composition housed at the bottom of the vessel, for example a needle part having an air introduction flow path or an air jet flow path as described later in the embodiments. Regarding the bore of the discharge port of the flow path, the preferable range varies according to the size of the vessel and so on, with there being no particular limitations; nevertheless, the bore can be in a range of 0.3 to 10 mm, preferably 0.5 to 5 mm, more preferably 0.8 to 5 mm, much more preferably 1 to 4 mm.

The freeze-dried composition housed in a non-powder form in the vessel can be made into fine particles by introducing air into the vessel. Here, the extent of making into fine particles should be such that the particle diameter is suitable for transpulmonary administration; a particle diameter of 10 µm or less, preferably 5 µm or less, can be given as an example.

The dry powder inhaler for use in the present invention encompasses the specific embodiments defined in the following items:

300. A dry powder inhaler for transpulmonary administration used for making a freeze-dried composition that has been housed in non-powder form in a vessel into fine particles by an air impact, and administering the resulting fine particles to a user by inhalation.

301. The dry powder inhaler for transpulmonary administration according to item 300, being a device used for making a freeze-dried composition that has been housed in non-powder form in a vessel into fine particles, and administering the resulting fine particles to a user by inhalation, comprising a needle part having an air jet flow path, a needle part having a discharge flow path, air pressure-feeding member for feeding air into the air jet flow path of said needle part, and an inhalation port that communicates with the discharge flow path of said needle part, and characterized by being constituted such that a stopper that seals up said vessel is pierced by said needle parts, thus communicating the air jet flow path and the discharge flow path with the inside of said vessel, and air is jetted into said vessel through said air jet flow path using said air pressure-feeding member, thus pulverizing said freeze-dried composition into fine particles by the impact of the jetted air, and discharging the fine particles obtained from the inhalation port via said discharge flow path.

302. The dry powder inhaler for transpulmonary administration according to item 300, being a device used for pulverizing a freeze-dried composition that has been housed in non-powder form in a vessel into fine particles, and administering the resulting fine particles to a user by inhalation, comprising a needle part having a suction flow path, a needle part having an air introduction flow path, and an inhalation port that communicates with said suction flow path, and characterized by being constituted such that, in a state in which a stopper sealing up said vessel has been pierced by said needle parts, through the inhalation pressure of the user, air in said vessel is inhaled from said inhalation port, and at the same time outside air flows into said vessel, at a negative pressure, through said air introduction flow path, and as a result said freeze-dried composition is pulverized into fine particles by the impact of the air flowing in, and the fine particles obtained are discharged from the inhalation port through said suction flow path.

303. The dry powder inhaler for transpulmonary administration according to item 301, characterized by being constituted such that said freeze-dried composition is pulverized into fine particles and discharged from said inhalation port through jetting air into said vessel once.

304. The dry powder inhaler for transpulmonary administration according to item 301, characterized by being constituted such that said freeze-dried composition is pulverized into fine particles, such that the mean particle diameter is 10 microns or less or the fine particle fraction is 10% or more, and discharged from said inhalation port through jetting air into said vessel.

305. The dry powder inhaler for transpulmonary administration according to item 301, wherein said air jet flow path and said discharge flow path are formed in a single needle part.

306. The dry powder inhaler for transpulmonary administration according to item 302, characterized by being constituted such that said freeze-dried composition is pulverized into fine particles and discharged from said inhalation port through one inhalation of the user.

307. The dry powder inhaler for transpulmonary administration according to item 302, characterized by being constituted such that said freeze-dried composition is pulverized into fine particles, such that the mean particle diameter is 10 microns or less or the fine particle fraction is 10% or more, and discharged from said inhalation port through inhalation of the user.

308. The dry powder inhaler for transpulmonary administration according to item 302, wherein said suction flow path and said air introduction flow path are formed in a single needle part.

309. The dry powder inhaler for transpulmonary administration according to item 308 comprising:

a holder part for holding a vessel that is sealed up with a stopper and houses a freeze-dried composition in a non-powder cake-like form that will be made into fine particles upon receiving an air impact, a member for applying an air impact to said freeze-dried composition in said vessel, and sucking said freeze-dried composition in a powder-form that has been made into fine particles by the air impact out from said vessel, a needle part having a suction flow path for sucking said freeze-dried composition out from said vessel, and an air introduction flow path for introducing outside air into said vessel, a suction port that communicates with said suction flow path of said needle part, a guide part for guiding said holder part in the axial direction of said needle part, a holder operating part that has a mechanism part for, when said vessel is held by said holder part, advancing the vessel towards a needle tip of said needle part to pierce the stopper of the vessel with said needle tip, and retreating the vessel from said needle tip to separate the stopper of the vessel from said needle tip, and an operator that operates the mechanism part, and is constituted such that said operating member can be operated with a force smaller than the force necessary for the mechanism part to pierce the stopper of the vessel with said needle part, and a housing that supports said needle part and is for providing said suction port, said guide part and said holder operating part, and constituted such that, in a state in which said stopper has been pierced by said needle part to communicate the suction flow path and the air introduction flow path of said needle part with the inside of said vessel and position the tip of the air introduction flow path at said freeze-dried composition, through the inhalation pressure of a user, air in said vessel is inhaled from said suction port, and air is made to flow into said vessel through the air introduction flow path, thus applying an air impact to the freeze-dried composition in said vessel.

310. The dry powder inhaler for transpulmonary administration according to Item 309, characterized in that said housing is formed in a tubular shape, said suction port is formed at a tip part of the housing, a housing chamber for housing said vessel via said holder is formed in said housing, said needle part is disposed in said housing such that said needle tip points towards said housing chamber, and an introduction port for introducing outside air that communicates with the air introduction flow path of said needle part is provided in a wall of said housing, and the dry powder inhaler is constituted such that said holder part is advanced and retreated in the axial direction of said housing in said housing chamber using said holder operating part.

311. The dry powder inhaler for transpulmonary administration according to item 310, characterized in that said housing is formed from a housing main body having a removal/insertion port for said vessel formed therein in a position in which said holder part is retreated, and a lid for said removal/insertion port that is connected to said housing main body by a hinge, and the dry powder inhaler is constituted such that said holder operating part has said mechanism part which advances said holder part towards the needle tip of the needle part when said lid is pushed down to close said removal/insertion port, and retreats said holder part away from said needle tip when said lid is lifted up to open said removal/insertion port, and said lid is used as the operating member of said mechanism part.

(4) Dry Powder Inhalation System for Transpulmonary Administration

The dry powder inhalation system for transpulmonary administration of the present invention is a system that combines a freeze-dried composition having a composition such that, by applying an air impact to the freeze-dried composition which exists in a non-powder form having been freeze-dried in a vessel and not subjected to processing such as pulverization, the freeze-dried composition can be made into fine particles having a mean particle diameter of 10 microns or less or a fine particle fraction of 10% or more in the vessel, and a inhaling device comprising prescribed member. According to this dry powder inhalation system for transpulmonary administration, a user him/herself can prepare the freeze-dried composition which has been provided in a non-powder form into a powdered preparation comprising fine particles having a mean particle diameter of 10 microns or less or a fine particle fraction of 10% or more, which is a preparation suitable for transpulmonary administration, at the time of use (the time of inhalation), and administer (take) the powdered preparation.

To obtain the effects of the dry powder inhalation system for transpulmonary administration effectively, it is important to select the composition of the freeze-dried composition, the inhaling device, the vessel and so on appropriately.

It is preferable to use a freeze-dried composition which is prepared by freeze-drying a composition liquid containing ingredients in the non-dissolved form and is endowed with the following properties (i) to (iii):

(i) has a non-powder cake-like form, (ii) has a disintegration index of 0.05 or more, and (iii) becomes fine particles having a mean particle diameter of 10 microns or less or a fine particle fraction of 10% or more upon receipt of an air impact having an air speed of at least 1 m/sec and an air flow rate of at least 17 ml/sec.

The detailed description of the composition and preparing method of the freeze-dried composition of the present invention in the above section (1) holds for this section.

The freeze-dried composition is subjected to a freeze-drying process in the vessel and it is to be housed therein. The amount of the freeze-dried composition housed in the vessel is preferably an amount containing a unit dose (single dose) or a plurality of doses, specifically 2 to 3 doses, of the active ingredients. More preferably, it is an amount containing a unit dose (single dose) of the active ingredient. Moreover, the specific amount of the freeze-dried composition to be housed in the vessel will vary according to the type and content of the active ingredient contained in the freeze-dried composition, and is selected as appropriate from amounts that can be inhaled, with there being no particular limitation; nevertheless, the amount is generally 30 mg or less, preferably 20 mg or less, more preferably 10 mg or less, particularly preferably 5 mg or less.

As the dry powder inhaler, it is preferable to adopt a device comprising ① a member for applying an air impact (or a member for introducing air) and ② a member for discharging fine particles (or a member for administering by inhalation), in which, by a member for introducing air (member ①) air is introduced into (inflow) a vessel which houses the non-powder-form freeze-dried composition and the freeze-dried composition is pulverized into fine particles using the impact (jet pressure) of the air that has been introduced into (flowed into) the vessel, and then, using the member ②  for discharging fine particles, the dried powder composition made into fine particles by the member ① is discharged from the vessel. Then, the fine particles are directly administered to a user.

An example of such device is the dry powder inhaler of the present invention mentioned in the section (3).

The dry powder inhalation system suitable for transpulmonary administration according to the present invention includes a vessel housing the freeze-dried composition of the present invention and a dry powder inhaler of the present invention used in combination at the time of inhalation. In other words, the dry powder inhalation system of the present invention, at least when used for inhalation, comprises the vessel housing the freeze-dried composition of the present invention and the dry powder inhaler of the present invention.

According to the system of the present invention, by introducing air into the vessel housing the freeze-dried composition of the present invention using the dry powder inhaler for applying an air impact having an air speed of at least 1 m/sec and an air flow rate of at least 17 ml/sec to the freeze-dried composition in the vessel. Thus, a dry powdered preparation having a particle size suitable for transpulmonary administration by inhalation or having fine particle fraction usable efficiently for transpulmonary administration by inhalation can be obtained.

Examples of the particle diameter suitable for transpulmonary administration by inhalation include the mean particle diameter, more specifically, an aerodynamic mean particle diameter (mass median aerodynamic diameter, MMAD) is 10 microns or less, preferably 5 microns or less. The effective particle proportion (fine particle fraction) used efficiently for transpulmonary administration by inhalation is at least 10%, preferably at least 20%, more preferably 25%, yet more preferably at least 30%, and in particular preferably at least 35%.

Furthermore, the system allows transpulmonary administration of the obtained dry powdered preparation directly to a user by inhalation. Therefore, the dry powder inhalation system for transpulmonary administration of the present invention is a system for producing a dry powdered preparation suitable for transpulmonary administration and, at the same time, a system for transpulmonarily administering the dry powder preparation to a user.

The dry powder inhalation system for transpulmonary administration of the present invention encompasses the specific embodiments defined in the following items:

401. A dry powder inhalation system for transpulmonary administration, using a combination of:

(1) a vessel housing a freeze-dried composition that is prepared by freeze-drying a composition liquid containing ingredients in the non-dissolved form and has the following properties:
(i) a non-powder cake-like form,
(ii) a disintegration index of 0.05 or more, and
(iii) a property of becoming fine particles having a mean particle diameter of 10 microns or less or a fine particle fraction of 10% or more upon receiving an air impact having an air speed of at least 1 m/sec and an air flow rate of at least 17 ml/sec; and
(2) a device comprising a member capable of applying said air impact to the freeze-dried composition in said vessel, and a member for discharging the powder-form freeze-dried composition that has been made into fine particles.

402. The dry powder inhalation system for transpulmonary administration according to item 401, wherein the vessel housing the freeze-dried composition contains active ingredients of a single dose.

403. The dry powder inhalation system for transpulmonary administration according to item 401, wherein the vessel and the device are used in combination at the time of inhalation.

404. The dry powder inhalation system for transpulmonary administration according to item 401, wherein the disintegration index of the freeze-dried composition is in a range of 0.05 to 1.5.

405. The dry powder inhalation system for transpulmonary administration according to item 401, wherein the air impact of (iii) is generated by air having an air speed of at least 2 m/sec and an air flow rate of at least 17 ml/sec.

406. The dry powder inhalation system for transpulmonary administration according to item 401, wherein the air impact of (iii) is generated by air having an air speed in a range of 1 to 300 m/sec and an air flow rate of at least 17 ml/sec.

407. The dry powder inhalation system for transpulmonary administration according to item 401, wherein the air impact of (iii) is generated by air having an air speed of at least 1 m/sec and an air flow rate of at least 20 ml/sec.

408. The dry powder inhalation system for transpulmonary administration according to item 401, wherein the air impact of (iii) is generated by air having an air speed of at least 1 m/sec and an air flow rate in a range of 17 ml/sec to 15 L/sec.

409. The dry powder inhalation system for transpulmonary administration according to item 401, wherein the freeze-dried composition has a property of becoming fine particles having a mean particle diameter of 5 microns or less or a fine particle fraction of 20% or more upon receipt of an air impact.

410. The dry powder inhalation system for transpulmonary administration according to item 401, wherein the freeze-dried composition contains a low-molecular-weight drug as the active ingredient.

411. The dry powder inhalation system for transpulmonary administration according to item 401, wherein the freeze-dried composition contains a high-molecular-weight drug such as proteins, a nucleic acid or the like as the active ingredient.

412. The dry powder inhalation system for transpulmonary administration according to item 401, wherein the freeze-dried composition contains a nucleic acid as an active ingredient with held in the holder.

413. The dry powder inhalation system for transpulmonary administration according to item 310, wherein the freeze-dried composition contains a low-molecular-weight drug as the active ingredient, and at least one selected from the group consisting of amino acids, dipeptides, tripeptides, and saccharides as a carrier.

414. The dry powder inhalation system for transpulmonary administration according to item 411, wherein the freeze-dried composition contains a high-molecular-weight drug such as proteins, a nucleic acid or the like as the active ingredient, and at least one selected from the group consisting of amino acids, dipeptides, tripeptides, and saccharides as a carrier.

415. The dry powder inhalation system for transpulmonary administration according to item 413, wherein the freeze-dried composition contains a low-molecular-weight drug as the active ingredient, and at least one selected from the group consisting of hydrophobic amino acids, hydrophobic dipeptides, and hydrophobic tripeptides as the carrier.

416. The dry powder inhalation system for transpulmonary administration according to item 414, wherein the freeze-dried composition contains a high-molecular-weight drug such as proteins, a nucleic acid or the like as the active ingredient, and at least one selected from the group consisting of hydrophobic amino acids, hydrophobic dipeptides, and hydrophobic tripeptides as the carrier.

417. The dry powder inhalation system for transpulmonary administration according to item 401, wherein the freeze-dried composition is a water-soluble composition.

418. The dry powder inhalation system for transpulmonary administration according to item 301, wherein the device is:

i) a dry powder inhaler for transpulmonary administration, being a device used for making a freeze-dried composition that has been housed in non-powder form in a vessel into fine particles, and administering the resulting fine particles to a user by inhalation, comprising a needle part having an air jet flow path, a needle part having a discharge flow path, air pressure-feeding member for feeding air into the air jet flow path of said needle part, and an inhalation port that communicates with the discharge flow path of said needle part, and characterized by being constituted such that a stopper that seals up said vessel is pierced by said needle parts, thus communicating the air jet flow path and the discharge flow path with the inside of said vessel, and air is jetted into said vessel through said air jet flow path using said air pressure-feeding member, thus pulverizing said freeze-dried composition into fine particles by the impact of the jetted air, and discharging the fine particles obtained from the inhalation port via said discharge flow path, or ii) a dry powder inhaler for transpulmonary administration, being a device used for making a freeze-dried composition that has been housed in non-powder form in a vessel into fine particles, and administering the resulting fine particles to a user by inhalation, comprising a needle part having a suction flow path, a needle part having an air introduction flow path, and an inhalation port that communicates with said suction flow path, and characterized by being constituted such that, in a state in which a stopper sealing up said vessel has been pierced by said needle parts, through the inhalation pressure of the user, air in said vessel is inhaled from said inhalation port, and at the same time outside air flows into said vessel, at a negative pressure, through said air introduction flow path, and as a result said freeze-dried composition is pulverized into fine particles by the impact of the air flowing in, and the fine particles obtained are discharged from the inhalation port through said suction flow path.

419. The dry powder inhalation system for transpulmonary administration according to item 418, as the device, using the dry powder inhaler comprising:

a holder part for holding a vessel that is sealed up with a stopper and houses a freeze-dried composition in a non-powder cake-like form that will be made into fine particles upon receiving an air impact, a member for applying an air impact to said freeze-dried composition in said vessel, and sucking said freeze-dried composition in a powder-form that has been made into fine particles by the air impact out from said vessel, a needle part having a auction flow path for sucking said freeze-dried composition out from said vessel, and an air introduction flow path for introducing outside air into said vessel, a suction port that communicates with said suction flow path of said needle part, a guide part for guiding said holder part in the axial direction of said needle part, a holder operating part that has a mechanism part for, when said vessel is held by said holder part, advancing the vessel towards a needle tip of said needle part to pierce the stopper of the vessel with said needle tip, and retreating the vessel from said needle tip to separate the stopper of the vessel from said needle tip, and an operator that operates the mechanism part, and is constituted such that said operating member can be operated with a force smaller than the force necessary for the mechanism part to pierce the stopper of the vessel with said needle part, and a housing that supports said needle part and is for providing said suction port, said guide part and said holder operating part, and constituted such that, in a state in which said stopper has been pierced by said needle part to communicate the suction flow path and the air introduction flow path of said needle part with the inside of said vessel and position the tip of the air introduction flow path at said freeze-dried composition, through the inhalation pressure of a user, air in said vessel is inhaled from said suction port, and air is made to flow into said vessel through the air introduction flow path, thus applying an air impact to the freeze-dried composition in said vessel.

420. The dry powder inhalation system for transpulmonary administration according to item 401, using a combination of:

(1) a vessel housing a freeze-dried composition that is prepared by freeze-drying a composition liquid containing ingredients in the non-dissolved form, and has the following properties:

(i) a non-powder cake-like form, (ii) a disintegration index in a range of 0.05 to 1.5, and (iii) a property of becoming fine particles having a mean particle diameter of 10 microns or less or a fine particle fraction of 10% or more upon receipt of an air impact having an air speed in a range of 1 to 300 m/sec and an air flow rate in a range of 17 ml/sec to 15 L/sec; and (2) a device comprising a member capable of applying said air impact to the freeze-dried composition in said vessel, and a member for discharging the powder-form freeze-dried composition that has been made Into fine particles.

421. The dry powder inhalation system for transpulmonary administration according to item 420, wherein the vessel housing the freeze-dried composition housing a freeze-dried composition containing a single dose of active ingredient.

422. The dry powder inhalation system for transpulmonary administration according to item 420, wherein the air speed is 1 to 250 m/sec.

423. The dry powder inhalation system for transpulmonary administration according to item 420, wherein the air flow rate is 20 ml/sec to 10 L/sec.

(5) Transpulmonary Administration Method

The present invention further provides a transpulmonary administration method comprising making a freeze-dried composition in a non-powder form into fine particles suitable for transpulmonary administration at the time of usage (administration), and administering the resulting preparation in a powder form with fine particles by inhalation. The transpulmonary administration method can be carried out using the dry powder inhalation system for transpulmonary administration of the present invention described in detail in the section (4), and preferably using the dry powder inhalation system for transpulmonary administration comprising the vessel which houses the freeze-dried composition of the present invention described in detail in the section (1), which is prepared by freeze-drying the composition liquid containing ingredients in the non-dissolved form and a dry powder inhaler described in the section (3).

The transpulmonary administration method of the present invention encompasses the specific embodiments defined in the following items:

501. A transpulmonary administration method comprising:
making a freeze-dried composition into fine particles having a mean particle diameter of 10 microns or less or a fine particle fraction of 10% or more by applying an air impact having an air speed of at least 1 m/sec and an air flow rate of at least 17 ml/sec to the freeze-dried composition at the time of use, and
administering the resulting fine particle powder to a user by inhalation;
the freeze-dried composition prepared by freeze-drying a composition liquid containing ingredients in the non-dissolved form and having the following properties:

(i) has a non-powder cake-like form, (ii) has a disintegration index of 0.05 or more, and (iii) becomes fine particles having a mean particle diameter of 10 microns or less or a fine particle fraction of 10% or more upon receipt of the air impact.

502. The transpulmonary administration method according to item 501, wherein the freeze-dried composition contains a single dose of active ingredients.

503. The transpulmonary administration method according to item 501, wherein the freeze-dried composition is housed in a vessel, and the fine particle powder are made using a device comprising a member capable of applying the air impact to the freeze-dried composition in the vessel and a member for discharging the resulting fine particle powder-form freeze-dried composition out of the vessel.

504. The transpulmonary administration method according to item 503, wherein the disintegration index of the freeze-dried composition is in the range of 0.05 to 1.5.

505. The transpulmonary administration method according to item 503, wherein the air impact of (iii) is generated by air having an air speed of at least 2 m/sec and an air flow rate of at least 17 ml/sec.

506. The transpulmonary administration method according to item 503, wherein the air impact of (iii) is generated by air having an air speed in a range of 1 to 300 m/sec and an air flow rate of at least 17 ml/sec.

507. The transpulmonary administration method according to item 503, wherein the air impact of (iii) is generated by air having an air speed of at least 1 m/sec and an air flow rate of at least 20 ml/sec.

508. The transpulmonary administration method according to item 503, wherein the air impact of (iii) is generated by air having an air speed of at least 1 m/sec and an air flow rate in a range of 17 ml/sec to 15 L/sec.

509. The transpulmonary administration method according to item 503, wherein the freeze-dried composition contains a low-molecular-weight drug as the active ingredient.

510. The transpulmonary administration method according to item 503, wherein the freeze-dried composition contains a high-molecular-weight drug such as a protein, a nucleic acid or the like as the active ingredient.

511. The transpulmonary administration method according to item 503, wherein the freeze-dried composition contains a nucleic acid as the active ingredient with held in the holder.

512. The transpulmonary administration method according to item 509, wherein the freeze-dried composition contains a low-molecular-weight drug as the active ingredient, and at least one selected from the group consisting of amino acids, dipeptides, tripeptides, and saccharides as a carrier.

513. The transpulmonary administration method according to item 510, wherein the freeze-dried composition contains a high-molecular-weight drug such as proteins, a nucleic acid or the like as the active ingredient, and at least one selected from the group consisting of amino acids, dipeptides, tripeptides, and saccharides as a carrier.

514. The transpulmonary administration method according to item 512, wherein the freeze-dried composition contains a low-molecular-weight drug as the active ingredient, and at least one selected from the group consisting of hydrophobic amino acids, hydrophobic dipeptides, and hydrophobic tripeptides as the carrier.

515. The transpulmonary administration method according to item 513, wherein the freeze-dried composition contains a high-molecular-weight drug such as proteins, a nucleic acid or the like as the active ingredient, and at least one selected from the group consisting of hydrophobic amino acids, hydrophobic dipeptides, and hydrophobic tripeptides as the carrier.

516. The transpulmonary administration method according to Item 503, wherein the freeze-dried composition is a water-soluble composition.

517. The transpulmonary administration method according to item 503, being a method of making into fine particles and administering such that the fine particles have a mean particle diameter of 5 microns or less or a fine particle fraction of 20% or more.

518. The transpulmonary administration method according to item 503, using the dry powder inhaler of item 301 or 302 shown in the section of (1) Dry powder inhaler as the device.

519. The transpulmonary administration method according to item 518, using the dry powder inhaler of item 309 shown in the section of (3) Dry powder inhaler as the device.

520. The transpulmonary administration method according to item 503, wherein the freeze-dried composition has the following properties:

(i) has a non-powder cake-like form, (ii) has a disintegration index in a range of 0.05 to 1.5, and (iii) becomes fine particles having a mean particle diameter of 10 microns or less or a fine particle fraction of 10% or more upon receiving an air impact having an air speed in a range of 1 to 300 m/sec and an air flow rate in a range of 17 ml/sec to 15 L/sec, and the fine particles are made using a dry powder inhaler comprising a member capable of applying said air impact to the freeze-dried composition in the vessel and a member for discharging the resulting fine particle powder-form freeze-dried composition out of the vessel.

521. The transpulmonary administration method according to item 520, wherein the air speed is 1 to 250 m/sec.

522. The transpulmonary administration method according to item 520, wherein the air flow rate is 20 ml/sec to 10 L/sec.

(6) Use of a Freeze-Dried Composition for Transpulmonary Administration by Inhalation The present invention also provides use of a freeze-dried composition in a non-powder form for the transpulmonary administration by inhalation. The use encompasses the specific embodiments defined in the following items:

601. Use of a freeze-dried composition for transpulmonary administration by inhalation, the freeze-dried composition prepared by freeze-drying a composition liquid containing ingredients in the non-dissolved form and having the following properties:

(i) has a non-powder cake-like form, (ii) has a disintegration index of 0.05 or more, and (iii) becomes fine particles having a mean particle diameter of 10 microns or less or a fine particle fraction of 10% or more upon receipt of an air impact having an air speed of at least 1 m/sec and an air flow rate of at least 17 ml/sec, and being used by forming into fine particles having said mean particle diameter or said fine particle fraction.

602. The use of a freeze-dried composition for transpulmonary administration according to item 601, wherein the freeze-dried composition contains the active ingredient of a single dose.

603. The use of a freeze-dried composition for transpulmonary administration according to item 601, wherein the freeze-dried composition is housed in a vessel, and the fine particles are made using a device comprising a member capable of applying the air impact to the freeze-dried composition in the vessel and a member for discharging the resulting fine particle powder-form freeze-dried composition out of the vessel.

604. The use of a freeze-dried composition for transpulmonary administration according to item 603, wherein the disintegration index of the freeze-dried composition is in the range of 0.05 to 1.5.

605. The use of a freeze-dried composition for transpulmonary administration according to item 603, wherein the freeze-dried composition becomes fine particles having a mean particle diameter of 10 microns or less or a fine particle fraction of 10% or more upon receiving an air impact having an air speed of at least 2 m/sec and an air flow rate of at least 17 ml/sec.

606. The use of a freeze-dried composition for transpulmonary administration according to item 603, wherein the freeze-dried composition becomes fine particles having a mean particle diameter of 10 microns or less or a fine particle fraction of 10% or more upon receiving an air impact having an air speed in a range of 1 to 300 m/sec and an air flow rate of at least 17 ml/sec.

607. The use of a freeze-dried composition for transpulmonary administration according to item 603, wherein the freeze-dried composition becomes fine particles having a mean particle diameter of 10 microns or less or a fine particle fraction of 10% or more upon receiving an air impact having an air speed of at least 1 m/sec and an air flow rate of at least 20 ml/sec.

608. The use of a freeze-dried composition for transpulmonary administration according to item 603, wherein the freeze-dried composition becomes fine particles having a mean particle diameter of 10 microns or less or a fine particle fraction of 10% or more upon receiving an air impact having an air speed of at least 1 m/sec and an air flow rate in a range of 17 ml/sec to 15 L/sec.

609. The use of a freeze-dried composition for transpulmonary administration according to item 603, wherein the freeze-dried composition becomes fine particles having a mean particle diameter of 5 microns or less or a fine particle fraction of 20% or more upon receiving an air impact.

610. The use of a freeze-dried composition for transpulmonary administration according to item 603, wherein the freeze-dried composition contains a low-molecular-weight drug as the active ingredient.

611. The use of a freeze-dried composition for transpulmonary administration according to item 603, wherein the freeze-dried composition contains a high-molecular-weight drug such as proteins, a nucleic acid or the like as the active ingredient.

612. The use of a freeze-dried composition for transpulmonary administration according to item 603, wherein the freeze-dried composition contains a nucleic acid as the active ingredient with held in the holder.

613. The use of a freeze-dried composition for transpulmonary administration according to item 610, wherein the freeze-dried composition contains a low-molecular-weight drug as the active ingredient, and at least one selected from the group consisting of amino acids, dipeptides, tripeptides, and saccharides as a carrier.

614. The use of a freeze-dried composition for transpulmonary administration according to item 611, wherein the freeze-dried composition contains a high-molecular-weight drug such as a protein, a nucleic acid or the like as the active ingredient, and at least one selected from the group consisting of amino acids, dipeptides, tripeptides, and saccharides as a carrier.

615. The use of a freeze-dried composition for transpulmonary administration according to item 613, wherein the freeze-dried composition contains a low-molecular-weight drug as the active ingredient, and at least one selected from the group consisting of hydrophobic amino acids, hydrophobic dipeptides, and hydrophobic tripeptides as the carrier.

616. The use of a freeze-dried composition for transpulmonary administration according to item 614, wherein the freeze-dried composition contains a high-molecular-weight drug such as proteins, a nucleic acid or the like as the active ingredient, and at least one selected from the group consisting of hydrophobic amino acids, hydrophobic dipeptides, and hydrophobic tripeptides as the carrier.

617. The use of a freeze-dried composition for transpulmonary administration according to item 603, wherein the freeze-dried composition is a water-soluble composition.

618. The use of a freeze-dried composition for transpulmonary administration according to item 603, using the dry powder inhaler of item 301 or 302 shown in the section of (3) Dry powder inhaler as the device.

619. The use of a freeze-dried composition for transpulmonary administration according to item 618, using the dry powder inhaler of item 109 shown in the section of (3) Dry powder inhaler as the device.

620. The use of a freeze-dried composition for transpulmonary administration according to item 603, wherein the freeze-dried composition which is prepared by freeze-drying a composition liquid containing ingredients in the non-dissolved form and has the following properties:

(i) has a non-powder cake-like form, (ii) has a disintegration index in a range of 0.05 to 1.5, and (iii) becomes fine particles having a mean particle diameter of 10 microns or less or a fine particle fraction of 10% or more upon receipt of an air impact having an air speed in a range of 1 to 300 m/sec and an air flow rate in a range of 17 ml/sec to 15 L/sec, and the fine particles are made using a device comprising a member capable of applying the air impact to the freeze-dried composition in the vessel and a member for discharging the resulting fine particle powder-form freeze-dried composition out of the vessel.

621. The use of a freeze-dried composition in transpulmonary administration according to item 620, wherein the air speed is 1 to 250 m/sec.

622. The use of a freeze-dried composition in transpulmonary administration according to item 620, wherein the air flow rate is 20 mi/sec to 10 L/sec.

(7) Use of a Freeze-dried Composition For Manufacture of a Dry Powdered Preparation for Transpulmonary Administration by Inhalation Furthermore, the present invention provides use of a freeze-dried composition in a non-powder form for manufacture of a dry powdered preparation for transpulmonary administration by inhalation. The use encompasses the specific embodiments defined in the following items:

701. Use of a freeze-dried composition for manufacture of a dry powdered preparation for transpulmonary administration by inhalation, the freeze-dried composition having the following properties:
(i) prepared by freeze-drying a composition liquid containing ingredients in the non-dissolved form,
(ii) has a non-powder cake-like form,
(iii) has a disintegration index of 0.05 or more, and
(iv) becomes fine particles having a mean particle diameter of 10 microns or less or a fine particle fraction of 10% or more upon receipt of an air impact having an air speed of at least 1 m/sec and an air flow rate of at least 17 ml/sec, and being used by forming into fine particles having said mean particle diameter or said fine particle fraction at the time of use.

702. The use of a freeze-dried composition for manufacture of a dry powdered preparation for transpulmonary administration according to item 701, wherein the freeze-dried composition contains the active ingredient of a single dose.

703. The use of a freeze-dried composition for manufacture of a dry powdered preparation for transpulmonary administration according to item 701, wherein the disintegration index of the freeze-dried composition is in the range of 0.05 to 1.5.

704. The use of a freeze-dried composition for manufacture of a dry powdered preparation for transpulmonary administration according to Item 701, wherein the freeze-dried composition becomes fine particles having a mean particle diameter of 10 microns or less or a fine particle fraction of 10% or more upon receipt of an air impact having an air speed of at least 2 m/sec and an air flow rate of at least 17 ml/sec.

705. The use of a freeze-dried composition for manufacture of a dry powdered preparation for transpulmonary administration according to item 701, wherein the freeze-dried composition becomes fine particles having a mean particle diameter of 10 microns or less or a fine particle fraction of 10% or more upon receipt of an air impact having an air speed in a range of 1 to 300 m/sec and an air flow rate of at least 17 ml/sec.

706. The use of a freeze-dried composition for manufacture of a dry powdered preparation for transpulmonary administration according to item 701, wherein the freeze-dried composition becomes fine particles having a mean particle diameter of 10 microns or less or a fine particle fraction of 10% or more upon receipt of an air impact having an air speed of at least 1 m/sec and an air flow rate of at least 20 ml/sec.

707. The use of a freeze-dried composition for manufacture of a dry powdered preparation for transpulmonary administration according to item 701, wherein the freeze-dried composition becomes fine particles having a mean particle diameter of 10 microns or less or a fine particle fraction of 10% or more upon receipt of an air impact having an air speed of at least 1 m/sec and an air flow rate in a range of 17 ml/sec to 15 L/sec.

708. The use of a freeze-dried composition for manufacture of a dry powdered preparation for transpulmonary administration according to item 701, wherein the freeze-dried composition becomes fine particles having a mean particle diameter of 5 microns or less or a fine particle fraction of 20% or more upon receipt of an air impact.

709. The use of a freeze-dried composition for manufacture of a dry powdered preparation for transpulmonary administration according to item 701, wherein the freeze-dried composition contains a low-molecular-weight drug as an active ingredient.

710. The use of a freeze-dried composition for manufacture of a dry powdered preparation for transpulmonary administration according to item 701, wherein the freeze-dried composition contains a high-molecular-weight drug such as proteins, a nucleic acid or the like as an active ingredient.

711. The use of a freeze-dried composition for manufacture of a dry powdered preparation for transpulmonary administration according to item 701, wherein the freeze-dried composition contains a nucleic acid as the active ingredient with held in the holder.

712. The use of a freeze-dried composition for manufacture of a dry powdered preparation for transpulmonary administration according to item 701, wherein the freeze-dried composition contains a low-molecular-weight drug as the active ingredient, and at least one selected from the group consisting of amino acids, dipeptides, tripeptides, and saccharides as a carrier.

713. The use of a freeze-dried composition for manufacture of a dry powdered preparation for transpulmonary administration according to item 710, wherein the freeze-dried composition contains a high-molecular-weight drug such as proteins, a nucleic acid or the like as the active ingredient, and at least one selected from the group consisting of amino acids, dipeptides, tripeptides, and saccharides as a carrier.

714. The use of a freeze-dried composition for manufacture of a dry powdered preparation for transpulmonary administration according to item 712, wherein the freeze-dried composition contains a low-molecular-weight drug as the active ingredient, and at least one selected from the group consisting of hydrophobic amino acids, hydrophobic dipeptides, and hydrophobic tripeptides as the carrier.

715. The use of a freeze-dried composition for manufacture of a dry powdered preparation for transpulmonary administration according to item 713, wherein the freeze-dried composition contains a high-molecular-weight drug such as proteins, a nucleic acid or the like as the active ingredient, and at least one selected from the group consisting of hydrophobic amino acids, hydrophobic dipeptides, and hydrophobic tripeptides as the carrier.

716. The use of a freeze-dried composition for manufacture of a dry powdered preparation for transpulmonary administration according to item 701, wherein the freeze-dried composition is a water-soluble composition.

717. The use of a freeze-dried composition for manufacture of a dry powdered preparation for transpulmonary administration according to item 701, wherein the mean particle diameter of the fine particles of the powdered preparation for transpulmonary administration is 5 microns or less or the fine particle fraction of the fine particles is 20% or more.

718. The use of a freeze-dried composition for manufacture of a dry powdered preparation for transpulmonary administration according to item 701, wherein the freeze-dried composition is housed in a vessel, and the fine particles are prepared by using a device comprising a member for applying a prescribed air impact to the freeze-dried composition housed in the vessel and a member for discharging the resulting fine particle powder form freeze-dried composition out of the vessel.

719. The use of a freeze-dried composition for manufacture of a dry powdered preparation for transpulmonary administration of item 718, using the dry powder inhaler according to item 301 or 302 shown in the section of (3) Dry powder inhaler as the device.

720. The use of a freeze-dried composition for manufacture of a dry powdered preparation for transpulmonary administration according to item 719, using the dry powder inhaler of item 309 shown in the section of (3) Dry powder inhaler as the device.

721. The use of a freeze-dried composition for manufacture of a dry powdered preparation for transpulmonary administration according to item 701, using the freeze-dried composition having the following properties:

(i) prepared by freeze-drying a composition liquid containing ingredients in the non-dissolved form, (ii) has a non-powder cake-like form, (iii) has a disintegration index in a range of 0.05 to 1.5. and (iv) becomes fine particles having a mean particle diameter of 10 microns or less or a fine particle fraction of 10% or more upon receiving an air impact having an air speed in a range of 1 to 300 m/sec and an air flow rate in a range of 17 ml/sec to 15 L/sec.

722. The use of a freeze-dried composition for manufacture of a powdered preparation for transpulmonary administration according to item 721, wherein the air speed is 1 to 250 m/sec.

723. The use of a freeze-dried composition for manufacture of a powdered preparation for transpulmonary administration according to item 721, wherein the air flow rate is 20 ml/sec to 10 L/sec.

(8) Use of a Composition Liquid Containing Ingredients in the Non-Dissolved Form for Manufacture of a Freeze-Dried Powdered Composition for Preparing a Dry Powder Preparation for Transpulmonary Administration Furthermore, the present invention relates to a use of a composition liquid containing ingredients in the non-dissolved form for manufacture of a freeze-dried powdered composition for preparing a dry powder preparation for transpulmonary administration.

It should be noted that the composition in the non-dissolved form containing ingredients for manufacture of a freeze-dried composition, a preparation method thereof, a preparation method of a freeze-dried composition using the same, a method of using the freeze-dried composition obtained (a preparation method of a freeze-dried preparation for transpulmonary administration) are as described in the above.

EXAMPLE

Following is a detailed description of the present invention, citing examples; however, the present invention is not limited to these examples.

In the following examples, the disintegration index of the non-powder-form freeze-dried composition (freeze-dried cake) of the present invention, and the fine particle fraction (%), which is an indicator for evaluating the delivery into the lungs of the dry powdered preparation produced, were calculated in accordance with the following methods.

<Calculation of Disintegration Index>

1.0 ml of n-hexane is instilled gently down the wall of the vessel into the prepared non-powder-form freeze-dried composition (freeze-dried cake), and agitation is carried out for about 10 seconds at 3,000 rpm using an Automatic Lab-Mixer NS-8 (manufactured by Pasolina). The mixture obtained is put into a UV cell (manufactured by Shimadzu GLC Center) of optical path length 1 mm and optical path width 10 mm, and then the turbidity of the mixture is measured immediately at a measurement wavelength of 500 nm using a spectrophotometer (UV-240, manufactured by Shimadzu Corporation). The value obtained by dividing the turbidity obtained by the total formulation amount (the total amount (weight) of the active ingredient and the carrier) is taken as the disintegration index.

<Calculation of Fine Particle Fraction>

A vessel filled with the prepared non-powder-form freeze-dried composition is installed into the dry powder inhaler, and using the device a prescribed air impact is applied on the composition, and the fine powdered preparation thus produced is discharged directly into apparatus A (a twin impinger: manufactured by Copley, UK) as mentioned in the European Pharmacopoeia (Third Edition Supplement 2001, p 113-115). After this, the solvents in stage 1 and stage 2 of the apparatus are respectively collected, and the active ingredient contained in each solvent in the stage 1 or stage 2 is assayed using an appropriate method in accordance with the type of active ingredient in the freeze-dried composition, for example a bioassay method or HPLC (see the report of Lucas et al. (Pharm. Res., 15 (4), 562-569 (1998)) and the report of Iida et al. (Yakugaku Zasshi, 119 (10), 752-762 (1999)). The fraction that can be expected to be delivered into the lungs is that in stage 2 (the aerodynamic diameter of particles recovered in this fraction is 6.4 µm or less); the proportion of the active ingredient that reaches stage 2 and is recovered here is generally called the fine particle fraction (the amount that can be expected to reach the lungs), and is taken as a yardstick for evaluating the suitability as an inhalation for transpulmonary administration.

In the Examples and Comparative Examples given below, the active ingredients contained in stage 1 and stage 2 were quantitated, and the weight amount of the active ingredient in stage 2 was divided by the total weight amount of the active ingredients jetted out (the total weight amount of the active ingredients contained in stage 1 and stage 2: hereinafter also referred to as "Stage 1+Stage 2") to calculate fine particles fraction. Moreover, as a rule in the European Pharmacopoeia, when using the twin impinger (manufactured by Copley, UK), it is stipulated that suction is carried out at an air suction flow rate of 60 L/min, i.e. 1 L/sec, and hence in the Examples and Comparative Examples below this was followed.

Embodiment 1

Dry Powder Inhaler (Jet Type 1)

A description of an embodiment of the jet type dry powder inhaler used in the present invention will now be given using FIG. 1.

The dry powder inhaler is an air jet type apparatus for breaking down into fine particles and delivering into the lungs a unit or a plurality of doses of a non-powder-form freeze-dried composition 2 housed at the bottom of a vessel 1, and comprises a needle 5 that has an air jet flow path 3 and a discharge flow path 4, an air intake member 7 that has an inhalation port 6 and is attached to a base end of the needle part 5, a tubular safety cover 8 that surrounds the needle part 5 and also holds the vessel 1, and air pressure-feeding member 9.

The air pressure-feeding member 9 is manually operated and comprises a tubular bellows body 10. An intake port 12 equipped with an intake valve 11, and a discharge port 14 equipped with a discharge valve 13 are provided in the bellows body 10. The discharge port 14 is attached to a connecting port 15 formed at the base end of the air jet flow path 3 of the needle part 5, and communicates with the air jet flow path 3. By applying a compressive force to the bellows body 10 and thus contracting the bellows body 10 in a state in which the intake valve 11 is closed, the discharge valve 13 is opened, and air in the bellows body 10 is discharged into the vessel 1 from the discharge port 14 via the air jet flow path 3. When the compressive force is released, on the other hand, the bellows body 10 expands due to the elastic restoring force of the bellows body 10, and in a state in which the discharge valve 13 is closed, the intake valve 11 opens, and air is introduced into the bellows body 10.

When using the dry powder inhaler, as shown in FIG. 1, the vessel 1 is inserted into the tubular safety cover 8, and a stopper 1a of the vessel 1 is pierced by the needle part 5, thus communicating the air jet flow path 3 and the discharge flow path 4 with the inside of the vessel 1. In this state, if the bellows body 10 of the air pressure-feeding member 9 is contracted to discharge air from the discharge port 14, then this air passes through the air jet flow path 3 and is jetted out from the tip of the needle part 5 towards the freeze-dried composition 2 in the vessel, and due to the resulting air impact the freeze-dried composition 2 becomes fine particles, which then pass through the discharge flow path 4 of the needle part 5 and are discharged from the inhalation port 6 of the air intake member 7. The user (patient) inhales these fine particles from the inhalation port 6 of the air intake member, whereupon the fine particles of the freeze-dried composition 2 are delivered into the lungs of the user (patient). The material of the stopper of the vessel for use in the invention is not limited, and can be selected from materials usually used for a stopper of a vessel for holding a drug or compound, such as rubber, plastic, aluminum or the like.

With this jet type dry powder inhaler, the air jet amount is set to be about 20 ml, the volume of the vessel about 5 ml, the bore (diameter) of the air jet flow path 3 about 1.2 mm, and the bore (diameter) of the discharge flow path 4 about 1.8 mm.

Note, however, that there is no limitation to this. The preferable range for the bores of the air jet flow path 3 and the discharge flow path 4 varies according to the size of the vessel and so on. These bores can be selected as appropriate from a range of 0.3 to 10 mm, preferably 0.3 to 7 mm, more preferably 0.5 to 5 mm.

Moreover, regarding the air pressure-feeding member 9, the discharge amount of fine particles required for administration by inhalation can be adjusted by adjusting the speed of compression of the bellows body 10. Adjustment can also be carried out by such air jet such that most of the freeze-dried composition 2 is broken down into fine particles.

Embodiment 2

Dry Powder Inhaler (Self-inhaling Type 1)

A description of an embodiment (first embodiment) of the self-inhaling type dry powder inhaler used in the present invention will now be given using FIG. 2. The dry powder inhaler shown in FIG. 2 comprises a needle part 5 having a suction flow path 16 and an air Introduction flow path 17, a tubular safety cover 8, and an air intake member 19 that has an inhalation port 18 and communicates with the suction flow path 16. The air intake member 19 is connected to the base end of the suction flow path 16 of the needle part 5.

When using the dry powder inhaler, as shown In FIG. 2, the vessel 1 is inserted into the tubular safety cover 8, and an stopper 1*a* of the vessel 1 is pierced by the needle part 5, thus communicating the suction flow path 16 and the air introduction flow path 17 with the inside of the vessel 1. In this state, through the inhalation pressure of the user (patient), air in the vessel 1 is sucked in from the inhalation port 18 via the suction flow path 16, and at the same time outside air flows into the vessel 1, which is now at a negative pressure, from the air introduction flow path 17. At this time, the freeze-dried composition 2 is made into fine particles through the air impact acting on the freeze-dried composition 2, and the fine particles produced are delivered into the user's (patient's) lungs from the inhalation port 18 via the suction flow path 16.

Moreover, with this dry powder inhaler, setting is carried out such that most of the freeze-dried composition 2 is made into fine particles and discharged from the inhalation port 18 through one Inhalation of the user (patient). It is considered that the air flow rate of one inhalation of the user (patient) is 5 to 300 L/min, preferably 10 to 200 L/min, more preferably 10 to 100 L/min, but the design of the self-inhaling type dry powder inhaler of the present invention is modified as appropriate in accordance with the respiratory ability of the user (patient) using the device. With the dry powder inhaler shown in FIG. 2, in accordance with the respiratory ability of the user (patient) in question, the volume of the vessel has been set to about 10 ml, and the bores of the air introduction flow path 17 and the suction flow path 16 to about 1.5 mm. As a result, the settings are such that the freeze-dried composition 2 is made into fine particles and discharged from the inhalation port 18 with virtually none left behind through one inhalation of the user (patient).

Embodiment 3

Dry Powder Inhaler (Self-inhaling Type 2)

A description of an embodiment (second embodiment) of the self-inhaling type dry powder inhaler used in the present invention will now be given using FIG. 3. The dry powder inhaler shown in FIG. 3 is the same as the jet type dry powder inhaler shown in FIG. 1 with the bellows body 10 used for pressure-feeding air removed from the connecting port 15. The discharge flow path 4 of the jet type dry powder inhaler of FIG. 1 corresponds to a suction flow path 16, the air jet flow path 3 to an air introduction flow path 17, and the air intake member 7 having the inhalation port 6 to an air intake member 19 having an inhalation port 18.

When using the self-inhaling type dry powder inhaler in question, the main points are the same as with the dry powder inhaler shown in FIG. 2. Through the inhalation pressure of the user (patient), air in the vessel 1 is sucked in from the inhalation port 18 via the suction flow path 16, and at the same time outside air flows into the vessel 1, which is now at a negative pressure, from the air introduction flow path 17. The freeze-dried composition 2 is made into fine particles through the air impact produced accompanying this inflow of air. The fine particles produced are then delivered into the user (patient's) lungs from the inhalation port 18. As mentioned before, the air flow rate for one inhalation of the user (patient) is generally in a range of 5 to 300 L/minute; however, with the dry powder inhaler shown in FIG. 3, in accordance with the respiratory ability of the user (patient) in question, the volume of the vessel was set to about 5 ml, the bore (diameter) of the air introduction flow path 17 to about 1.2 mm, and the bore (diameter) of the suction flow path 16 to about 1.8 mm. As a result, the settings are such that most of the freeze-dried composition 2 is made into fine particles and discharged from the inhalation port 18 through one inhalation of the user (patient).

If the self-inhaling type dry powder inhaler is constituted in this way, then by detachably installing air pressure-feeding member 9 such as a bellows body 10 into the connecting port 15, the self-inhaling type dry powder inhaler can be changed into a jet type. A single dry powder inhaler can thus be used as either a self-inhaling type or a jet type as desired.

Each of the above dry powder inhalers of the present invention, regardless of whether it is a self-inhaling type or a jet type, can be constituted such that it is possible to select and set the size of the air impact such that the freeze-dried composition becomes fine particles of mean particle diameter 10 microns or less, preferably 5 microns or less, and flies out with almost none left behind.

Embodiment 4

Dry Powder Inhaler (Self-inhaling Type 3)

A description of an embodiment (third embodiment) of the self-inhaling type dry powder inhaler used in the present invention will now be given using FIGS. 4 to 10. FIG. 4 is a perspective view showing the dry powder inhaler, and FIG. 5 is a cross section showing the dry powder inhaler. Moreover, FIG. 6(*a*) is a partial cross section showing a needle part 5 and a suction port 31 of the dry powder inhaler, and (b) is a side view of the needle part 5. Furthermore, FIGS. 7 to 10 are cross sections for explaining the operation of the dry powder inhaler.

The dry powder inhaler comprises a needle part 5 in which are formed a suction flow path 16 and an air introduction flow path 17, a holder part 22 for holding a vessel 1, a housing chamber 20 for housing the vessel 1 via the holder part 22, a guide part 23 provided in the housing chamber 20 for guiding the holder part 22 in the axial direction of the needle part 5, and a holder operating part 24 for advancing and retreating the holder part 22 along the guide part 23; these are all housed in a tubular housing 21. Moreover, a mouthpiece 32 that has a suction port 31 and communicates with the suction flow path 16 of the needle part 5 is provided at a tip of the housing 21.

As shown in FIG. 7, in detail the housing 21 is formed from a housing main body 26 in which is formed a removal/insertion port 25 in a position in which the holder part 22 is retreated, and a lid 27 that opens and closes the removal/insertion port 25. The lid 27 is connected to the housing main body 26 by a hinge 21A, and a window 28 for verifying whether the vessel 1 has been loaded is provided in the lid 27.

An introduction port 29 for introducing outside air is provided in a wall of the housing 21, and a check valve 30 is installed at the introduction port 29. Moreover, the mouthpiece 32 is provided at the tip of the housing 21. The suction port 31 of the mouthpiece 32 is covered by a cap 32*a* when the dry powder inhaler is not being used.

A flange-shaped partition part 33 is formed at the base end of the needle part 5, and an end of the air introduction flow path 17 passes through the partition part 33 and opens out in an outer peripheral direction of the partition part 33. Moreover, a peripheral wall part 34 extends from an outer rim part of the partition part 33 towards the suction port 31 of the mouthpiece 32. The needle part 5 is installed into the housing 21 by fitting the partition part 33 into the tip part of the housing 21. Through this installation, the axial direction of the housing 21 and the axial direction of the needle part 5 are aligned with one another.

A remover 35 for lifting the vessel 1 from the base of the holder part 22 and removing the vessel 1 is attached to the holder part 22, and a lever 36 for lifting the vessel 1 up is formed on the remover 35.

The holder operating part 24 comprises a mechanism part 37 for moving the holder part 22 back and forth along the axial direction of the housing 21, and an operating lever for operating the mechanism part 37. The mechanism part 37 comprises a connector 39. One end of the connector 39 is connected to the holder part 22 by a hinge 40, and the other end of the connector 39 is connected to the lid 27 by a hinge 41. The lid 27 is also used as the above-mentioned operating lever. By opening and closing the lid 27, the holder part 22 is advanced and retreated along the guide part 23.

The point of action of the force for pushing down the lid 27 is shown by the arrow C in FIG. 7. That is, the distance from the hinge 21A to the point of action is made to be longer than the distance from the hinge 21A to the hinge 41. As a result, through the lever principle, the lid (operating lever) 27 can be operated by a force smaller than the force necessary to pierce the stopper 1*a* of the vessel 1 with the needle part 5.

Moreover, as shown in FIG. 6, second introduction paths 42 for supplementary introduction of air are formed in the dry powder inhaler. When sucking the freeze-dried composition that has been made into a powder from the mouthpiece 32, outside air passes through these second introduction path 42 and flows to the suction port 31 of the mouthpiece 32. As a result, the dry powder inhaler can be used without imposing a burden even by a user (patient) having reduced pulmonary capacity or a child patient. Note that the second introduction paths 42 may be omitted.

Introduction grooves 42*a* are provided in the partition part 33 of the needle part 5 and introduction grooves 42*b* are provided in the peripheral wall part 34. By fitting the mouthpiece 32 into the peripheral wall part 34 of the needle part 5, the second introduction paths 42 are thus formed from the mouthpiece 32 and the introduction grooves 42*a* and 42*b*.

A slight gap 43 is formed between the mouthpiece 32 and the housing 21, and one end 44 of the second introduction paths 42 opens out to the outside via the gap 43, while the other end 45 of the second introduction paths 42 opens out into the suction port 31 of the mouthpiece 32.

Moreover, as shown in FIG. 6, a wall 47 having vent holes 46 is provided in the suction port 31. Consequently, even in the case that the air impact applied to the freeze-dried composition 2 is small due to a lack of suction force or the like, and part of the freeze-dried composition 2 is not made into a powder, the non-powder part can be made into a powder when passing through the vent holes 46 of the wall 47.

Moreover, as shown in FIG. 6(*a*), a tip opening 17*a* of the air introduction flow path 17 of the needle part 5 is made to be closer to the freeze-dried composition 2 than a tip opening 16*a* of the suction flow path 16. As a result, dropping of the flow speed of the air that flows into the vessel 1 from the tip opening 17*a* of the air introduction flow path 17 can be suppressed as much as possible, and hence an effective air impact can be applied to the freeze-dried composition 2. Moreover, because the tip opening 16*a* of the suction flow path 16 of the needle part 5 is further from the freeze-dried composition 2 than the tip opening 17*a* of the air introduction flow path 17, making of the freeze-dried composition 2 can be made to into a fine powder in the vessel 1 as much as possible before being sucked into the air introduction flow path 16 of the needle part 5.

The dry powder inhaler is used as follows. Firstly, the lid 27 is lifted up to open the removal/insertion port 25 of the housing 21 as in FIG. 7, whereby the holder part 22 is pulled backwards to reach the removal/insertion port 25 of the housing 21. Next, the vessel 1 is installed in the holder part 22 with the stopper 1a facing forwards. Next, the lid 27 is pushed down to close the removal/insertion port 25 of the housing 21 as in FIG. 8, whereby the holder part 22 is pushed towards the needle part 5 by the connector 39, and the stopper 1a of the vessel 1 is pierced by the tip of the needle part 5, thus communicating the suction flow path 16 and the air introduction flow path 17 of the needle part 5 with the inside of the vessel 1. Next, air in the vessel 1 is sucked from the suction port 31 of the mouthpiece 32 through the suction flow path 16 of the needle part 5 by the inhalation pressure of the user (patient). At this time, the inside of the vessel 1 becomes a negative pressure and the check valve 30 opens, and outside air flows into the vessel 1 through the air introduction flow path 17 of the needle part 5. As a result, an air impact is generated in the vessel 1 and the freeze-dried composition 2 is broken down into fine particles, and the fine particles prepared are delivered into the user's (patient's) lungs from the suction port 31 via the suction flow path 16. After use, the lid 27 is lifted up to pull the holder part 22 back up to the removal/insertion port 25 of the housing 21, and then the remover 35 is lifted up by the lever 36 and the vessel 1 is removed from the holder part 22.

Even if air is conversely blown into the vessel 1 from the suction port 31 of the mouthpiece 32, discharge to the outside of the freeze-dried composition 2 made into fine particles is prevented by the check valve 30.

As mentioned before, the air flow rate of one inhalation of the user (patient) is generally in a range of 5 to 300 L/min, but with the dry powder inhaler shown in FIGS. 4 to 10, in accordance with the respiratory ability of the user (patient), the volume of the vessel 1 has been set to about 5 ml, the bore (diameter) of the air introduction flow path 17 to about 2.5 mm, and the bore (diameter) of the suction flow path 16 to about 2.5 mm. As a result, the settings are such that most of the freeze-dried composition 2 is made into fine particles and discharged from the suction port 31 through one inhalation of the user (patient).

Other embodiments of the dry powder inhaler (self-inhaling type) are shown in FIGS. 11 to 13.

With the dry powder inhaler (self-inhaling type 4) shown in FIG. 11, an operating member 48 is provided so as to be freely rotatable in the circumferential direction of the housing 21 as shown by the arrow. The mechanism part of the holder operating part, which is not shown in the drawing, comprises a spiral groove and a follower that engages into the same; when the operating member 48 is rotated, this rotation is converted to linear movement of the holder part 22 in the axial direction of the needle part 5. Note that the angle of rotation of the operator 48 is about 180°.

With the dry powder inhaler (self-inhaling type 5) shown in FIG. 12 and FIG. 13, an annular operating member 49 is installed so as to be freely rotatable in the housing 21. The mechanism part of the holder operating part, which is not shown in the drawing, comprises a feed screw; when the operating member 49 is rotated, this rotation is converted to linear movement of the holder part 22 in the axial direction of the needle part 5. The holder part 22 can be withdrawn from the back of the housing 21.

Example 1

72 μg of 'LipofectAMINE 2000' which is a cationic gene transfer liposome (manufactured by Invitrogen Corporation) and 24 μg of pEGFP-C2, which is a plasmid DNA (manufactured by Clontech), were blended into 1,200 μl of OPTI-MEM I Reduced Serum Medium (manufactured by Invitrogen Corporation, modified Eagle's minimum essential medium), and the resultant was mixed and suspended to form a complex in the Medium. The geometric mean particle diameter of the complex formed was measured with a Dynamic Light Scattering Particle Size Analyzer (Electrophoretic Light Scattering Spectrophotometer, ELS-8000, manufactured by Otsuka Electronics Co., Ltd.) Subsequently, 100 μl of suspension containing the complex formed was added and mixed to 400 μl of aqueous L-leucine solution (5 mg/ml) in which the L-leucine was dissolved in water in advance, which aqueous solution was contained in a vessel (trunk diameter of 1.8 mm), and 10 samples were prepared in this manner. Thereafter, freeze-drying was carried out using a shelf-type freeze-dryer (Lyovac GT-4, manufactured by Leybold). The disintegration index of the non-powder-form (cake-like) freeze-dried composition (freeze-dried cake) obtained was calculated. Next, a vessel containing the non-powder-form freeze-dried composition (freeze-dried cake) obtained was installed in a jet type dry powder inhaler (having a bellows body 10 capable of supplying an amount of air of about 20 ml; Embodiment 1, FIG. 1) designed such that the bore of the air jet flow path 3 was 1.2 mm and the bore of the discharge flow path 4 was 1.8 mm.

It was verified that, by introducing an amount of air of about 20 ml from the dry powder inhaler into the vessel (giving an air impact arising through an air speed of about 35 m/sec and an air flow rate of about 40 ml/sec), the non-powder-form freeze-dried cake in the vessel was made into fine particles, and the fine particles were jetted out from the vessel via the discharge flow path 4 in an instant. The fine particles were collected using a particle size distribution meter (Aerosizer: manufactured by Amherst Process Instrument, Inc., USA; R. W. Niven: Pharmaceutical Technology, 72-78 (1993)) fitted with an Aerobreather (manufactured by Amherst Process Instrument, Inc., USA, R. W. Niven: Pharmaceutical Technology, 72-78(1993)), which is an artificial lung model capable of directly measuring the particle size distribution of the particles jetted out from the vessel (measurement conditions: breath rate: 60 L/min, breath volume: 1 L, acceleration: 19); the particle size distribution of the fine particles that had been made was thus measured, and the mass median aerodynamic diameter (μm±SD) was calculated from the particle size distribution. The geometric mean particle diameter of particles contained in the suspension in the suspended-form, the disintegration index, and the mass median aerodynamic diameter (μm±SD) of the fine particles jetted out from the inhaler are shown in Table 1 for each of the freeze-dried compositions.

TABLE 1

| Freeze-dried composition | Geometric mean particle diameter (μm) | Disintegration index | Mass median aerodynamic diameter (μm ± SD, MMAD) |
|---|---|---|---|
| LipofectAmine 2000 + pEGFP-C2 + Leucine | 0.827 | 0.186 | 1.762 ± 1.491 |

As shown in Table 1, the non-powder-form freeze-dried cake having a disintegration index of 0.186 was disintegrated by the air impact arising through an air speed of about 35 m/sec and an air flow rate of about 40 ml/sec, becoming a fine-particle-form powdered preparation of mass median aerodynamic diameter of 5 μm or less suitable for transpulmonary administration. Consequently, it was verified that a sample before freeze-drying, even in a non-dissolved form (here, in the suspension form), can be provided as a freeze-dried composition which can be made into fine-particle-form dried powder suitable for transpulmonary administration by the specific air impact defined in the present invention. More specifically, the sample before freeze-drying, even in a non-dissolved form, can be used for the dry powder inhaler for transpulmonary administration of the present invention, and thus transpulmonary administration can be efficiently carried out. Note that genes or antisense molecules capable of offering therapeutic effects by transpulmonary administration can be introduced into a body by employing a cancer suppression gene p53 or a cystic fibrosis transmembrane conductance regulator (CFTR) instead of the plasmid DNA (pEGFP-C2) employed in the present Example. Thus, It should be considered that the dry powder inhalation system of the present invention can be efficiently utilized for gene therapy.

Example 2

Comparative Example 1

72 μg of 'LipofectAMINE 2000', which is a cationic gene transfer liposome (manufactured by Invitrogen corporation) and 10 μg of Oligo-RNA (manufactured by Otsuka Pharmaceutical Co., Ltd.) were mixed and suspended in the presence of OPTI-MEM I Reduced Serum Medium (manufactured by Invitrogen corporation, modified Eagle's minimum essential medium), to form a complex. The geometric mean particle diameter of the complex formed was measured with a Dynamic Light Scattering Particle Size Analyzer (Electrophoretic Light Scattering Spectrophotometer, ELS-8000, manufactured by Otsuka Electronics Co., Ltd.).

Subsequently, 100 μl of suspension containing the complex formed was added to 400 μl of aqueous L-leucine solution (5 mg/ml) prepared by dissolving L-leucine into water in advance, which aqueous solution was contained in a vessel (trunk diameter of 18 mm), and 10 samples were prepared in the same manner, to prepare samples for freeze-drying (Example 2). As a Comparative Example, 400 μl of aqueous solution (5 mg/ml) of dextran 40 instead of L-leucine aqueous solution employed in the above was used for preparing samples for freeze-drying (10 samples) in the same manner as in the above (Comparative Example 1).

Thereafter, freeze-drying was carried out using a shelf-type freeze-dryer (Lyovac GT-4, manufactured by Leybold). The disintegration index of the non-powder-form (cake-like) freeze-dried composition (freeze-dried cake) obtained was calculated. Next, a vessel containing the non-powder-form freeze-dried composition (freeze-dried cake) obtained was installed in a jet type dry powder inhaler (having a bellows body 10 capable of supplying an amount of air of about 20 ml; Embodiment 1, FIG. 1) designed such that the bore of the air jet flow path 3 was 1.2 mm and the bore of the discharge flow path 4 was 1.8 mm.

It was verified that, by introducing an amount of air of about 20 ml from the dry powder inhaler into the vessel (giving an air impact arising through an air speed of about 35 m/sec and an air flow rate of about 40 ml/sec), the non-powder-form freeze-dried cake in the vessel was made into fine particles, and the fine particles were jetted out from the vessel via the discharge flow path 4 in an instant. The fine particles were collected using a particle size distribution meter (Aerosizer: manufactured by Amherst Process Instrument, Inc., USA) fitted with an Aerobreather (manufactured by Amherst Process Instrument, Inc., USA) (measurement conditions: breath rate: 60 L/min, breath volume: 1 L, acceleration: 19), and the particle size distribution of the fine particles that had been made was thus measured, and the mass median aerodynamic diameter (μm±SD) was calculated from the particle size distribution.

The freeze-dried composition of Comparative Example 1 was not dispersed by the air impact arising through an air speed of about 35 m/sec and an air flow rate of about 40 ml/sec, and hence a mass median aerodynamic diameter could not be calculated.

The geometric mean particle diameter of particles contained in the suspension in the suspended-form, the disintegration index, and the mass median aerodynamic diameter (μm±SD) of the fine particles jetted out from the inhaler are shown in Table 2 for each of the freeze-dried compositions (Example 2, Comparative Example 1).

TABLE 2

| Freeze-dried composition | Geometric mean particle diameter (μm) | Disintegration index | Mass median aerodynamic diameter (μm ± SD, MMAD) |
|---|---|---|---|
| Example | | | |
| 2) LipofectAMINE 2000 + Oligo-RNA + Leucine | 1.19 | 0.165 | 1.633 ± 1.496 |
| Comparative Example | | | |
| 1) LipofectAMINE 2000 + Oligo-RNA + Dextran 40 | 1.19 | 0.002 | not dispersed and thus unmeasureable |

As shown in Table 2, the non-powder-form freeze-dried cake having a disintegration index of 0.165 was disintegrated by the air impact arising through an air speed of about 35 m/sec and an air flow rate of about 40 ml/sec, becoming a fine-particle-form powdered preparation of mass median aerodynamic diameter of 5 μm or less suitable for transpulmonary administration even if the sample before freeze-drying was in the non-dissolved form (here, in the suspension form) as in Example 1.

In contrast thereto, the non-powder-form freeze-dried cake having a disintegration index of 0.002 was neither dispersed nor made into fine particles by the air impact, and hence was not suitable for providing a dry powder preparation for transpulmonary administration.

Examples 3 to 5

Comparative Example 2

360 μg of 'Superfect' which is an activate dendrimer molecule (cationic polymer) for gene transfer (manufactured by Qiagen) and 5 μg of Oligo-RNA (manufactured by Otsuka Pharmaceutical Co., Ltd.) (Example 3, Comparative Example 2) or 24 μg of pEGFP-C2 (manufactured by Clontech) which is a plasmid DNA (Examples 4 and 5) were mixed and suspended in the presence of 1,200 μg of OPTI-MEM I Reduced Serum Medium (manufactured by Invitrogen corporation, modified Eagle's minimum essential medium), to form a complex. The geometric mean particle diameter of the complex formed was measured with a Dynamic Light Scattering Particle Size Analyzer (Electrophoretic Light Scattering Spectrophotometer, ELS-8000, Otsuka Electronics Co., Ltd.) or a Laser Diffraction/Scattering Particle Size Distribution Analyzer (Laser Diffraction Particle Size Analyzer, SALD-3000J, Shimadzu Corporation). Subsequently, 100 μl of suspension containing the complex formed was added to 400 μl of aqueous L-leucine-dissolved solution (5 mg/ml) prepared in advance, which aqueous solution was contained in a vessel (trunk diameter of 18 mm) (Examples 3 and 4), or added to 400 μl of aqueous lactose-dissolved solution (5 mg/ml) prepared in advance, which the aqueous solution was contained in a vessel (trunk diameter of 18 mm) (Example 5) and 10 samples were thus prepared for each Example in the same manner, to prepare samples for freeze-drying. As a Comparative Example, 400 μl of aqueous dextran 40-dissolved solution (5 mg/ml) instead of the aqueous L-leucine-dissolved solution employed in Example 3 was used to prepare samples for freeze-drying (10 samples) in the same manner (Comparative Example 2).

Thereafter, freeze-drying was carried out using a shelf-type freeze-dryer (Lyovac GT-4, manufactured by Leybold). The disintegration index of the non-powder-form (cake-like) freeze-dried composition (freeze-dried cake) obtained was calculated. Next, a vessel containing the non-powder-form freeze-dried composition (freeze-dried cake) obtained was installed in a jet type dry powder inhaler (having a bellows body 10 capable of supplying an amount of air of about 20 ml; Embodiment 1, FIG. 1) designed such that the bore of the air jet flow path 3 was 1.2 mm and the bore of the discharge flow path 4 was 1.8 mm.

As for the freeze-dried composition obtained according to Examples 3, 4, and 5, it was verified that, by introducing an amount of air of about 20 ml from the dry powder inhaler into the vessel (giving an air impact arising through an air speed of about 35 m/sec and an air flow rate of about 40 ml/sec), the non-powder-form freeze-dried cake in the vessel was made into fine particles, and the fine particles were jetted out from the vessel via the discharge flow path 4 in an instant. The fine particles were collected using a particle size distribution meter (Aerosizer: manufactured by Amherst Process Instrument, Inc., USA) fitted with an Aerobreather (manufactured by Amherst Process Instrument, Inc., USA) (measurement conditions: breath rate: 60 L/min, breath volume: 1 L, acceleration. 19); the particle size distribution of the fine particles that had been made was thus measured, and the mass median aerodynamic diameter (μm±SD) was calculated from the particle size distribution in the same manner as in Example 1.

In contrast thereto, the non-powder form freeze-dried cake of Comparative Example 2 was not dispersed by the air impact arising through an air speed of about 35 m/sec and an air flow rate of about 40 ml/sec, and hence the mass median aerodynamic diameter was not obtained.

The geometric mean particle diameter of particles contained in the suspension in the suspended-form, the disintegration index, and the mass median aerodynamic diameter (μm±SD) of the fine particles jetted out from the inhaler are shown in Table 3 for each of the freeze-dried compositions (Examples 3 to 5, Comparative Example 2).

TABLE 3

| Freeze-dried composition | Geometric mean particle diameter (μm) | Disintegration index | Mass median aerodynamic diameter (μm ± SD, MMAD) |
|---|---|---|---|
| Example | | | |
| 3) Superfect + Oligo-RNA + Leucine | 11.12 | 0.225 | 1.578 ± 1.403 |
| 4) Superfect + pEGFP-C2 + Leucine | 3.74 | 0.189 | 1.646 ± 1.420 |
| 5) Superfect + pEGFP-C2 + Lactose | 3.74 | 0.080 | 2.848 ± 1.873 |
| Comparative Example | | | |
| 2) Superfect + Oligo-RNA + Dextran 40 | 11.12 | 0.003 | not dispersed and thus unmeasureable |

As shown in Table 3, the non-powder-form freeze-dried cakes having a disintegration index of 0.080 to 0.225, that is, 0.05 or more, were disintegrated by the air impact arising through an air speed of about 35 m/sec and an air flow rate of about 40 ml/sec, becoming a fine-particle-form powdered preparations of mass median aerodynamic diameter of 5 μm or less suitable for transpulmonary administration even if the sample before freeze-dried was in the non-dissolved form (here, in the suspension form) as in Example 1 and particles contained therein had the geometric mean particle diameter of 11 μm and thus were prone to aggregate.

In contrast thereto, the non-powder-form freeze-dried cake having the disintegration index of 0.003 was neither dispersed nor made into fine particles by the air impact, hence was not suitable for preparing a dry powder preparation for transpulmonary administration.

Consequently, it was verified that the samples before freeze-drying, even in the non-dissolved form (here, in the suspension form), can be provided as a freeze-dried compositions which can be made into fine-particle-form dried powders suitable for transpulmonary administration by the specific air impact defined in the present invention. More specifically, the samples before freeze-drying, even in the non-dissolved form, can be used for the dry powder inhaler for transpulmonary administration of the present invention, and thus transpulmonary administration can be efficiently carried out. Note that genes or antisense molecules capable of offering curative effects by transpulmonary administration can be introduced into a body by employing a cancer suppression gene p53 or a cystic fibrosis transmembrane conductance regulator (CFTR) instead of the plasmid DNA (pEGFP-C2) employed in the present Example. Moreover, as Oligo-RNA is a kind of RNAi (RNA interference) and is a RNA duplex applicable to RNAi technology, a short duplex RNA may thus be introduced corresponding to a target gene, whereby a function of a messenger RNA of the target gene can be specifically controlled (suppressed), and hence is applicable to a therapy for lung cancer.

Thus, it should be considered that the dry powder inhalation system of the present invention can be efficiently utilized for gene therapy.

Example 6

360 μg of 'Superfect', which is an activate dendrimer molecule for gene transfer (manufactured by Qiagen), and 5 μg of Oligo-RNA (manufactured by Otsuka Pharmaceutical Co., Ltd.) were mixed and suspended in the presence of 1,200 μg of OPTI-MEM I Reduced Serum Medium (manufactured by Invitrogen corporation, modified Eagle s minimum essential medium), to form a complex. The geometric mean particle diameter of the complex formed was measured with a Laser Diffraction/Scattering Particle Size Distribution Analyzer (Laser Diffraction Particle Size Analyzer, SALD-3000J, Shimadzu Corporation).

Subsequently, 100 μl of suspension containing the complex formed was added to 400 μl of aqueous L-Valine-dissolved solution (2.5 mg/ml) prepared in advance, which aqueous solution was contained in a vessel (trunk diameter of 18 mm), and 10 samples were prepared in the same manner for each Example, to prepare samples for freeze-drying. Thereafter, freeze-drying was carried out using a shelf-type freeze-dryer (Lyovac GT-4, manufactured by Leybold). The disintegration index of the non-powder-form (cake-like) freeze-dried composition (freeze-dried cake) obtained was calculated.

Next, a vessel containing the non-powder-form freeze-dried composition (freeze-dried cake) obtained was installed in a jet type dry powder inhaler (having a bellows body 10 capable of supplying an amount of air of about 20 ml; Embodiment 1, FIG. 1) designed such that the bore of the air jet flow path 3 was 1.2 mm and the bore of the discharge flow path 4 was 1.8 mm.

It was verified that, by introducing an amount of air of about 20 ml from the dry powder inhaler into the vessel (giving an air impact arising through an air speed of about 35 m/sec and an air flow rate of about 40 ml/sec), the freeze-dried composition of Example 6 was made into fine particles, and the fine particles were jetted out from the vessel via the discharge flow path 4 in an instant. The fine particles were collected using a particle size distribution meter (Aerosizer: manufactured by Amherst Process Instrument, Inc., USA) fitted with an Aerobreather (manufactured by Amherst Process Instrument, Inc., USA (measurement conditions: breath rate: 60 L/min, breath volume: 1 L, acceleration: 19), the particle size distribution of the fine particles that had been made was thus measured, and the mass median aerodynamic diameter (μ±SD) was calculated from the particle size distribution in the same manner as in Example 1.

The geometric mean particle diameter of particles contained in the suspension in the suspended-form, the disintegration index, and the mass median aerodynamic diameter (μm±SD) of the fine particles jetted out from the inhaler are shown in Table 4 for each of the freeze-dried compositions.

TABLE 4

| Freeze-dried composition | Geometric mean particle diameter (μm) | Disintegration index | Mass median aerodynamic diameter (μm ± SD, MMAD) |
|---|---|---|---|
| 6) Superfect + Oligo-RNA + Valine | 13.9 | 0.275 | 1.589 ± 1.553 |

As shown in Table 4, the non-powder-form freeze-dried cake having a disintegration index of 0.275 was disintegrated by the air impact arising through an air speed of about 35 m/sec and an air flow rate of about 40 ml/sec, becoming a fine-particle-form powdered preparation of mass median aerodynamic diameter of 5 μm or less suitable for transpulmonary administration even if the sample before freeze-dried was in the non-dissolved form (here, in the suspension form) as in Example 1 and particles contained therein had the geometric mean particle diameter of about 14 μm and thus were prone to aggregate.

As shown by the results obtained in Examples 2 to 6, it was verified that the samples before freeze-drying, even in the non-dissolved form (here, in the suspension form), can be provided as a freeze-dried composition which can be made into fine-particle-form dried powder suitable for transpulmonary administration by the specific air impact defined in the present invention. More specifically, the freeze-dried composition containing ingredients can be used for the dry powder inhaler for transpulmonary administration of the present invention even when the ingredients are not dissolved or are difficult to dissolve into the solvent, and thus transpulmonary administration can be efficiently carried out.

Examples 7 and 8

A solution obtained by dissolving insulin (0.2 mg in Example 7 and 1 mg in Example 8) (Recombinant Human Insulin Crystal, manufactured by Biobras, Brazil; relative activity: 26.4 U/mg) into hydrochloric acid solution, and a solution obtained by dissolving various carriers as shown in Table 5 into purified water were separately prepared, and these solutions were mixed at the proportion shown in Table 5, to form various suspensions in the suspended form. The geometric mean particle diameter of particles contained in the suspensions was measured with a Laser Diffraction/Scattering Particle Size Distribution Analyzer (Laser Diffraction Particle Size Analyzer, SALD-3000J, Shimadzu Corporation).

Subsequently, the various suspensions were filled into vessels (trunk diameter 18 mm), and freeze-drying was carried out using a shelf-type freeze-dryer (Lyovac GT-4, manufactured by Leybold). The disintegration index of the non-powder-form freeze-dried compositions (freeze-dried cake) obtained was calculated. Next, a vessel (trunk diameter 18 mm) filled with each non-powder-form freeze-dried composition obtained was installed in a self-inhaling type dry powder inhaler configured such that the bore of the air introduction flow path 17 was 1.99 mm and the bore of the suction flow path 16 was 1.99 mm (Embodiment 3, FIG. 3). Using this, the fine particle fraction (%) was calculated with a twin impinger (manufactured by Copley, UK) (applying an air impact arising through an air speed of about 95 m/sec and an air flow rate of about 295 ml/sec to the freeze-dried cake). The geometric mean particle diameter of particles contained in the suspension in the suspended-form, the disintegration index and the fine particle fraction (%) are shown for each of the freeze-dried compositions in Table 5.

TABLE 5

| Freeze-dried composition | Geometric mean particle diameter (μm) | Disintegration index | Fine particle fraction (%) |
|---|---|---|---|
| Example | | | |
| 7) 0.2 mg insulin + 0.1 mg leucine + 0.042 mg arginine (pH 6.5) | 0.52 | 0.292 | 95.3% |
| 8) 1 mg insulin + 0.6 mg phenylalanine + 0.11 mg arginine (pH 6.4) | 0.63 | 0.238 | 57.9% |

As can be seen from Table 5, the non-powder-form freeze-dried compositions (freeze-dried cakes), which showed a disintegration index of at least 0.238, were easily made into fine particles in the vessel by the above-mentioned air impact, even though the sample before freeze-drying was in the form of containing an active ingredient (insulin) in the non-dissolved form, and it was possible to produce a powdered preparation suitable for transpulmonary administration.

Examples 9 to 11

A solution obtained by dissolving 1 mg of insulin (Recombinant Human Insulin Crystal, manufactured by Biobras, is Brazil; relative activity: 26.4 U/mg) into hydrochloric acid solution, and a solution obtained by dissolving 0.5 mg of phenylalanine into purified water were separately prepared. These solutions were mixed, and then the pH was adjusted with sodium hydroxide, to form various suspensions in the suspended form. The geometric mean particle diameter of particles contained in the suspensions was measured with a Laser Diffraction/Scattering Particle Size Distribution Analyzer (Laser Diffraction Particle Size Analyzer, SALD-3000J, manufactured by Shimadzu Corporation).

Subsequently, the various suspensions were filled into vessels (trunk diameter 18 mm), and freeze-drying was carried out using a shelf-type freeze-dryer (Lyovac GT-4, manufactured by Leybold). The disintegration index of the non-powder-form freeze-dried compositions (freeze-dried cake) obtained was calculated. Next, a vessel (trunk diameter 18 mm) filled with each non-powder-form freeze-dried composition obtained was installed in a jet-type dry powder inhaler (having a bellows body capable of supplying an amount of air of about 20 ml) configured such that the bore of the air introduction flow path was 1.2 mm and the bore of the suction flow path was 1.8 mm. Using this, the fine particle fraction (%) was calculated with a twin impinger (manufactured by Copley, UK) (applying an air impact arising through an air speed of about 35 m/sec and an air flow rate of about 40 ml/sec to the freeze-dried cake). The geometric mean particle diameter of particles contained in the suspension in the suspended-form, the disintegration index and the fine particle fraction (%) are shown for each of the freeze-dried compositions in Table 6.

TABLE 6

| Freeze-dried composition | Geometric mean particle diameter (μm) | Disintegration index | Fine particle fraction (%) |
|---|---|---|---|
| Example | | | |
| 9) 1 mg insulin + 0.5 mg phenylalanine (pH 6.0) | 3.10 | 0.39 | 69.3% |
| 10) 1 mg insulin + 0.5 mg phenylalanine (pH 6.4) | 0.55 | 0.39 | 75.1% |
| 11) 1 mg insulin + 0.5 mg phenylalanine (pH 6.6) | 0.61 | 0.36 | 72.0% |

As can be seen from Table 6, the non-powder-form freeze-dried compositions (freeze-dried cakes), which showed a disintegration index of at least 0.36, were easily made into fine particles in the vessel by the above-mentioned air impact, even though the sample before freeze-drying was in the form of containing an active ingredient (insulin) in the non-dissolved form, and it was possible to produce a powdered preparation suitable for transpulmonary administration.

Examples 12 and 13

A solution obtained by dissolving 0.1 mg of insulin (Recombinant Human Insulin Crystal, manufactured by Biobras, Brazil; relative activity: 26.4 U/mg) into hydrochloric acid solution, and a solution obtained by dissolving various carriers as shown in Table7 into purified water were separately prepared. These solutions were mixed, and then the pH was adjusted with sodium hydroxide, to form various suspensions in the suspended form. The geometric mean particle diameter of particles contained in the suspensions was measured with a Laser Diffraction/Scattering Particle Size Distribution Analyzer (Laser Diffraction Particle Size Analyzer, SALD-3000J. Shimadzu Corporation).

Subsequently, the various suspensions were filled into vessels (trunk diameter 18 mm), and freeze-drying was carried out using a shelf-type freeze-dryer (Lyovac GT-4, manufactured by Leybold). The disintegration index of the non-powder-form freeze-dried compositions (freeze-dried cake) obtained was calculated. Next, a vessel (trunk diameter 18 mm) filled with each non-powder-form freeze-dried composition obtained was installed in a self-inhaling type dry powder inhaler configured such that the bore of the air introduction flow path 17 was 1.99 mm and the bore of the suction flow path 16 was 1.99 mm (Embodiment 3, FIG. 3). Using this, the fine particle fraction (%) was calculated with a twin impinger (manufactured by Copley, UK) (applying an air impact arising through an air speed of about 95 m/sec and an air flow rate of about 295 ml/sec to the freeze-dried cake). The geometric mean particle diameter of particles contained in the suspension in the suspended-form, the disintegration index and the fine particle fraction (%) are shown for each of the freeze-dried compositions in Table 7.

TABLE 7

| Freeze-dried composition | Geometric mean particle diameter (μm) | Disintegration index | Fine particle fraction (%) |
|---|---|---|---|
| Example | | | |
| 12) 0.1 mg insulin + 0.5 mg Leucyl-valine (pH 6.4) | 0.54 | 0.115 | 68.7% |
| 13) 0.1 mg insulin + 1.5 mg Leucyl-valine (pH 6.5) | 0.67 | 0.051 | 58.9% |

As can be seen from Table 7, the non-powder-form freeze-dried compositions (freeze-dried cakes), which showed a disintegration index of at least 0.051, were easily made into fine particles in the vessel by the above-mentioned air impact, even though the sample before freeze-drying was in the form of containing an active ingredient (insulin) in the non-dissolved form, and it was possible to produce a powdered preparation suitable for transpulmonary administration.

Example 14

A solution obtained by dissolving 0.1 mg of insulin (Recombinant Human Insulin Crystal, manufactured by Biobras, Brazil; relative activity: 26.4 U/mg) into hydrochloric acid solution, and a solution obtained by dissolving valine into purified water were separately prepared. These solutions were mixed, and then the pH was adjusted to pH 6.5 with sodium hydroxide, to form various suspensions in the suspended form. The geometric mean particle diameter of particles contained in the suspensions was measured with a Laser Diffraction/Scattering Particle Size Distribution Analyzer (Laser Diffraction Particle Size Analyzer, SALD-3000J, Shimadzu Corporation).

Subsequently, the various suspensions were filled into vessels (trunk diameter 18 mm), and freeze-drying was carried out using a shelf-type freeze-dryer (Lyovac GT-4, manufactured by Leybold). The disintegration index of the non-powder-form freeze-dried compositions (freeze-dried cake) obtained was calculated. Next, a vessel (trunk diameter 18 mm) filled with each non-powder-form freeze-dried composition obtained was installed in a self-inhaling type dry powder inhaler configured such that the bore of the air introduction flow path 17 was 1.99 mm and the bore of the suction flow path 16 was 1.99 mm (Embodiment 3, FIG. 3).

Using this, an air impact arising through an air speed of about 1 m/sec and an air flow rate of about 17 ml/sec is applied to the non-powder form freeze-dried composition (freeze-dried cake) contained in the vessel, and fine particles generated were directly jetted from the inhaler to an Aerosizer (manufactured by Amherst Process Instrument, Inc., USA) fitted with an Aerobreather (manufactured by Amherst Process Instrument, Inc., USA: measurement conditions: breath rate: 1 L/min, breath volum: 0.1 L), which is an artificial lung model capable of directly measuring the particle size distribution of the jetted particles; the particle size distribution of the fine particles was thus measured. From the results, the mass median aerodynamic diameter (μm±SD) of the jetted fine particles was calculated. The geometric mean particle diameter of particle contained in the suspension in non-suspended form, the disintegration index for each of the freeze-dried compositions and the mass median aerodynamic diameter of the particles jetted out from the inhaler are shown in Table 8.

TABLE 8

| Freeze-dried composition | Geometric mean particle diameter (μm) | Disintegration index | Mass median aerodynamic diameter (μm ± SD, MMAD) |
|---|---|---|---|
| 14) 0.1 mg insulin + 0.5 mg Valine | 0.57 | 0.221 | 1.875 ± 1.384 |

As can be seen from Table 8, the non-powder-form freeze-dried compositions (freeze-dried cakes), which showed a disintegration index of 0.221, were easily made into fine particles in the vessel by the above-mentioned air impact, even though the sample before freeze-drying was in the form of containing an active ingredient (insulin) in the non-dissolved form, and it was possible to produce a powdered preparation suitable for transpulmonary administration.

Reference Examples 1 to 5

Insulin (Recombinant Human Insulin Crystal, manufactured by Biobras, Brazil; relative activity: 26.4 U/mg) (1 mg, 2 mg), or insulin and any of various carriers as shown in Table 6, was/were made up to 0.2 ml by dissolving in injection distilled water containing hydrochlolic acid, this was filled into vessels (trunk diameter 18 mm), and freeze-drying was carried out using a shelf-type freeze-dryer (Lyovac GT-4, manufactured by Leybold). The disintegration index of the non-powder-form freeze-dried composition (freeze-dried cake) obtained was calculated. Next, a vessel (trunk diameter 18 mm) filled with the non-powder-form freeze-dried composition obtained was installed in a self-inhaling type dry powder inhaler (Embodiment 3, FIG. 3) designed such that the bore of the air introduction flow path 17 was 1.99 mm and the bore of the suction flow path 16 was 1.99 mm (Embodiment 3, FIG. 3). Using this, the fine particle fraction (%) was calculated with a twin impinger (manufactured by Copley, UK) (applying an air impact arising through an air speed of about 95 m/sec and an air flow rate of about 295 ml/sec to the freeze-dried cake). The disintegration index and the fine particle fraction (%) are shown in Table 9 for each of the freeze-dried compositions.

TABLE 9

| Freeze-dried composition | Disintegration index | Fine particle fraction (%) |
|---|---|---|
| Ref. 1) 1 mg insulin | 0.159 | 75.0 |
| Ref. 2) 1 mg insulin + 1.4 mg leucine | 0.145 | 80.7 |
| Ref. 3) 1 mg insulin + 1.0 mg valine | 0.110 | 79.4 |
| Ref. 4) 2 mg insulin | 0.177 | 42.4 |
| Ref. 5) 2 mg insulin + 1.4 mg leucine | 0.137 | 65.1 |

As can be seen from Table 9, the non-powder-form freeze-dried compositions (freeze-dried cakes), which showed a disintegration index of 0.110 or more, were easily made into fine particles in the vessel by the above-mentioned air impact, with it being possible to produce a powdered preparation suitable for transpulmonary administration.

Reference Examples 6 to 10

1 mg of insulin (Recombinant Human Insulin Crystal, manufactured by Biobras, Brazil; relative activity: 26.4 U/mg) and any of various carriers (1.5 mg) as shown in Table 7 were made up to 0.5 ml by dissolving in injection distilled water containing hydrochloric acid, this was filled into vessels (trunk diameter 18 mm), and freeze-drying was carried out using a shelf-type freeze-dryer (Lyovac GT-4, manufactured by Leybold). The disintegration index of the non-powder-form freeze-dried composition (freeze-dried cake) obtained was calculated. Next, a vessel (trunk diameter 18 mm) filled with the non-powder-form freeze-dried composition obtained was installed in a jet type dry powder inhaler (having a bellows body capable of supplying an amount of air of about 20 ml, Embodiment 1, FIG. 1) designed such that the bore of the air jet flow path was 1.2 mm and the bore of the discharge flow path was 1.8 mm. Using this, an air impact arising through an air speed of about 35 m/sec and an air flow rate of about 40 ml/sec is applied to the non-powder form freeze-dried composition (freeze-dried cake) contained in the vessel, and fine particles generated were directly jetted from the inhaler to an Aerosizer (manufactured by Amherst Process Instrument, Inc., USA) fitted with an Aerobreather (manufactured by Amherst Process Instrument, Inc., USA: measurement conditions: breath rate: 60 L/min, breath volume: 1 L), which is an artificial lung model capable of directly measuring the particle size distribution of the jetted particles; the particle size distribution of the fine particles was thus measured. From the results, the mass median aerodynamic diameter (μm±SD) of the jetted fine particles was calculated.

Furthermore, a vessel (trunk diameter 18 mm) filled with the non-powder-form freeze-dried composition obtained was installed in a self-inhaling type dry powder inhaler designed such that the bore of the air introduction flow path was 1.99 mm and the bore of the suction flow path was 1.99 mm (Embodiment 3, FIG. 3). Using this, the fine particle fraction (%) was calculated with a twin impinger (manufactured by Copley, UK) (applying an air impact arising through an air speed of about 95 m/sec and an air flow rate of 295 ml/sec to the freeze-dried cake).

The disintegration index, the mass median aerodynamic diameter (μm±SD) of the fine particles jetted out from the jet type dry powder inhaler, and the fine particle fraction (%) of the fine particles obtained by the self-inhaling type dry powder inhaler are shown in Table 10 for each of the freeze-dried compositions.

TABLE 10

| Freeze-dried composition | Disintegration index | Mass median aerodynamic diameter (μm ± SD, MMAD) | Fine particle fraction (%) |
|---|---|---|---|
| Reference Examples | | | |
| 6) Insulin + isoleucine | 0.124 | 1.759 ± 1.425 | 71.1 |
| 7) Insulin + leucine | 0.250 | 1.954 ± 1.454 | 74.1 |
| 8) Insulin + valine | 0.124 | 2.007 ± 1.438 | 72.1 |
| 9) Insulin + phenylalanine | 0.204 | 1.872 ± 1.477 | 62.0 |
| 10) Insulin + D-mannitol | 0.160 | 2.239 ± 1.435 | 61.2 |

As shown in Table 10, the non-powder-form freeze-dried compositions (freeze-dried cakes), which showed a disintegration index of 0.124 or more, were easily made into fine particles in the vessel by the air impact arising through an air speed of about 35 m/sec and an air flow rate of about 40 ml/sec or the air impact arising through an air speed of about 95 m/sec and an air flow rate of 295 ml/sec. Moreover, the mean particle diameter of the fine particles manufactured by the air impact arising through an air speed of about 95 m/sec and an air flow rate of 295 ml/sec was 5 μm or less, and hence it was possible to produce a powdered preparation suitable for transpulmonary administration.

INDUSTRIAL APPLICABILITY

According to the dry powder inhalation system for transpulmonary administration of the present invention, a freeze-dried composition can be made Into fine particles down to a size necessary for delivery into the lungs, and moreover administration of the fine particles Into the lungs through inhalation is possible. That is, according to the dry powder inhalation system for transpulmonary administration of the present invention, a freeze-dried composition that has been prepared in a non-powder form can be made into fine particles at the time of use (the time of administration), and administered through inhalation at the same time, and hence a special operation for making the preparation into fine particles becomes unnecessary. Consequently, according to the dry powder inhalation system for transpulmonary administration (preparation system) of the present invention, there is no risk of loss during the manufacturing process (deactivation of the drug or collection loss through a filling operation) or loss during storage (for example deactivation of the drug due to being stored in a fine particle form), or contamination with impurities during the manufacturing process; a desired fixed amount can thus be administered stably. This is useful in particular with preparations having as an active ingredient a generally expensive pharmacologically active substance such as a protein or a peptide.

The proportion of effective particles (fine particle fraction) attained by the dry powder inhalation system for transpulmonary administration of the invention is at least 10%, and can be increased to at least 20%, at least 25%, at least 30% or at least 35%. U.S. Pat. No. 6,153,224 indicates that, with many of prior art dry powder inhalers, the proportion of the active ingredient (particles) to adhere to the lower portions of the lungs is only about 10% of the amount of the active ingredient inhaled. Further, Japanese Unexamined Patent Publication No. 2001-151673 states that the amount of an inhalation powder preparation reaching the lungs (lung reaching proportion) is generally about 10% of the drug discharged from the preparation. Therefore, the dry powder inhalation system of the invention is valuable in that it is capable of achieving a higher proportion of effective particles (fine particle fraction) than prior art powder inhalation preparations.

According to the freeze-dried composition and jet type dry powder inhaler of the present invention, the freeze-dried composition can be made into fine particles merely by jetting air into the vessel from the air jet flow path using the air pressure-feeding means and thus applying a slight air impact to the freeze-dried composition. The making into fine particles can thus be carried out at the time of use with an dry powder inhaler having a simple structure and moreover with simple handling. Moreover, because the dry powder inhaler has a simple structure, it can be produced with a low manufacturing cost, and hence mass distribution is possible.

Moreover, according to the jet type dry powder inhaler, by adjusting the speed of compression of the air pressure-feeding means such as a bellows body, the amount sucked in of the aerosol (powdered preparation) can be adjusted in accordance with the respiratory ability of the user. Moreover, by using a single integrated needle part, the operation of piercing the stopper of the vessel with the needle part becomes simple.

Furthermore, according to the self-inhaling type dry powder inhaler, the freeze-dried composition can be made into an aerosol (made into fine particles) through an air impact being generated by the inhalation pressure of the user, and hence the making into fine particles and administration into the lungs of the freeze-dried composition can be carried out at the same time as the user inhaling, and thus it can be expected that the drug will be administered in a stable amount with no loss. Moreover, a separate special operation for making into an aerosol (making into fine particles) is unnecessary, and hence handling is easy. Moreover, as with the jet type, by using a single integrated needle part, the operation of piercing the elastic port stopper of the vessel with the needle part becomes simple.

According to the dry powder inhaler of the present invention, by piercing the stopper of the vessel with the tip of the needle part having the suction flow path and the air introduction flow path, and air in the vessel then being sucked in from the suction port by the inhalation pressure of the user (patient), air can be made to flow into the vessel from the air introduction flow path of the needle part, thus applying an air impact to the freeze-dried composition, and the freeze-dried composition that has been made into a powder can be sucked in from the vessel.

Moreover, in the case of the dry powder inhaler of the present invention disclosed as Embodiment 4 in particular, the following effects are exhibited.

When trying to apply an effective air impact to the freeze-dried composition and suck the powder-form freeze-dried composition that has been made into fine particles from the vessel, the cross-sectional areas of the suction flow path and the air introduction flow path must be made large, and hence the diameter of the needle part must be made large.

However, in the case of piercing a needle part having a large diameter through the stopper, it becomes necessary to hold the vessel securely, and in this state move the vessel towards the needle tip without deviating away from the axis of the needle part, and push the stopper against the needle tip with a large force.

As described above, the dry powder inhaler of the present invention thus has a holder part that holds the vessel, a guide part of the holder part, and a holder operating part having a mechanism part and an operating member that operates the mechanism part. Therefore, by holding the vessel with the holder part, moving the vessel along the axis of the needle part following the guide part towards the needle tip, and operating the operating member, it is thus possible to pierce the needle part through the stopper of the vessel using a relatively low force.

In this way, according to the dry powder inhaler of the present invention, the stopper of the vessel can be pierced by the needle part easily and reliably.

Moreover, if a constitution is adopted in which the housing is formed in a tubular shape, the suction port is formed at a tip part of the housing, a housing chamber for the vessel is formed in the housing, the needle part is disposed in the housing so that the needle tip points towards the housing chamber, an introduction port for introducing outside air that communicates with the air introduction flow path of the needle part is provided in a wall of the housing, and the holder part is advanced and retreated in the axial direction of the housing in the housing chamber using the holder operating part, then a pencil-shaped dry powder inhaler can be formed, which is easy to use and conveniently portable.

Moreover, if the constitution is made to be such that the housing is formed from a housing main body having a removal/insertion port for the vessel in a position in which the holder part is retreated, and a lid for the removal/insertion port that is connected to the housing main body by a hinge, the holder operating part has a mechanism part which moves the holder part forwards when the lid is pushed down and the removal/insertion port closed, and moves the holder part backwards when the lid is lifted up and the removal/insertion port opened, and the lid is used as the operating member of the mechanism part, then the mechanism part of the holder operating part can be simplified and in the manufacturing cost. Moreover, the removal/insertion port of the vessel can be closed at the same time as piercing the stopper of the vessel with the needle tip, and hence use becomes easier.

The invention claimed is:

1. A dry powder inhalation system for transpulmonary administration, comprising:
   (1) a vessel housing a freeze-dried composition in non-powder cake form prepared by freeze-drying a liquid composition containing ingredients in a non-dissolved form, and has:
      (i) a disintegration index of 0.05 or more, and
      (ii) a property of becoming fine particles having a mass median aerodynamic diameter of 10 microns or less or a fine particle fraction of 10% or more upon receiving an air impact having an air speed of at least 1 m/sec and an air flow rate of at least 17 ml/sec; and
   (2) a device comprising a member capable of applying said air impact to the freeze-dried composition in said vessel, and a member for discharging the freeze-dried composition that has been made into fine particles.

2. The dry powder inhalation system for transpulmonary administration according to claim 1, wherein the vessel and the device are used in combination at the time of inhalation.

3. The dry powder inhalation system for transpulmonary administration according to claim 1, wherein the freeze-dried composition contains a drug as an active ingredient.

4. The dry powder inhalation system for transpulmonary administration according to claim 1, wherein the device is:
   A) a dry powder inhaler for transpulmonary administration, being a device used for making a freeze-dried composition that has been housed in non-powder cake form in a vessel into fine particles and administering the resulting fine particles to a user by inhalation,
   comprising a needle part having an air jet flow path, a needle part having a discharge flow path, air pressure-feeding member for feeding air into the air jet flow path of said needle part, and an inhalation port that communicates with the discharge flow path of said needle part,
   and characterized by being constituted such that a stopper that seals up said vessel is pierced by said needle parts, thus communicating the air jet flow path and the discharge flow path with the inside of said vessel, and air is jetted into said vessel through said air jet flow path using said air pressure-feeding member, thus pulverizing said freeze-dried composition in non-powder cake form into fine particles by the impact of the jetted air, and discharging the fine particles obtained from the inhalation port via said discharge flow path, or
   B) a dry powder inhaler for transpulmonary administration, being a device used for making a freeze-dried composition that has been housed in non-powder cake form in a vessel into fine particles, and administering the resulting fine particles to a user by inhalation,
   comprising a needle part having a suction flow path, a needle part having an air introduction flow path, and an inhalation port that communicates with said suction flow path,
   and characterized by being constituted such that, in a state in which a stopper sealing up said vessel has been pierced by said needle parts, through the inhalation pressure of the user, air in said vessel is inhaled from said inhalation port, and at the same time outside air flows into said vessel, at a negative pressure, through said air introduction flow path, and as a result said freeze-dried composition in non-powder cake form is pulverized into fine particles by the impact of the air flowing in, and the fine particles obtained are discharged from the inhalation port through said suction flow path.

* * * * *